United States Patent [19]

Hoffman et al.

[11] Patent Number: 4,951,222

[45] Date of Patent: Aug. 21, 1990

[54] METHOD AND SYSTEM FOR DIMENSIONAL AND WEIGHT MEASUREMENTS OF ARTICLES OF MANUFACTURE BY COMPUTERIZED TOMOGRAPHY

[75] Inventors: Carvel D. Hoffman, Bethlehem; R. Creighton Booth, Coopersburg; John C. Clymer, Bethlehem, all of Pa.; Richard J. Casler, Newtown, Conn.

[73] Assignee: Bethlehem Steel Corporation, Bethlehem, Pa.

[21] Appl. No.: 204,588

[22] Filed: Jun. 9, 1988

[51] Int. Cl.$^5$ .............................................. G01B 15/00
[52] U.S. Cl. .................................... 364/507; 378/54; 378/58; 250/359.1
[58] Field of Search .................... 364/506, 507; 378/7, 378/54, 55, 57, 58, 19, 59, 62; 250/358.1, 359.1

[56] References Cited

U.S. PATENT DOCUMENTS

| | | | |
|---|---|---|---|
| 3,808,437 | 4/1974 | Miyagawa et al. | 378/54 |
| 4,057,725 | 11/1977 | Wagner | 250/360 |
| 4,187,425 | 2/1980 | Thomson | 378/59 |
| 4,196,352 | 4/1980 | Berninger et al. | 250/445 T |
| 4,203,036 | 5/1980 | Tschunt | 250/445 T |
| 4,220,863 | 9/1980 | McBride et al. | 250/445 T |
| 4,330,835 | 5/1982 | Gehm | 378/54 X |
| 4,435,643 | 3/1984 | Junck | 378/55 X |
| 4,495,635 | 1/1985 | Dobbs | 378/54 X |
| 4,511,801 | 4/1985 | Tatham et al. | 250/394 |
| 4,725,963 | 2/1988 | Taylor et al. | 364/507 |

Primary Examiner—Jerry Smith
Assistant Examiner—Steven G. Kibby
Attorney, Agent, or Firm—Ratner & Prestia

[57] ABSTRACT

Tomographic imaging of an inanimate object in which a fan-shaped beam of radiation is generated and divided into fan ray elements which are directed through a planar section of the object and detected by a set of detectors. Each detector produces a signal representative of the intensity of the radiation of a detected fan ray element and selected coordinates defining a cross-sectional image of the object are determined from the intensity signals of the detectors. The coordinates are stored and displayed on a display device. The detectors include a scintillation crystal which is provided with a half-solid cylinder of lead disposed on a side of the crystal.

12 Claims, 29 Drawing Sheets

NOTE 1  CORNER = a OR b AND DETECTOR X > CORNER X OR
        CORNER = c OR d AND DETECTOR X < CORNER X

METHOD AND SYSTEM FOR DIMENSIONAL AND WEIGHT MEASUREMENTS OF ARTICLES OF MANUFACTURE BY COMPUTERIZED TOMOGRAPHY

A portion of the disclosure of this patent document contains material which is subject to copyright protection. The copyright owner has no objection to the facsimile reproduction by anyone of the patent document or the patent disclosure as it appears in the Patent and Trademark Office patent file or records but otherwise reserves all copyright rights whatsoever.

BACKGROUND OF THE INVENTION

1. Field of the Invention

This invention relates to a device and method for measuring cross-sectional or edge boundary dimensions and the weight per unit length, typically weight per foot (WPF). More particularly, the invention relates to the measuring of the edge boundaries of steel products by computerized tomography during rolling thereof.

2. Background Art

In prior art manufacturing processes, the principal parameters for controlling manufacturing operating conditions are weight per unit length, i.e., weight per foot, measurements in combination with measurements of several key dimensions. In this type of process, many dimensional measurements are required, preferably to ultimately obtain a cross-sectional profile of the product. The prior art methods of obtaining these measurements generally involve taking optical measurements of the object dimensions, determining cross-sectional area and then multiplying the product cross-sectional area by its density. However, with this technology it was very difficult to obtain weight per unit length measurement accuracies of up to about 0.1%. In addition, optical measurement of the cross-sectional profile of complex shapes such as I-beams, pipes or tubing is very difficult due to an inaccessibility to the inner surface thereof.

The prior art also teaches the use of radiation transmission for measuring the product thickness, typically of flat rolled products. Although results regarding measurements of product thickness have been generally good using these techniques, no known prior art method has taught how to use product dimension determination by radiation transmission to determine the edge boundaries of cross-sectional area, and/or weight per unit length of various products, especially complicated and intricate shapes.

One prior art system presently marketed under the trade name γ-TRISCOPE by Fuji Electric Company and Kawasaki Steel Corporation employs penetration and absorption of γ-rays to continously measure the wall thickness of pipes during manufacturing operations. However, this prior art system generally requires stationary radiation sources operating with a stationary small number of detectors, does not effect 360° scanning, and cannot be readily employed to measure crossections of intricate and complicated shapes.

Other non-medical uses of radiation systems, e.g., medical CAT systems, are discussed in: "Applications of Computerized Axial Tomography in the field of Nondestructive Testing", MATERIAL PRUF, 22, No. 5, May 1980, pp. 214–217, by V. P. Reimers et al., whose disclosure is incorporated herein by reference. This system involves the use of a CAT system having an X-ray source to reconstruct images of extruded aluminum sections, blocks and pipes and wood telephone poles. However, there is no discussion of how to use the system for on-line measurements during production of, for example, rolled steel shapes, nor of any arrangement for determing product dimensions or weight per unit length of complex shapes.

Other prior art systems include medical CAT systems which generally employ a stationary ring of radiation detectors, and a moving low energy level, e.g., 150 KeV X-ray source to scan a patient's body. An image is thus reconstructed which a physician qualitatively examines on a CRT to obtain desired information. Examples of such systems are disclosed in: U.S. Pat. No. 4,057,725; U.S. Pat. No. 4,196,352; U.S. Pat. No. 4,220,863; and U.S. Pat. No. 4,203,036. However, no known prior art system teaches the use of an arrangement of detectors and radiation sources to calculate necessary dimensional data on-line in a manufacturing process.

SUMMARY OF THE INVENTION

In accordance with the invention, a tomographic apparatus is provided which is adapted for generating a reconstructed image and the dimensions of a planar section of a product which is movable along an axis of inspection. The apparatus includes at least one, and preferably three fan-shaped radiation sources, e.g., γ-rays, aimed at a planar section of the product, adapted for generating radiation at a level sufficient to penetrate the product, i.e., at least about 500- KeV, preferably at least 660 KeV, revolvable about said product in said plane, and adapted to scan said product plane at said axis. A stationary ring of radiation detectors is arranged so that the detectors are equally, i.e, equidistant from the center-line at all points, spaced around the product planar section outside of a radiation source scanning circle, and each of the detectors are adapted to provide an output which is a function of radiation absorption by the product, and consequently by the detector, in the scan plane. Computing means responsive to the radiation detector output signals is provided associated with the detectors for reconstructing the product planar image and calculating the product dimensions by detecting its edges. This is done by digitizing and assembling the signals from the detectors. Display means is also associated with the computing means and is responsive to the computing means for displaying the product's reconstructed planar image and dimensions.

In a more specific embodiment, the computing means is also adapted to generate weight-per-unit length, i.e., weight-per-foot values from known product density values and to provide such information for process control purposes.

In still another aspect, the invention comprises a method determining a product's planar dimensions and weight-per-unit length by a tomographic inspection with γ-rays. More particularly, in a preferred embodiment, three γ-ray sources are revolved about a product object within the same plane to penetrate said object in said plane with a fan-shaped beam of γ-ray radiation. A circular array of detectors are positioned in the same plane outside the γ-ray sources. The radiation is detected from said sources passing through the product object, and based on the radiation detected, computing means determines the dimensions of the product, and/or the weight-per-unit length thereof.

In order to increase weight-per-unit length and dimensional measurement accuracy, the detector data are compensated, (at each point in the fan beam), for system electrical offsets and individual detector gain characteristics. This compensation arrangement includes direct measurement of the offsets, and considers the effect of sample interval time on the measurement.

DETAILED DESCRIPTION OF THE INVENTION

General Operation and Theory

Figure 1A:
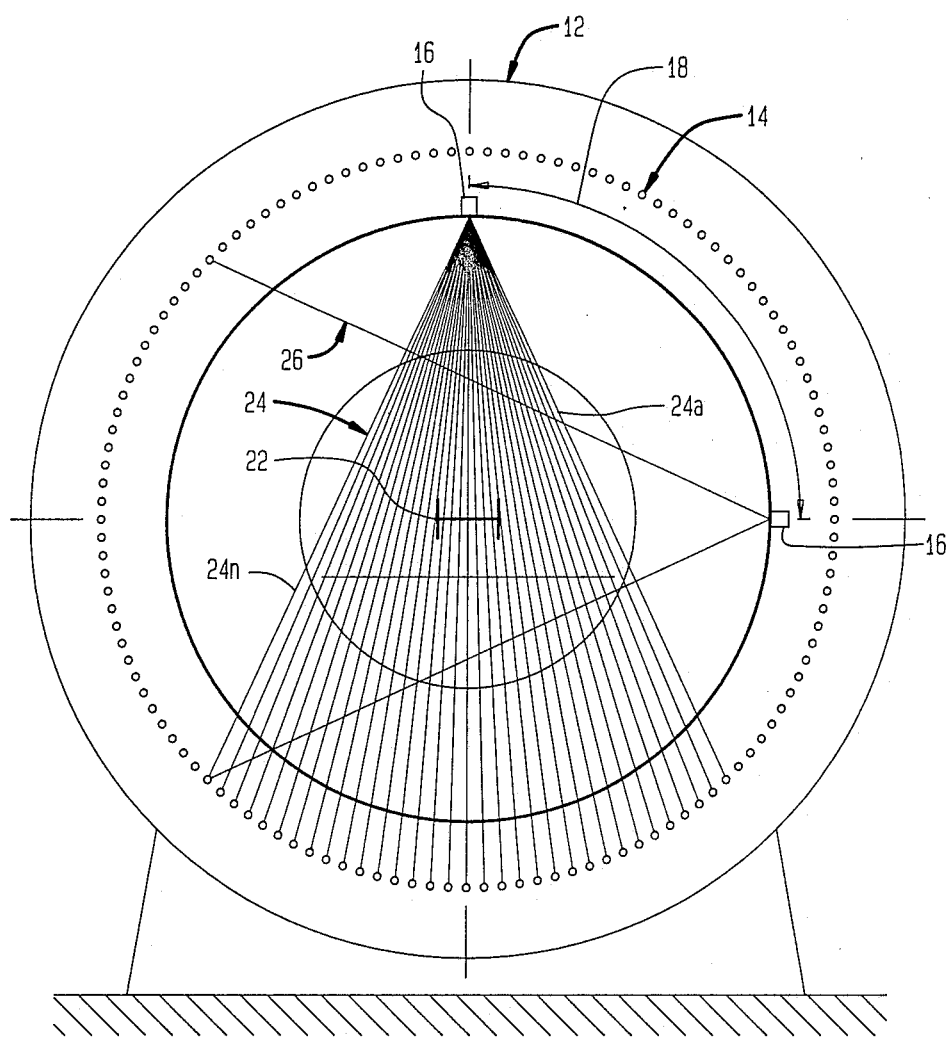
FIG. 1A is a cross-sectional view of the tomographic scanner for generating dimensions and weight measurements of an object passed along the axis of inspection according to the invention.

Referring now to FIG. 1A, there is shown scanner 12, which comprises at least one gamma radiation source 16 and a circular array or ring of gamma radiation detectors 14 which are arranged in the same plane as gamma radiation source 16.

Gamma radiation source 16 projects a fan-shaped beam 24 along a plane perpendicular to the longitudinal axis of an object 22 under scan. Source 16 generates radiation of at least 650 KeV, sufficient to penetrate inanimate object 22 such as steel beams. The preferred embodiment of scanner 12 is designed to operate in a steel mill in sequence with the completion of the rolling process of steel objects such as I-beams. The I-beam, which may be produced by the rolling mill in lengths of eighty to two hundred feet may be scanned and accurately measured by scanner 12 to determine whether dimensional tolerance is within specification and to determine the weight per unit length, e.g. weight per foot, averaged over the entire length of the beam.

The radiation produced by gamma radiation source 16 is detected by detectors 14. To enhance resolution, a substantially large number of detectors 14 is used. For example scanner 12 may include one hundred twenty eight detectors 14. Detectors 14 detect fan-shaped beam 24 made up of fan rays 24a-24n, with the intensity of each fan ray (24a-24n) or element varying according to the medium through which the fan elements 24a-24n pass. For example, a fan ray 24a-24n passing through air has a much greater intensity than a ray 24a-24n which passes through object 22. This is due, in part, to scatter effect 32 (FIG. 3) which is caused by a deflection of the radiation particles by the object being radiated and the absorption of radiation when passing through material of substantial density.

During scanning, source 16 rotates along path 18 constantly emitting radiation. At each instant during the rotation, a snapshot taken by detectors 14 is produced and transmitted to a computer 114 (FIG. 1B) to determine the radiation intensity received by each detectors 14 from source 16 at that instant.

Path 18 traveled by source 16 extends completely around object 22 inside the circle defined by detectors 14. In this way there is presented a complete image of the object 22 being scanned. At the same time, object 22 moves along a transport means, such as a conveyor belt, (not shown). The effect of rotating source 16 in the plane of detectors 14 together with the travel of object 22 in a longitudinal direction perpendicular to the plane of detectors 14 produces a helical image of object 22. This helical image is then compressed to provide a cross-sectional representation of object 22.

Figure 1B:
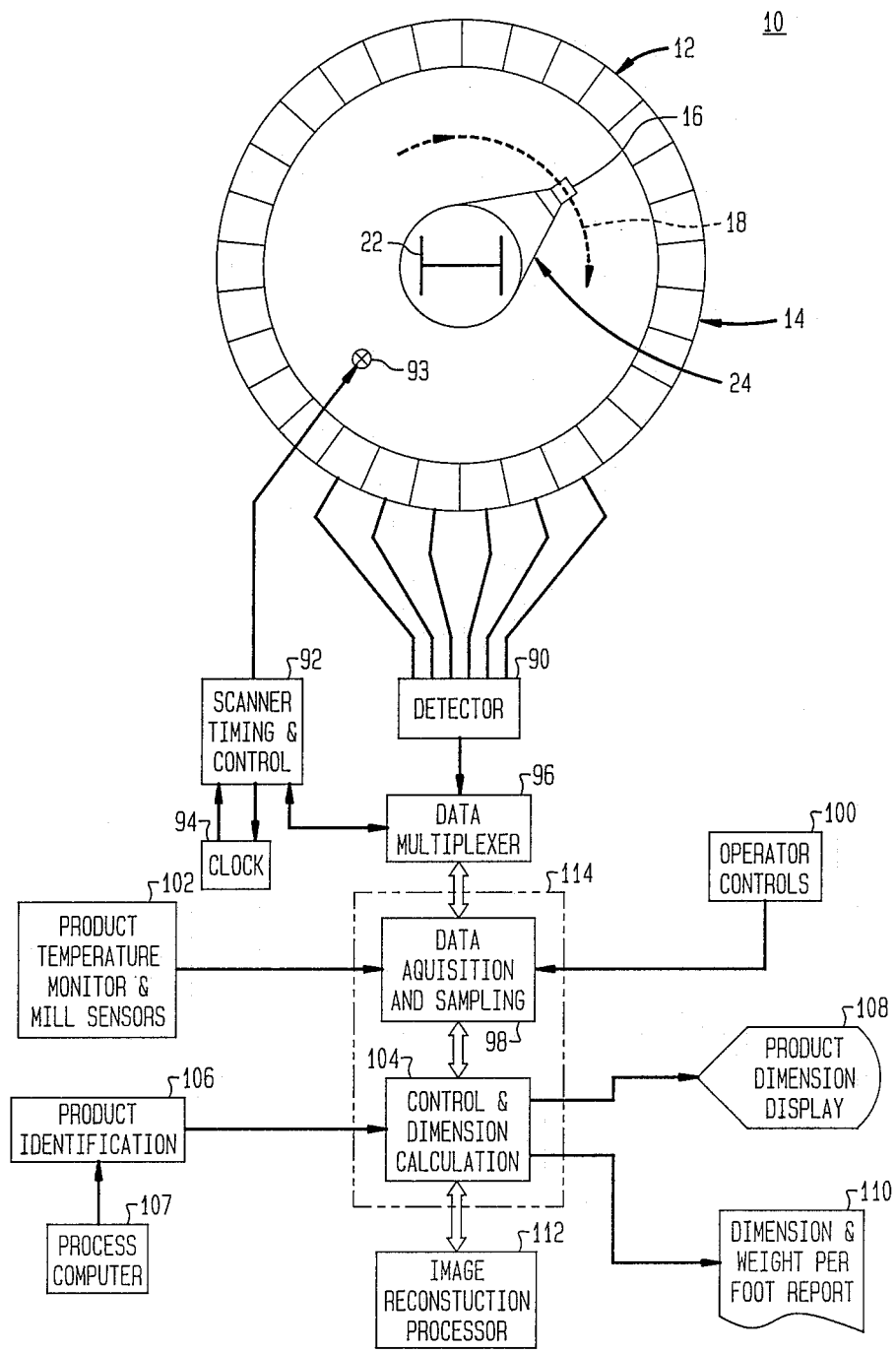
FIG. 1B shows, in functional block diagram form, the scanning system of FIG. 1A.

FIG. 1B shows in functional block diagram form scanning system 10 including scanner 12. Each detector 14 is coupled to detector assembly 90. The position of radiation source 16 is transmitted to scanner timing and control block 92, coupled to encoder 3, in whi39ch the location and the time of each scan is recorded in accordance with a clock signal from a clock 94. The information from timing and control block 92 and detector assembly block 90 are applied to data multiplexer and digitizer 96 which places the information in a form and sequence readable by computer 114 which includes data acquisition and sampling block 98 as well as control and dimension calculation block 104.

Temperature is monitored by product temperature monitor and mill sensor block 102. The temperature readings of block 102 are applied to computer 114 to account for variations in physical properties due to varying temperatures. Also applied to data acquisition and sampling controller block 98 is information from operator control panel 100. The information from control panel 100 is then transferred from block 98 to the control and dimension calculation block 104 where a determination is made of (1) the ideal dimensions of object 22 to be compared and (2) the actual dimensions of object 22 being scanned. The ideal dimensions of object 22 are stored in product identification block 106.

The ideal dimensions, received by way of block 106, as well as the actual dimensions of object 22 are then applied by block 104 to product dimension display 108. Display 108 shows the dimensions of object 22 for each of two scans that are run by scanner 12 of system 10 on object 22 as well as an average of the information from both of these scans. Also applied by control and dimension calculation block 104 is the dimension and weight per foot. The dimension and weight per foot is applied by block 104 to block 110 to show the amount of material that is being rolled into object 22. Complete image reconstruction is not essential since all relevant information has been gathered by determining selective coordinates along the boundaries of object 22 and using this information to determine deviations from an ideal and whether the deviations exceed the tolerance specifications. However, in another embodiment of the invention, the information from computer 114 may be applied to image reconstruction processor 112 to generate a complete image of object 22 being scanned.

Figure 2:
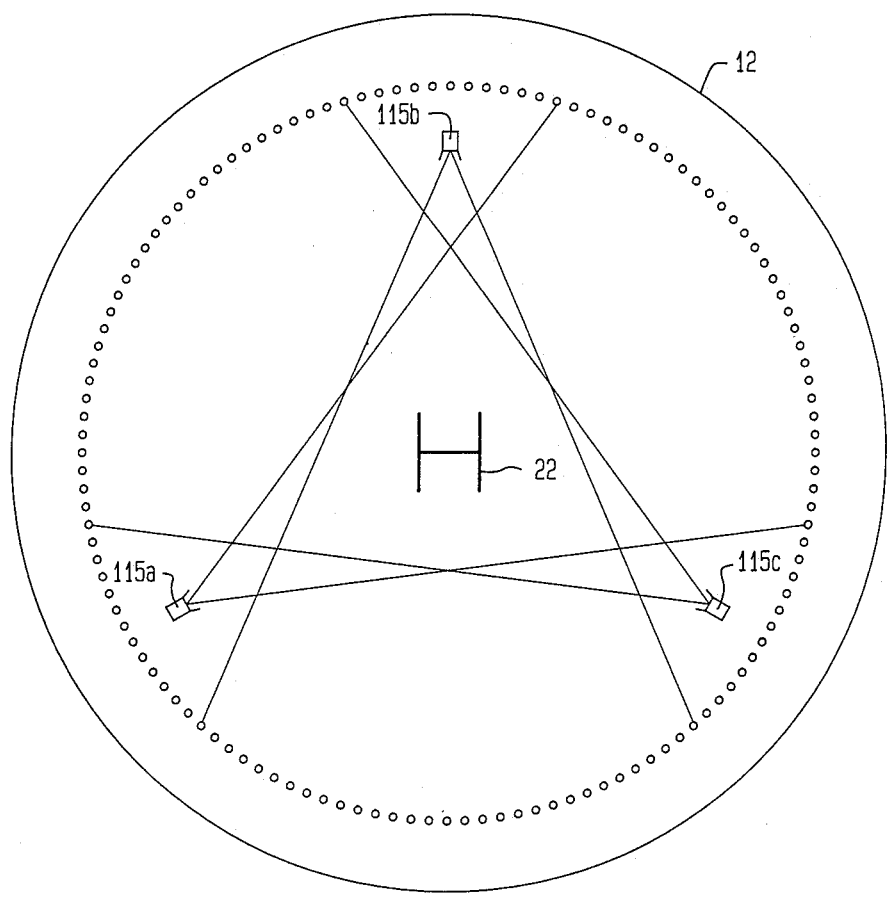
FIG. 2 shows alternate embodiment of the scanning system of FIG. 1, showing three gamma radiation sources instead of a single source.

FIG. 2 shows scanner 12a which is an alternate embodiment of scanner 12. Scanner 12a includes three fixed gamma radiation sources 115a, 115b, 115c, instead of a single gamma radiation source 16. The advantages of scanner 12a include a reduction in moving parts and a reduction in the possibility of failure in operation. Another advantage of scanner 12a is the ability to obtain a complete instantaneous imaging snapshot instead of a compressed helical representation. This lends itself to constant scanning of a single object 22 instead of the variety of objects 22 which may be effectively scanned by rotating source 16 of scanner 12.

Figure 3:
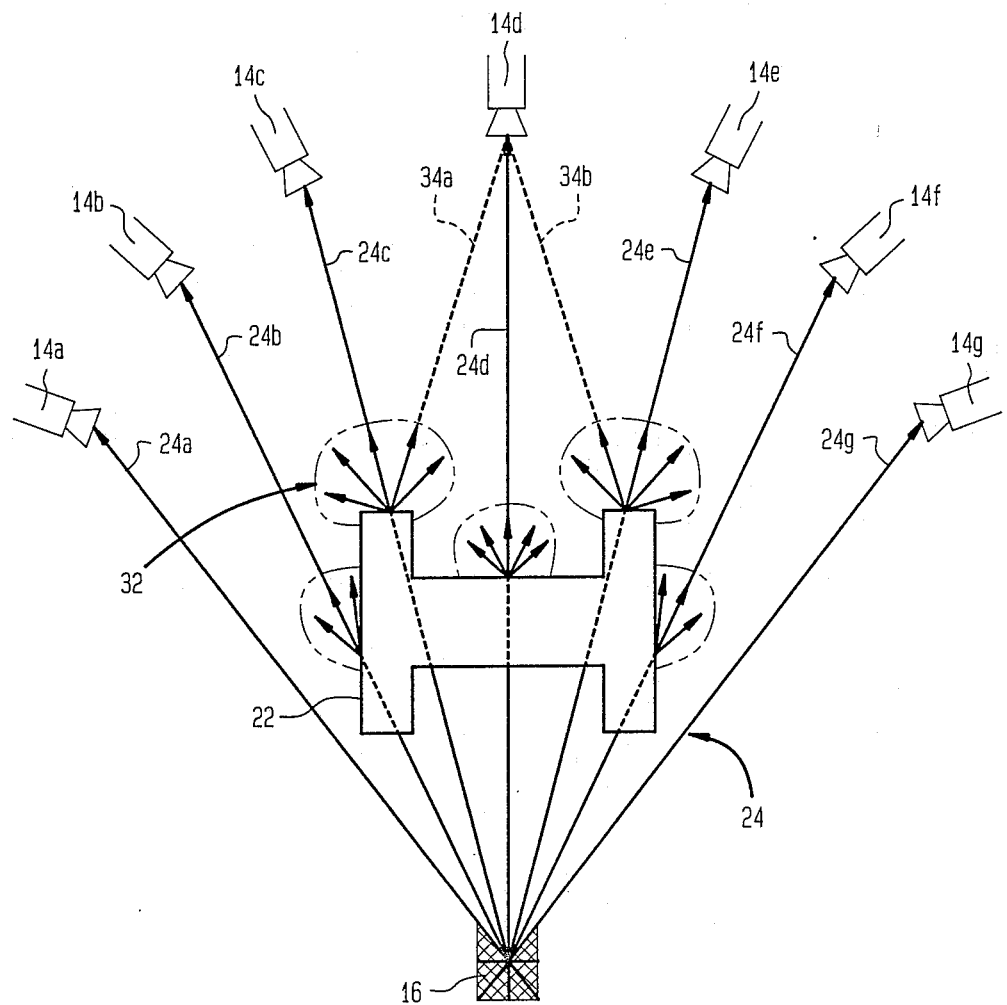
FIG. 3 shows an example of an object undergoing scanning by the scanning system of FIG. 1.

Referring to FIG. 3, for purposes of explanation there is shown an example of object 22 undergoing scanning by gamma radiation source 16 with detectors 14a-14n illuminated by fan beam 24. Each fan element 24a-24n intersects with respective detectors 14a-14n. In this example, fan elements 24b-24f intersect object 22 and produce a scatter effect 32. As already stated, a scatter effect 32 occurs when the gamma radiation particles are deflected by the object being irradiated or scanned. The scatter effect causes radiation to be detected by detectors 14 which would otherwise not be in the path of the fan element.

Scatter path 34a and 34b are illustrative of the increased radiation that a detector 14 such as detector 14d receives from fan elements other than the direct line of sight fan element 24d which would normally illuminate detector 14d. Other scatter paths are not shown but it is understood by those skilled in the art that multiple detectors 14a-n will pick up or detect the scattered radiation after a fan element passes through the object 22. This is often referred to as the Compton effect or Compton scatter effect. Readings from the detectors are processed to account for and correlate the information in response to these Compton scatter effects.

The ideal or model dimensions of object 22 being scanned are used to locate fan elements 24 near or at the point where the corners or outer boundary points of object 22 should be located. This is a preorientation of source 16 positions to approximate the location of object 22. It is the detection of the intensity of the radiation produced by gamma radiation source 16 which determines the location of object 22, because the varying intensities detected by detectors 14a-n provide information corresponding to the location of object 22. In order to determine the exact position of object 22 it is essential to establish at what point a first fan element 24a-n passes through object 22 in which the next adjacent fan element 24a-n fails to pass through object 22.

Figure 4:
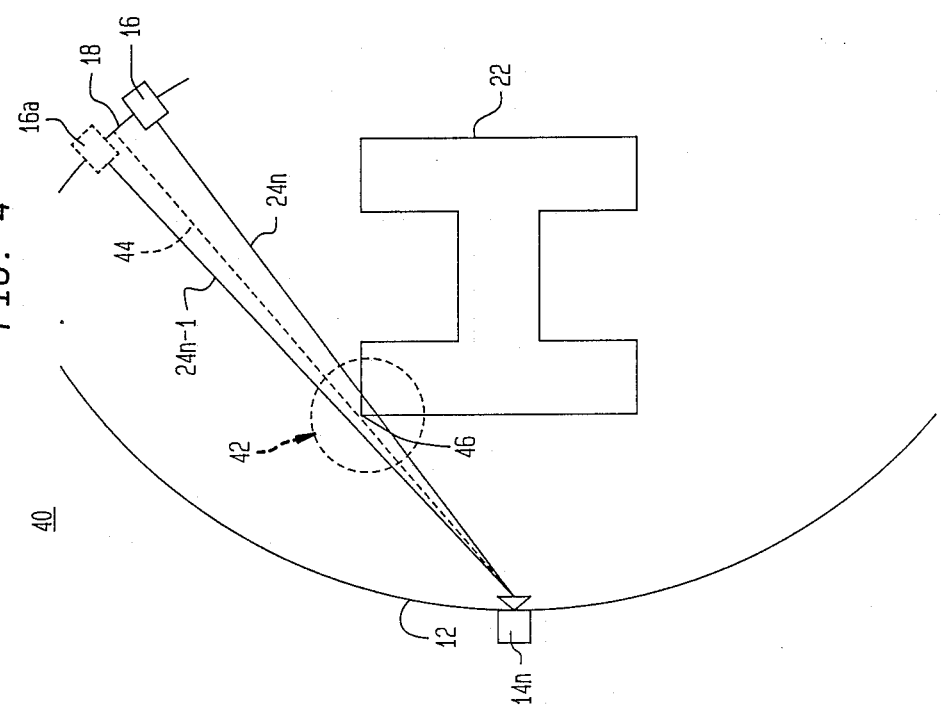

Referring now to FIG. 4, there is shown corner location process 40 whereby a fan element 44 is interpolated to a line intersecting a corner of object 22. This result is derived from fan element 24n which is determined to pass through object 22 and fan element 24n-l which is determined to not pass through object 22. These determinations are made in response to the intensity of the radiation detected by detector 14n. Fan elements 24n and 24n-l are detected by detector 14n as source 16 travels along path 18. Using the equations (which will later be given) for the fan elements or lines that pass through object 22 and those fan elements which do not pass through object 22, respectively, allows for the interpolation of a fan element 44 between the lines which intersect the corner of the object in question.

Figure 5:
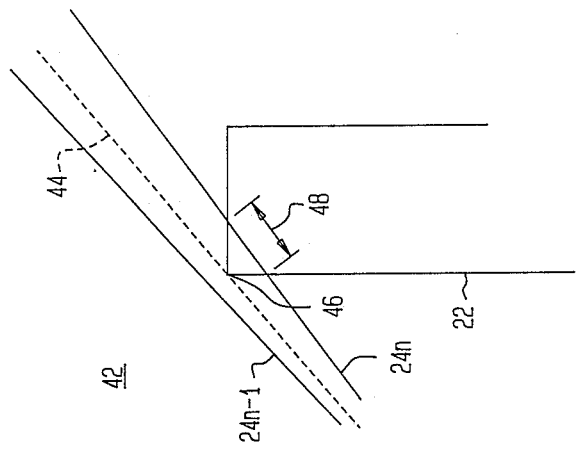
FIGS. 4-6 depict the corner location process for determining the corner coordinates of the object.

Referring now to FIG. 5, there is shown an exploded view of area 42 corresponding to the corner of object 22 and the fan elements 24n, 24n-l and interpolated fan element, or line 44. Distance 48 affects the intensity of fan element 24n passing through object 22 at that point which is the determining factor in establishing the outermost fan element which passes through object in the region of corner 46. The outcome of this process of corner location establishes an interpolated line which is tangent to point 46. This process is repeated as gamma radiation source 16 travels along path 18. By repeating the process, a series of interpolated lines tangent to point 46 are established and the intersection of said interpolated lines will provide the exact coordinates of point 46.

Figure 6:
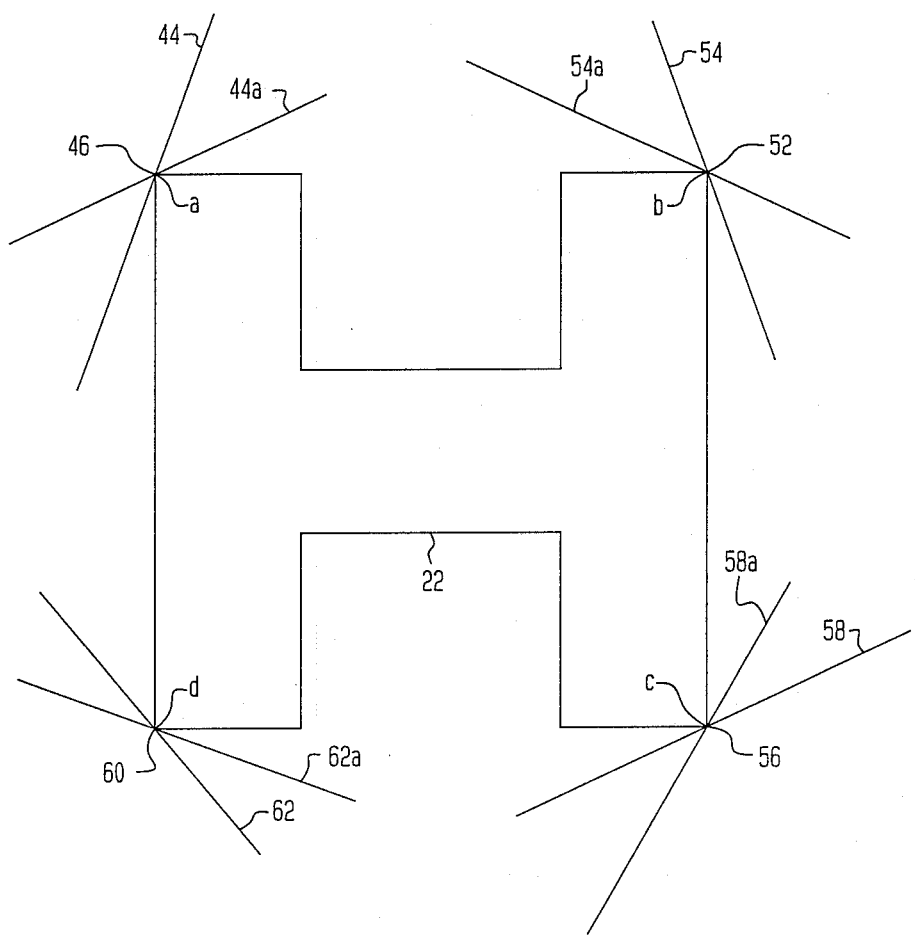

FIG. 6 shows the four sets of interpolated lines whose intersection provides the coordinates of respective corners 46, 52, 60 and 56. In the upper left-hand corner of object 22, the coordinates of corner 46 are established by determining the point of intersection of interpolated lines 44 and 44a. On the uppermost right flange of I-beam 22, the coordinates of corner 52 are established by determining the point of intersection of interpolated lines 54 and 54a. In the lower left hand corner of I-beam 22, the coordinates of corner 60 are established by determining the point of intersection of interpolated lines 62 and 62a. In the lower right hand corner of I-beam 22, the coordinates of corner 56 are established by determining the point of intersection of interpolated lines 58 and 58a. At the end of this process, the coordinates of all four outer boundary or outer corner points are established and recorded by scanner system 10.

Figure 11A:
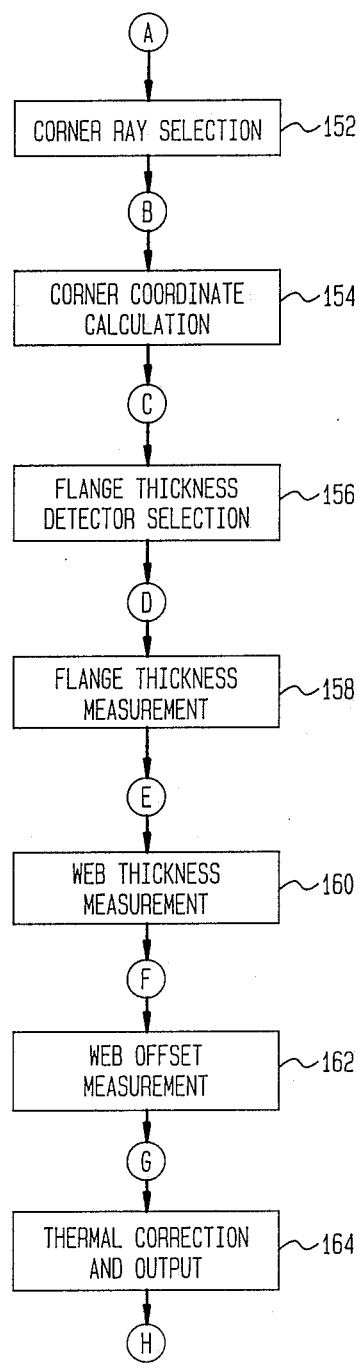
FIGS. 11A-N are flow diagrams depicting the software analysis for dimensioning an object using the scanning system of FIG. 1.

Referring now to FIG. 11A, there is shown flowchart 150, an overview of the dimensioning software which is written in Fortran for a Digital Equipment Corp. VMS Computer and which appears as Appendix A. This software is used to analyze an object 22. Block 152 provides for corner ray selection. Once the corner rays are selected, the coordinates of the corners of object 22 are determined in block 154. Block 156 uses the corner coordinates, determined in block 154, to select detectors 14 for the flange thickness measurement which takes place in block 158. Block 160 determines the thickness of the web section. Block 162 measures the offset of the web section and block 164 calculates a thermal correction based on the web temperature.

Figure 11B:
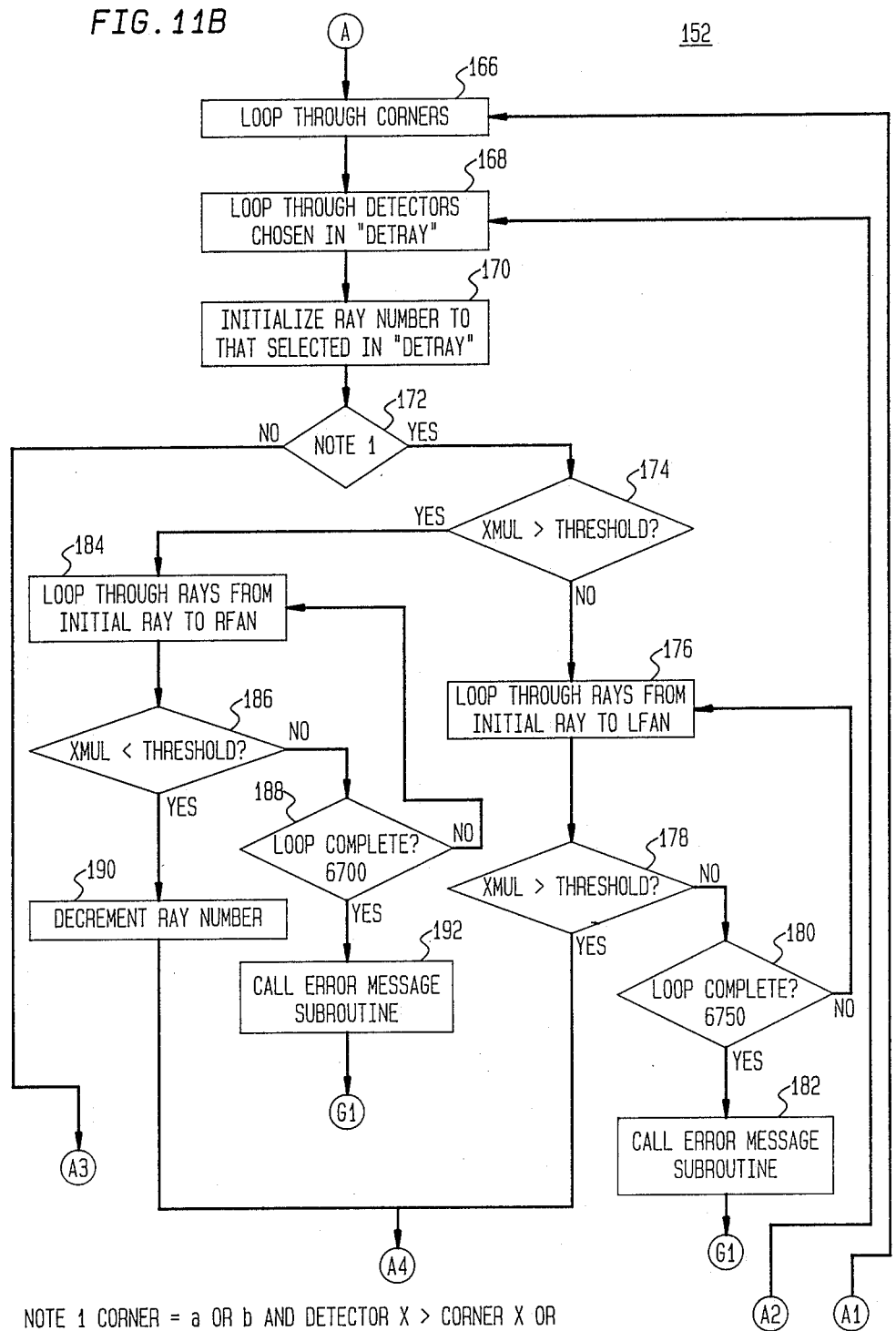

Referring now to FIG. 11B, there is shown flow diagram 152 of the corner ray subroutines of block 152 that are run in computer 114. Block 166, begins a process which loops through the corners of object 22 being scanned starting with corner a on the upper left-hand side through corners b, c and d numbered clockwise around object 22, as shown in FIG. 6. The purpose of the loop beginning at block 166 is to determine the equations of a number of lines that are tangent to the corners of object 22. Block 168 starts a loop through detectors chosen in preliminary sub-routine 560. These detectors were chosen such that they would have rays that passed through the corner but not through other parts of object 22 being scanned. The dimensioning routines assume an x-y coordinate system with the starting location for detector 14 being the origin of the coordinate system.

Block 170 initializes the ray numbers which are used in flow diagram 152. The ray numbers are those selected in subroutine 560 for each detector 14 selected in subroutine 560, one ray number for each detector. The rays selected are those that pass closest to each of the ideal corner locations of object 22 being evaluated. These rays are a starting point that allow processing to move optimally from the ideal corner position to the actual corner position as data from object 22 is processed.

Block 172 is a decision block in which a determination is made where the selected detector 14 is positioned relative to the corner positions. For example, for corners a and b which are on the top of an I-beam, if detector 14 is to the left of the corner then the ray numbers would increase moving toward the center of the section (FIG. 6). On the other hand, if the selected detector 14 were to the right of the corner, the ray numbers would decrease moving toward the center of the section. If the ray numbers decrease moving toward the section center, a "Yes" results from decision block 172 and processing moves on to decision block 174. In decision block 174 a determination is made whether the selected ray, as initialized in block 170, has a thickness value greater than a predetermined threshold value. The predetermined threshold is in the computer 114. If the thickness value is greater than the specified threshold value, the ray is assumed to pass through object 22. It is necessary to select rays further away from the center of object 22, i.e., with higher ray numbers, in order to find the corner.

When the answer to decision block 174 is "Yes", there is a thickness value greater than the threshold and execution moves to block 184. Block 184 begins a loop which sequences from the ray number that was initialized, as described above, to the maximum possible ray number for the scanner.

At block 186, a determination is made whether the thickness value of the current ray is greater than the threshold value. If the thickness value is greater than the threshold value resulting in a "no" decision in block 186, then the loop is repeated through block 188 and back to block 184 (where the ray number is incremented again) and then back to 186 where a check is once again made to determine whether the thickness value is below the threshold value. If it is below the threshold value, a decrement of one ray number is made in block 190 and control continues through off-page connector A4.

Referring now to decision block 188, a determination is made whether the loop is complete. Completion of this loop indicates the maximum ray number was reached. The maximum ray number, however, should never be reached. Therefore, if the loop is complete and the maximum ray number has been reached, then an error message is sent out as shown in block 192 and execution proceeds by way of off-page connector G1.

Referring now to decision block 174, if the thickness value for the initial ray is less than the threshold value then the selected ray does not pass through the corner and the ray numbers must be decremented in order to get rays closer to the center of object 22. This is done in block 176 which starts a loop where the rays move from the initial ray chosen to the minimum possible ray.

The loop including blocks 176, 178, 180 acts very much the same as the loop including blocks 184, 186, 188. First, block 178 checks whether the new ray number has a thickness value greater than the threshold value. If it does, then a corner has been detected and that ray is selected as both the ray passing through the corner and the ray closest to it. If the thickness value is still below the threshold value, then execution proceeds through block 180 and back to block 176. As in the loop including blocks 184, 186, 188 if the end of the loop is encountered (the extreme or minimum ray number), then an error has occurred and block 182 calls the error message subroutine and execution exits routine 152 via off-page connector G1.

Figure 11C:
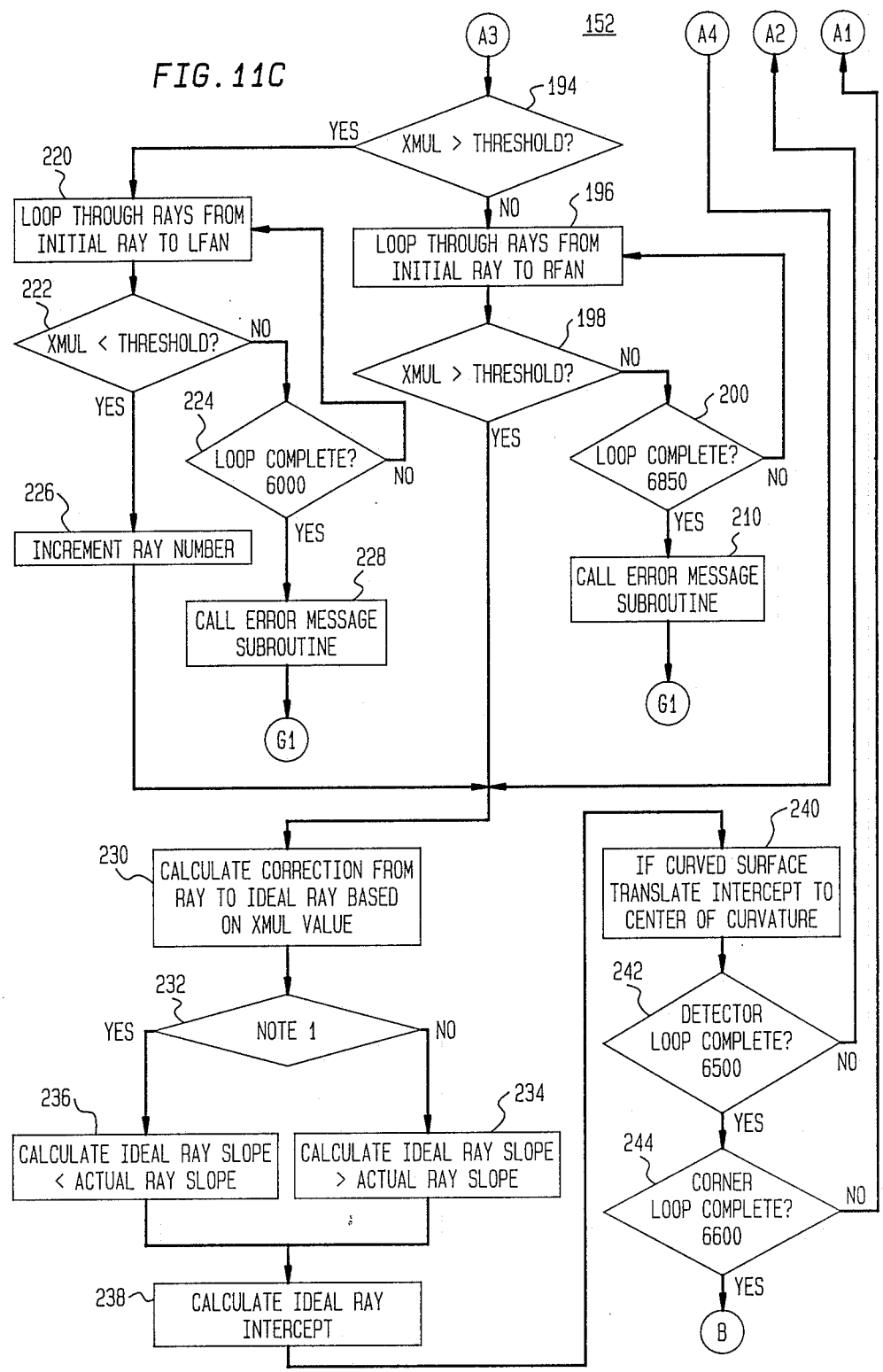

Taking the "No" path from decision block 172 means that if it is necessary to select rays closer to the object center, this can be done by increasing the ray number or move away from the object center by decreasing ray number. Processing moves through off-page connector A3 to decision block 194 (FIG. 11C). Again a check is made to determine whether the thickness value of the initial ray is greater than the threshold value as shown in decision 194. If it is, control moves to block 220 where a loop is initiated from the initial ray to the minimum possible ray. After the ray number is decremented, a determination is made whether the thickness value is less than the threshold value. If it is not, control moves through decision block 224 back to block 220, where the ray number is decremented and a check is made on the thickness value in block 222. Eventually, the thickness value will be less than the threshold value and a "Yes" results at block 222. Control then moves to block 226 where the ray number is incremented. This backs up one ray so that the current ray number is the one that passes through the corner and closest to it. Control moves to decision block 230.

If the answer at decision 194 was "No", the thickness value was less than the threshold value and logic flow moves to block 196 where a loop is initiated through blocks 196, 198, 200 to increase the ray numbers. The loop continues until the thickness is greater than the threshold value. When the thickness is greater than the threshold, control goes to block 230. Error handling in the loops of blocks 196, 198, 200 and blocks 220, 222, 224 are similar to the two loops previously described in that if the maximum or minumum ray numbers are obtained, a call is made to the error message subroutine in block 228 or block 210, depending on the loop, that outputs an error message to the operator and exit the routine via off-page connector G1. Thus all four of the routines just described tie into block 230. At this point one ray that passes through the corner and just adjacent to a corner has been selected for the current detector.

Now referring also to FIG. 4 and 5, there is a ray $24n$ that passes through the corner and the thickness value 48 for that ray is known. Furthermore, the position of the next ray away from the corner, that is, the previous ray $24n-1$ which does not pass through the corner is known. Thus a distance from ray $24n$ to the corner can be calculated based on the thickness value. The calculated distance is the perpendicular distance from the ray $24n$ passing through the corner to an ideal ray 44 tangent to the actual corner position.

In decision block 232 a determination is made whether the current detector 14 is to the right or left of the corner position. The purpose of doing this is because in the next two blocks, blocks 236 and 234, calculation is made of the slope of a new line (line 44 in FIG. 5) which passes through the detector and through the actual corner position based on the distance correction that was calculated in block 230.

Thus a determination is made in decision block 232 whether the slope of line 44 is greater than or less than the slope of the ray $24n$ that passes through object 22 and close to the corner. In flow block 236, or block 234, a calculation is made of the actual slope of this ideal ray 44 that passes exactly through the corner of object 22. In block 238 a calculation is made of the intercept of ray 44 using the slope of the ray calculated above. At this point, the full equation of the line 44 passing exactly through the corner of the object to the detector is known. Block 240 is not used in general in dimensioning I beams or wide flange sections but instead for objects with rounded corners. If the corner is rounded with a known or expected radius of curvature, a translation is made of the line previously determined that, in the case of a curved surface, would be tangent to that surface. This is translated towards the center of the section in such a manner as to have it pass through the center of curvature of the curved surface.

Next, in decision block 242, a determination is made whether all detectors 14 have been sequenced through for the particular corner that is being scanned. If "Yes", then control goes to decision block 244. If "No", control goes back to block 168 and the process is repeated for the next detector 14. If control moves to block 244, a determination is made whether all outside corners have been sequenced. If not, control goes back to block 166 and the process is repeated for the next corner. If all four corners are completed, then the control is taken via off-page connector B and the corner coordinate calculation routine 154 is initiated.

In routine 152, the rays which pass through the object very close to the corner for each detector 14 are determined and then an equation of a line that passes exactly through the corner of object 22 is calculated for each detector 14 and for each corner. Thus, approximately fifty to sixty independent lines have been determined which pass through each corner.

Figure 11D:
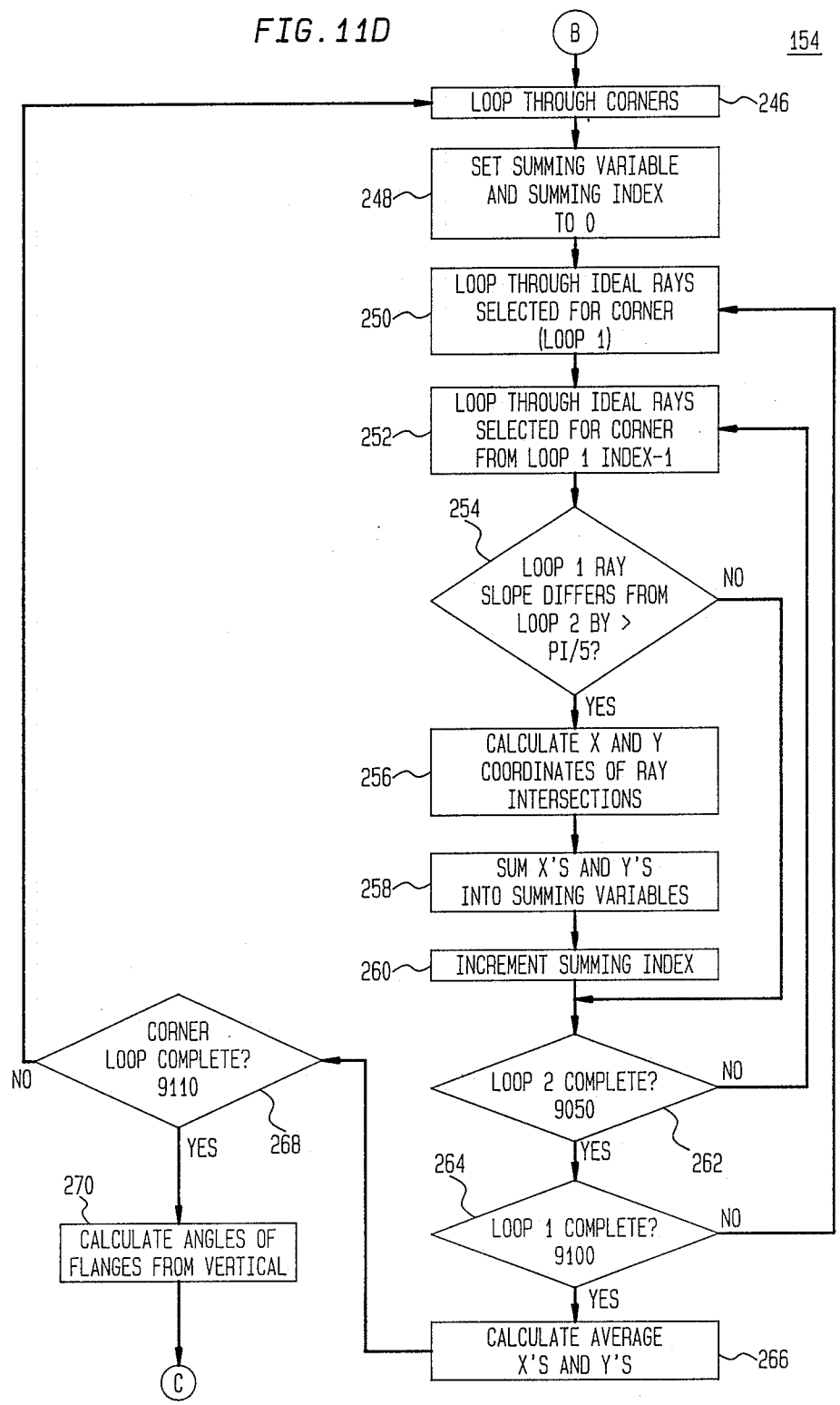

Referring now to FIG. 11D, in routine 154 the intersection points for pairs of these lines are calculated. Starting with block 246, a loop is initialized through the four corners. Moving on to block 248, variables are initiated to be used internally in this routine for averaging the corner coordinates. In block 250 loop 1 is initiated through the rays selected for the corner. In block 252, a second loop (loop 2) is initiated, sequencing through the same rays as block 250 so that there is a loop within a loop sequencing through these ray numbers.

In decision block 254, a determination is made whether the slope of the loop 2 ray, differs from the slope of the current ray in block 250 (loop 1) by a certain minimum amount. For the example, I-beam of FIGS. 4 and 5, 60 degrees is chosen as the minimum slope difference. Requiring that a minimum slope difference exist between lines whose intersection coordinates are to be determined both reduces the potential errors in the coordinate calculations and limits the number of solutions to a reasonable number. This means that the difference in slope between the lines must be at least a minimum value. If the slopes do not differ by at least 60 degrees, control moves to decision block 62 where if loop 2 is not complete, control goes back to block 252.

Block 252 increments the ray number and the next ray goes through loop 2. If, however, the slopes do differ by at least 60 degrees in block 254, control moves to block 256 where the x,y coordinates of the intersection of the two lines are determined. In block 258 the x coordinate and y coordinate are separately summed into running sums of the x's and y's determined for all of the intersections of the lines for this corner. In block 260, the summing index is incremented. In decision block 262 if all rays have not been incremented through, control goes back to block 254 and the process is repeated until the total number of rays for loop 2 is exhausted. At this point, control drops down to decision block 264 which checks that all of the rays for loop 1 have been incremented through. If not, control goes back to block 250 and the loops are repeated until all intersections) have been calculated.

Control then moves on to block 266 where the x's and y's for the line intersections summed in block 258 are averaged to determine an average x and y coordinate for the corner position. Control then moves on to decision block 268 where a determination is made whether all outer corners have been examined. If not, control goes to block 246 where routine 154 is repeated. If all outer corners have been examined, control moves ahead to block 270 and a calculation of the angles of the beam flanges from the vertical is made. This is used in a later routine as a correction factor when determining the thickness of the beam flanges.

Figure 11E:
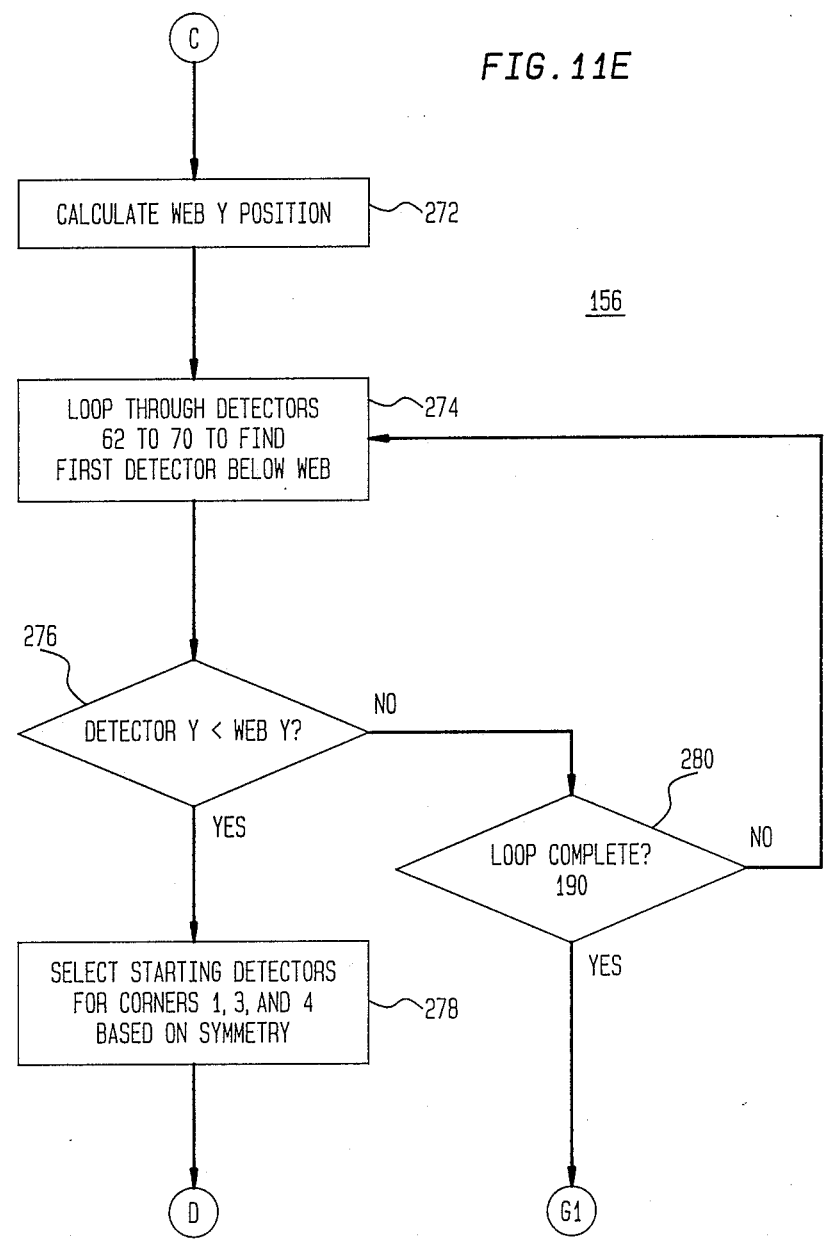

Referring now to FIG. 11E, there is shown flange thickness detector routine 156. The purpose of this routine is to select appropriate detectors that can be used for determining flange thickness for each of the four flanges (half flanges between the web and the four corners of an I-beam). The method used for this is to first determine the web position based on the corner positions known from routine 156. Then, for each flange, to select detectors which have rays that pass through that flange and through no other part of the object. Using corner 1 (upper left-hand corner in the present embodiment) as an example, detectors that are to the left of the section and which are below the web are selected. This process begins in block 272 by first calculating the web y position. Next in block 274, a loop is initiated through detectors 62 to 70 to find which of these detectors is the first to have its y coordinate below the y position of the web.

In decision block 276, a determination is made whether the detector y is less than the web y. If the answer is "No", control loops back to decision block 280 to determine if the loop is complete. Then, if not, control goes back to block 274 where the detector number is incremented and then back to decision block 276 to again determine whether the detector y is less than the web y position. Assuming that it is, the first detector on the right side of the section that is below the web is now determined. Detectors in this area may be used for measuring the flange thickness for the flange of corner 2 (upper right corner). The first detector that is actually used for the flange of corner 2 would be two detector numbers greater than that just determined as being the first below the web. That plus the next thirteen detectors in sequence would be used for measuring the thickness of the flange of corner 2.

In block 278, having determined the detector to be used for corner 2, and knowing the symmetry of both the gauge and object being scanned, a selection by calculation may be made of the first detector to be used for corners 1, 3 and 4. For example, the first detector for corner 1 would be in the range of perhaps 127 and the detectors then used would be 127 plus the next thirteen detectors in sequence in decreasing order, So it would be 127, 126, 125, etc. That completes the flange thickness detector selections and control moves to the flange thickness measurement loop.

In decision block 280, however, if all detectors are sequenced through and a detector has not been found below the web, an error condition has been encountered. When this error condition is raised, control exits from block 280 in the yes direction to off-page connector G1 to output an error message and to terminate the program.

Figure 9:
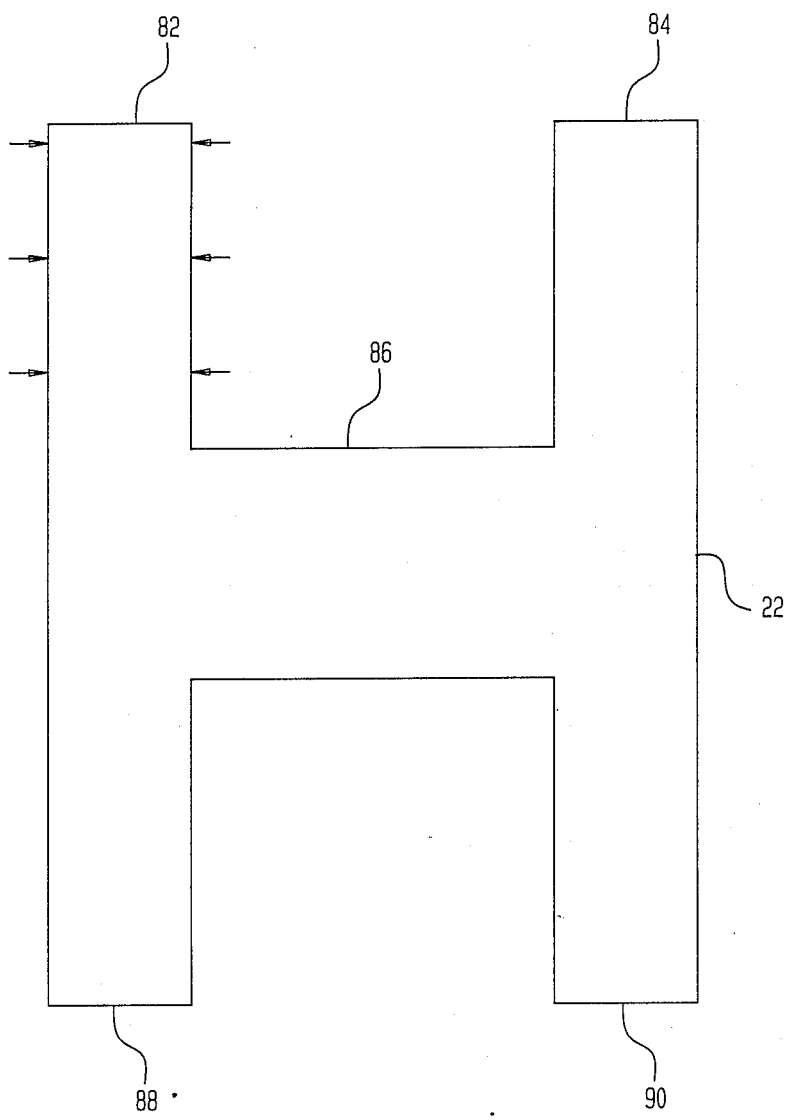
Figure 10:
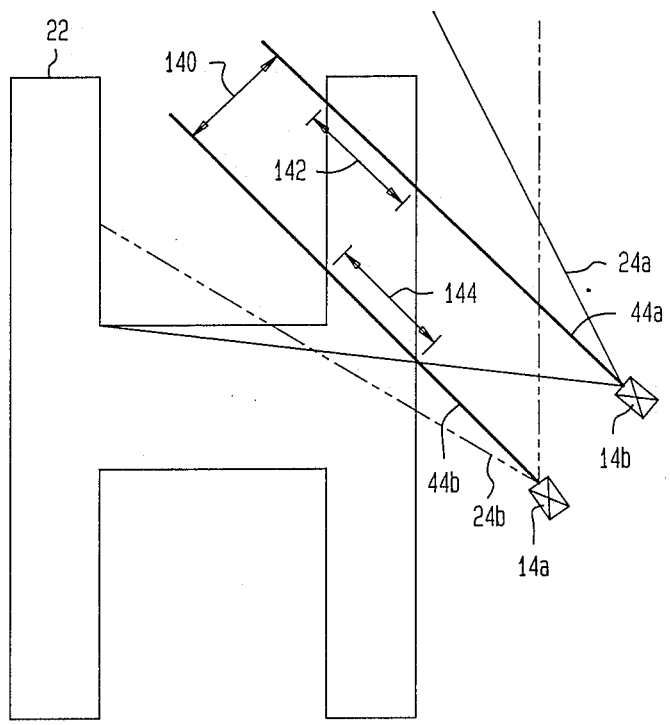
Figure 11F:
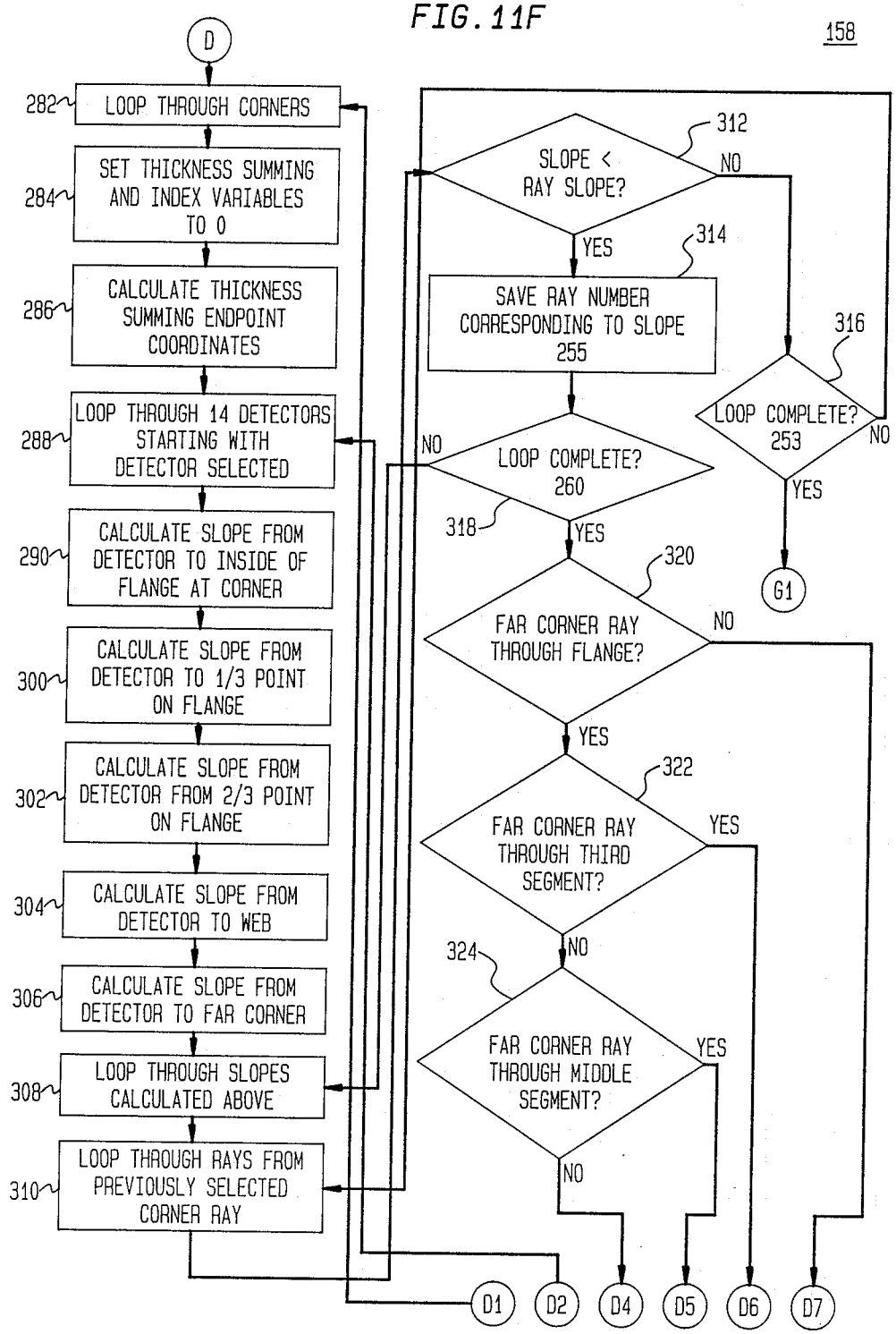

Referring now to FIG. 11F, there is shown flange thickness determination routine 158. In routine 150 the detectors 14 selected in routine 156 are used to determine the thickness of the flanges between the corner and the web of the section of object 22. This is accomplished by dividing the flange into three separate links as shown FIG. 9, and then summing the thickness values of the rays on the selected detectors 14 through each of those linked segments and finally taking the average values for each segment.

Routine 158 starts with block 282 which initiates a loop through the four corners of the section. Next is block 284, which initializes to zero the variables used for summing up the thickness values for each of the segments, as well as the index variables. In block 286, the x and y coordinates of each end of the three flange segments are calculated. This is done based on the previously determined corner location and the assumed web position. The segment end points nearest the corner end of the flange would be, for example, the corner coordinates determined in 154 translated a fixed distance toward the web so that the thickness summing does not see the corner of the section. If the reduced thickness at the corners were included in the flange thickness an error would be introduced into the thickness indication. Similarly, at the web end of the flange, the x and y coordinates of the web-flange junction are calculted and translated a fixed distance up the flange to determine that segment endpoint. Again the translation is done so that the increasing thickness seen at the web would not enter into the thickness summing for the flange thickness. The intermediate segment endpoint coordinates are calculated by interpolating between the now-known corner and web endpoints. Next, in block 288, a loop is initiated through the fourteen detectors chosen for the thickness summing for each corner.

Next, in block 290, the slope from the detector to the thickness summing endpoint near the flange end in block 286 is calculated. In block 300, the slope from the detector to a point one-third down the flange from the prior end summing point is calculated. In block 302 the slope to the two-thirds point on the flange and in block 304 the slope from the detector to the web end summing point on that flange are calculated, respectively.

In block 306, the slope from the detector to the inside of the far corner flange is calculated. In the case of the flange of corner 1, this requires a calculation in block 306 of the slope from the detector to the inside top of the corner flange. The purpose for doing this is to determine, whether the ray through any particular portion of the flange also passes through the flange of corner 2.

In block 308, a loop is initiated through the five slopes that were calculated in the preceding five blocks. In the loop, blocks 310, 312, 316 sequence through rays from a previously selected starting ray number to the maximum (or minimum) ray number. Since the detectors used for the flange thickness summing are a subset of the detectors that were used for the corner coordinate determinations, the starting ray for the 310–316 loop is the known ray that passes through the corner of the object. In the case of corner 1, the rays starting from that corner are sequenced towards the center of the object by increasing the ray numbers.

In decision block 312, a determination is made whether the slope of the ray is less than the slope of the line from the current detector to thickness summing endpoint that was calculated above. If the slope to the thickness summing endpoint is greater than the ray slope, the rays have sequenced past that endpoint and control goes to block 314. The ray number whose slope is closest to the slope of the line to the thickness summing endpoint is saved. If the ray slope is larger than the slope to the thickness summing in point, then the loop is repeated through blocks 316 to 310 and the ray number is incremented to the next ray number.

As in previous loops of this type, if the loop completes itself, that is if it increments up to the maximum ray number, then the loop is exited via off-page connector G1 and an error message is output to the control panel and execution is terminated. Thus the loop including blocks 308, 310, 312, 314, 316, 318 controls the process of determining the ray number closest to each of the thickness summing endpoints; the top, the one-third point, the two-thirds point and the web end point as well as to the far corner.

At this point, the ray number to each of those thickness summing points as well as the ray number to the far corner is known. In the next three decision blocks, 320, 322, 324, a check is made to see that the ray number to the far corner does not pass through the corner 1 flange. This is done by checking that the far corner ray number is larger than the web endpoint ray number. If it is determined that the far corner ray does pass through the flange, control goes to separate routines for summing up the thicknesses. The only differences between these routines are where the lower endpoint is. In the first case, where it was determined in decision block 320 that the far corner ray does not pass through the flange, control exits via off-page connector D7. On-page connector D7, leads into block 326 (FIG. 11G), where a loop is initiated through the rays from the upper endpoint ray to the ray representing the point one-third down the flange. In block 328, the thickness value for the current ray is summed into a summing variable. The thickness value is compensated for the fact that the ray is not perpendicular to the flange. In block 330, a summing index is incremented to correctly indicate the number of rays that have been summed for that thickness summing segment. Block 332 verifies that the loop is complete. If not, control goes back to 326 and the loop repeats itself until all rays have been summed between the top thickness summing endpoint and the one-third thickness summing in point. Blocks 334 through 340 perform a similar function for summing from the one-third thickness endpoint to the two-thirds thickness summing endpoint. Blocks 342 to 348 perform the same function for summing from the two-thirds thickness endpoint to the web end endpoint of the flange. Control then exits by off-page connector D8.

In block 320, a determination is made whether the far corner ray passed through the flange. If the decision is "yes", control passes to decision block 322, where a determination is made whether the far corner ray passes through the lowest thickness summing segment for the corner in question. The lowest thickness summing segment is between the two-thirds point on the flange and the web. If the ray passes through that segment, then control exits via off-page connector D6.

Figure 11G:
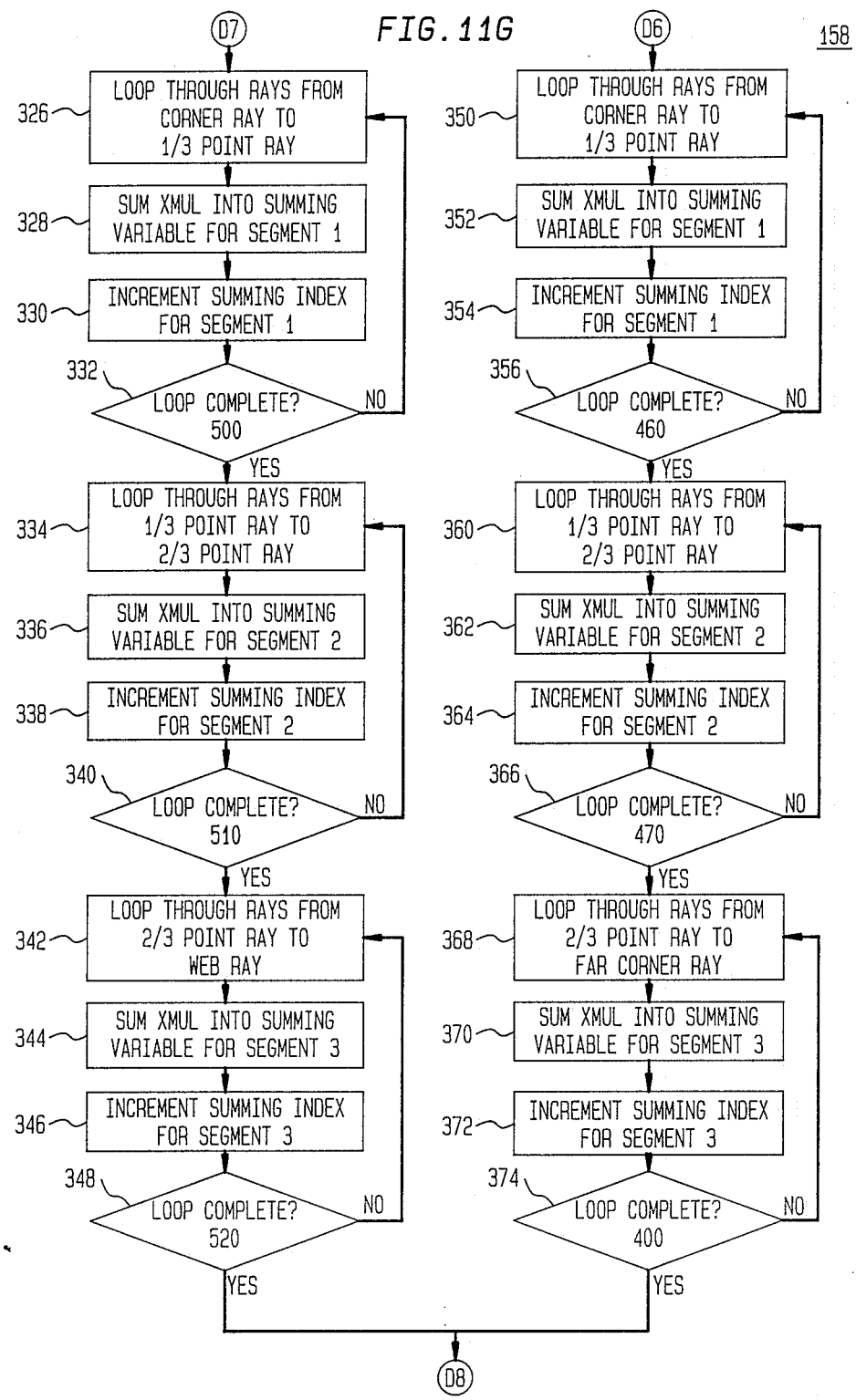

Referring now to FIG. 11G, execution proceeds from connector D6 to block 350. The routine from block 350 to block 356 sums through the topmost segment for the flange exactly as described for block 326 to block 332. Similarly, block 360 to block 366 sum the middle flange in exactly the same manner as described for blocks 334 to block 340. In block 368 to block 374, a sum is made from the two-thirds point ray. Instead of summing to the web-end ray, a sum is made down to the ray that goes to the far corner. Otherwise, the block 368 to block 374 loop is identical to the block 342 to block 348 loop. Execution then proceeds by way of off-page connector D8.

Returning to FIG. 11F, if a determination is made in block 320 and block 322 that the far corner ray both passes through the flange and does not pass through the third segment and if in block 324 a determination is made that the far corner ray passes through the middle segment, the control exits via off-page connector D5.

Figure 11H:
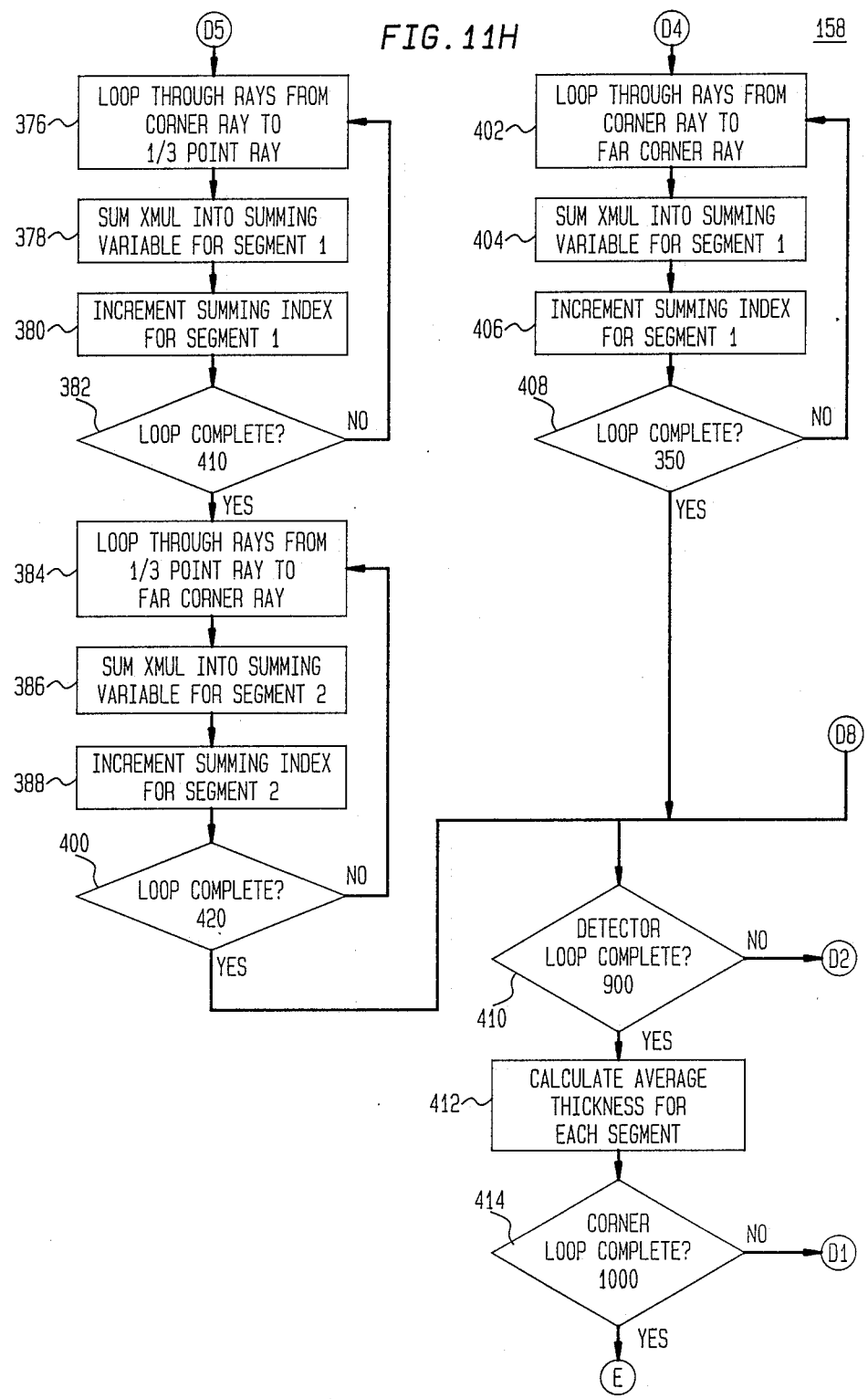

Referring now to FIG. 11H, execution may proceed by way of on-page connector D5, to a loop including blocks 376, 378, 380, 382 in which a sum of the upper segment of the flange is generated. This loop measures the thicknesses in the same manner as was described for the loop including blocks 326, 328, 330, 332. In the loop including blocks 384, 386, 388, 400, a sum is generated from the ray to the one-third point of the flange down to the far corner ray, in the same manner as that described for the loop including blocks 368, 370, 372, 374. If at decision block 324 it was determined that the far corner ray did not pass through the middle segment and control exited via off-page connector D4, then beginning with on-page connector D4 in the loop including 402, 404, 406, 408 a sum is generated for the top segment of the flange from the top endpoint down to the far corner ray similar to summing done in blocks 368 to 374.

Having completed all thickness summing, control moves on to decision block 410 which checks to see if all detectors have been sequenced through. If not, control goes back to block 288 to increment the detector numbers and to repeat the process. When the sequencing through all detectors for a corner has been completed, a calculation is made in block 412 of the average thickness for each of the three flange segments by taking the summed thickness and dividing it by the number of rays which were summed to obtain that thickness value. This results in three separate thickness values for each of the four corner-to-web flanges for the object 22. In decision block 414, a check is made whether sequencing is complete through each of the four corners. If not, control goes back to block 282 where the corner numbers are incremented and the process is repeated. When the corner loop is complete, control exits via off-page connector E to the web thickness measurement routine 160.

Figure 11I:
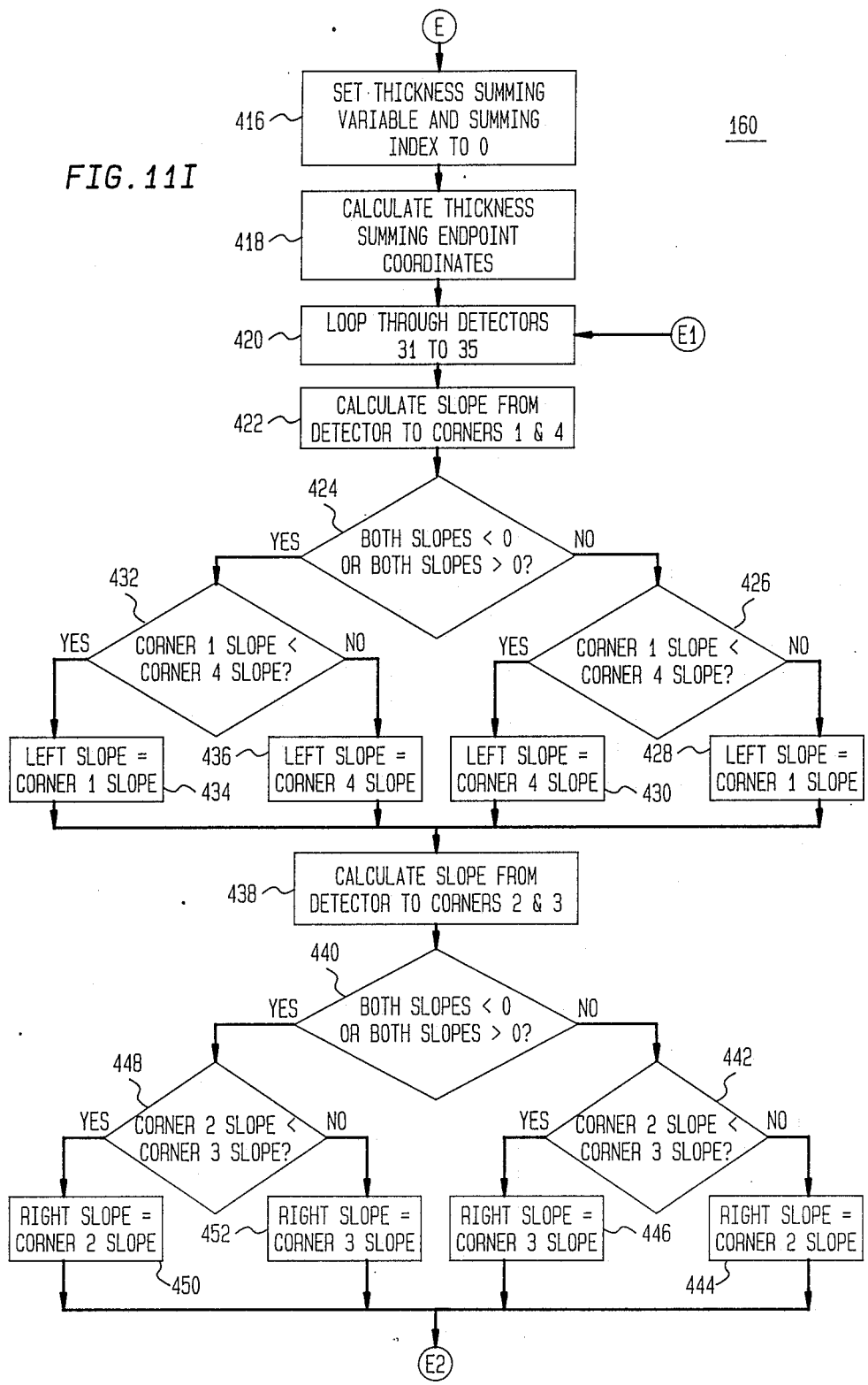

Referring now to FIG. 11I, there is shown the web thickness measurement routine 160. In this routine 160, as for the flange thickness summing, the web is divided into three separated but equal segments. Detectors 14 immediately above the section, (that is detectors 31 to 35) are then used to sum the thickness through each of three segments and to average them to determine the three thickness values.

Starting at on-page connector E, which leads into block 416, the thickness summing variables and the summing index are set to zero. Next, in block 418, a calculation of the nominal x and y coordinates for the expected thickness summing endpoints on either end of the web is made. In block 420, a loop is initiated through the five detectors 31 to 35. In block 422, the slope from the current detector to the inside edge of the flange at corners 1 and 4 are calculated. In block 424, a check is made of both slopes just calculated. This check in block 424 is to determine whether both of the slopes are negative or both of the slopes are positive. If either condition exists, control exits decision block 424 to decision block 432 where a determination is made whether the corner 1 slope is less than the corner 4 slope.

If the corner 1 slope is less than the corner 4 slope, control passes to block 434 where the corner 1 slope is chosen as the slope to the left end summing point of the web. If the corner 1 slope is greater than the corner 4 slope as determined by decision block 432, control moves to block 436 where the slope to the left end summing point is selected as the corner 4 slope.

Similarly, if in decision block 424, it had been determined that both slopes did not have this same sign, then a determination is made in decision block 426 whether the corner 1 slope is less than the corner 4 slope. If so, then in block 430, the slope to the left summing end point is set equal to the corner 4 slope. If in decision block 426, it is determined that the corner 1 slope is greater than the corner 4 slope, the left summing end point slope is set equal to the corner 1 slope in block 428. Then in block 438, a calculation of the slopes from the current detector to corners 2 and 3 similar to that made for corners 1 and 4 is made.

Decision block 440 determines whether both slopes have either a similar sign or a different sign. If both slopes have the same sign, control goes to decision block 448 where a determination is made whether the corner 3 slope is greater than the corner 2 slope. If it is, in block 450 the slope to the right summing end point on the web is selected to be the corner 2 slope. If, in block 448, it is determined that the corner 2 slope is greater than the corner 3 slope, then block 452 selects the right summing end point slope of the web to be equal to the corner 3 slope.

If a determination is made in decision block 440 that the slopes do not have the same sign, then block 442 determines whether the corner 3 slope is greater than the corner 2 slope. If it is, block 446 sets the right summing end point slope to be equal to the corner 3 slope. If block 442 determines that the corner 2 slope is greater, then block 444 sets the right summing end point slope to be the corner 2 slope and control exits via off-page connector E2.

Figure 11J:
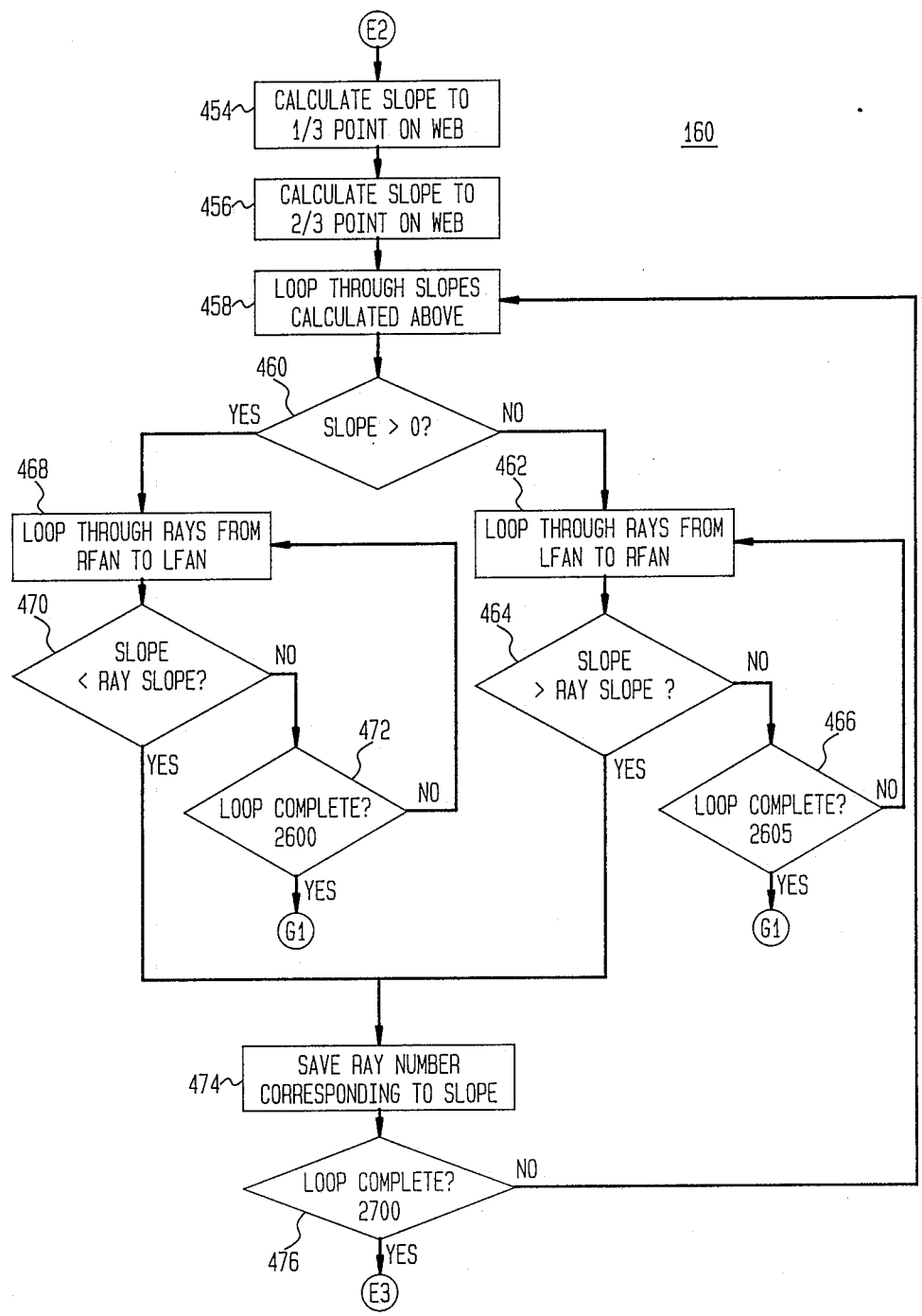

Referring now to FIG. 11J, on-page connector E2 moves control to block 454, which calculates the slope to the one-third point on the web. Block 456 calculates the slope to the two-thirds point on the web. Block 458 initiates a loop through the four slopes calculated. The four slopes are to the right summing end point, to the one-third point, to the two-third point and to the left summing end point.

In decision block 460, a check is made whether the current slope is greater than zero. If the current slope is greater than zero a loop through all rays from the maximum to the minimum ray number is initiated in block 468. Decision block 470 verifies that the current slope (to the summing point), is less than the ray slope. If not, then the loop is repeated, decrementing ray numbers, until it is determined that the ray slope is greater than the slope to the current summing endpoint. If it is, control exits to block 474.

If, in block 460, it is determined that the slope to the thickness summing point is less than zero, then control goes to block 462 where a loop is initiated through all rays for that detector, starting from the minimum ray going to the maximum ray number. This is different from the process of block 468 where ray numbers were decremented from the maximum ray number down to the minimum ray number. The purpose for doing this is to assure that the slope of the ray as the thickness point is approached will never be infinite.

In the loop including blocks 462, 464, 466, a check is made whether the current slope is greater than the ray slope. If it is not, the loop is repeated, incrementing the ray number until a ray slope is found that is less than the slope to the thickness summing point. At that point, control exits the loop to block 474 where the ray number corresponding to the slope is saved. Then decision block 476 verifies that the looping through the four slopes calculated has been completed. If not, the loop is repeated. If the loop is completed, control exits via off-page connector E3.

Figure 11K:
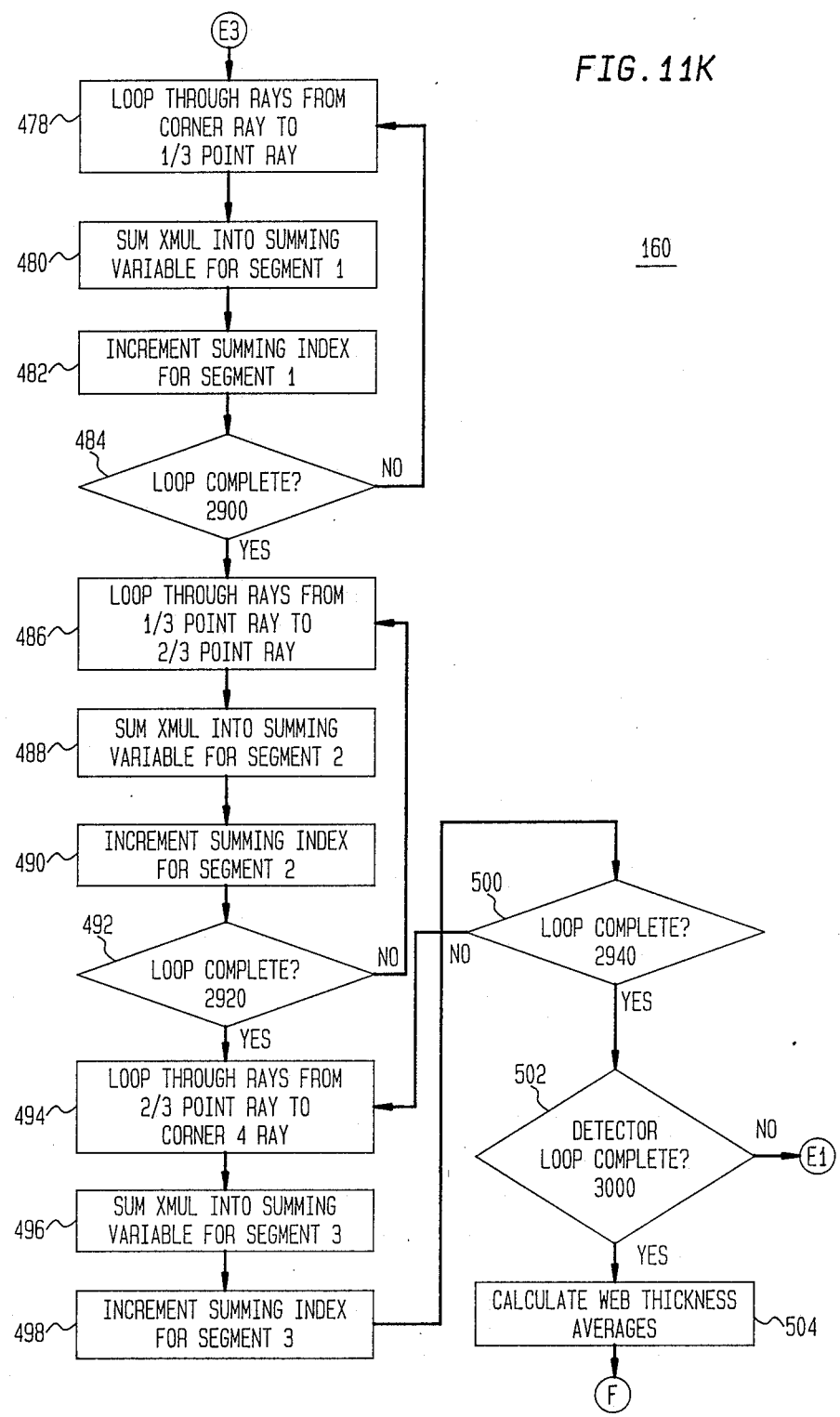

Referring now to FIG. 11K, on-page connector E3 leads to block 478 where a loop is initiated from the ray previously selected to the right endpoint to the ray to the one-third point. Incrementing through those rays in block 480, the thickness for each ray is summed into a summing variable. Block 482 increments a summing index and block 484 verifies that all rays in between the two end points are checked. Similarly, in the loop including blocks 486, 488, 490, 492 thicknesses for all rays from the one-third point on the web to the two-thirds point on the web are summed. The loop including blocks 494, 496, 498, 500 sum the rays from the two-thirds point on the web to the left-end summing point. A determination is then made in decision block 502 whether all five of detectors 14 have been checked. If not, control goes back to block 420 via connectors E1 to repeat the loop. If all detectors 14 have been checked, control moves on to block 504 where the thickness averages for each of the three segments is calculated by dividing the thickness sums for those segments by the number of samples represented in that sum. Processing then proceeds to web offset measurements, via off-page connector F.

Figure 11L:
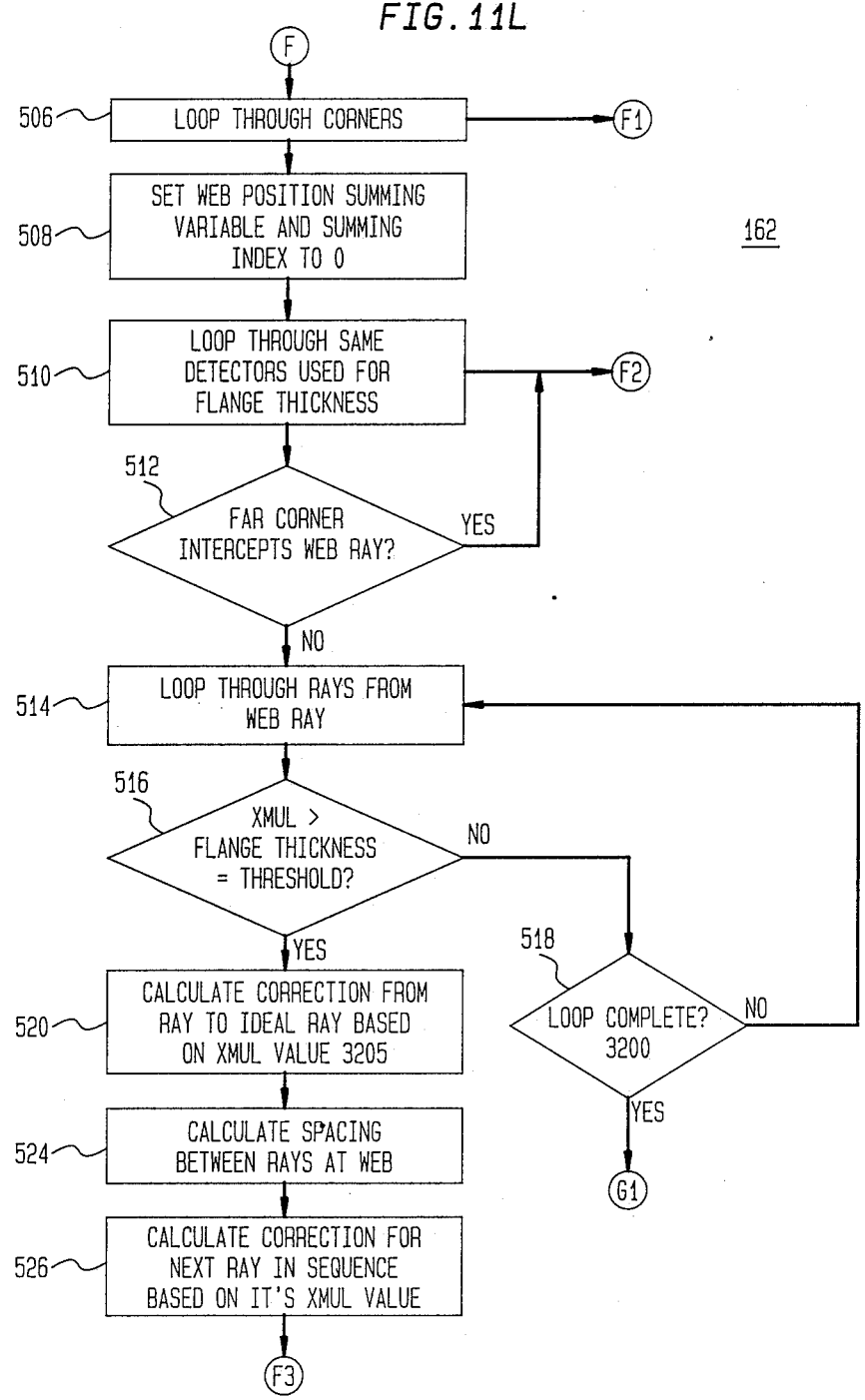

Referring now to FIG. 11L, there is shown web offset measurement routine 162. Routine 162 begins with on-page connector F which leads to block 506, where a loop is initiated through the four corners. In block 508, the web position summing variable and summing index are initialized to zero. Blocks 510, 512 initiate a loop through the same detectors 14 used for the flange thickness determination. In decision block 512, a determination is made whether the ray that was used as the low end point ray for the flange thickness summing intercepts the opposite side flange. Using corner 1 as an example, the ray is checked to verify that it does not intercept the corner 2 flange. If it does intercept the flange, control loops back to block 510 which increments to the next detector 14. If it does not intercept the corner 2 flange, then execution proceeds to block 514 which initiates a loop, starting from the lower end point flange thickness summing ray and incrementing ray numbers to move toward the web.

Figure 8:
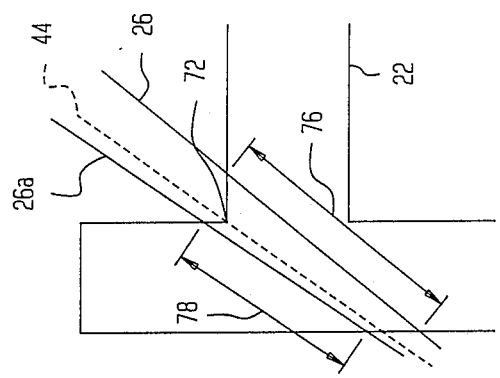
FIGS. 7-8 illustrate the process for determining the inner corner coordinates of the web of the FIGS. 9-10 are diagrams illustrating the process for determining the thickness of the flange of the object.
Figure 7:
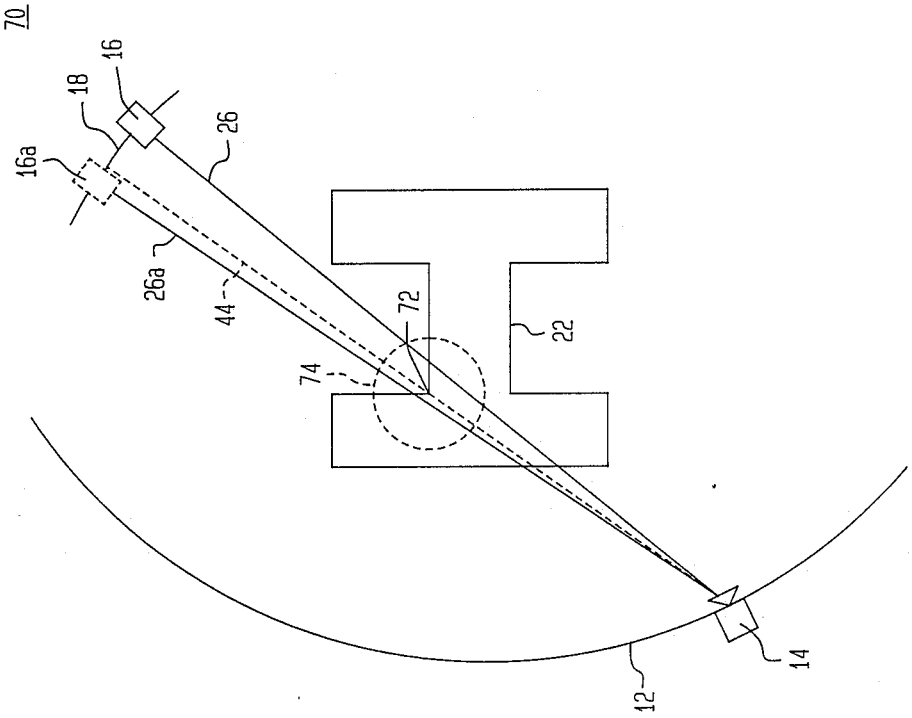

Block 516 checks that the thickness value for the current ray does not exceed the flange thickness plus an additional threshold value. An example of a ray that would not exceed the threshold is ray 26a in FIG. 7. A value exceeding the threshold would indicate a ray in the web area such as ray 26 in FIG. 7. If the thickness value does not exceed the flange thickness threshold, a loop through blocks 514–518 takes place incrementing through rays successively closer to the web. When the thickness value does exceed the flange thickness plus threshold value, block 520 calculates a correction from the ray position to an ideal ray that passes exactly through the web flange junction based on the thickness value (76 in FIG. 8).

This works in much the same manner as was done for determining the exact corner position in the prior routine 160. Block 524 calculates the spacing between the rays at the web, again in a similar manner as was done previously for the corners, and finally block 526 calculates a similar correction as was calculated in block 520 for the next ray in sequence based on its thickness value. Instead of using one ray as was used for the corner, two rays are used in sequence and the correction averaged. When the loop through blocks 514–518 is complete, control exits via off-page connector F3, which leads to block 528.

Figure 11M:
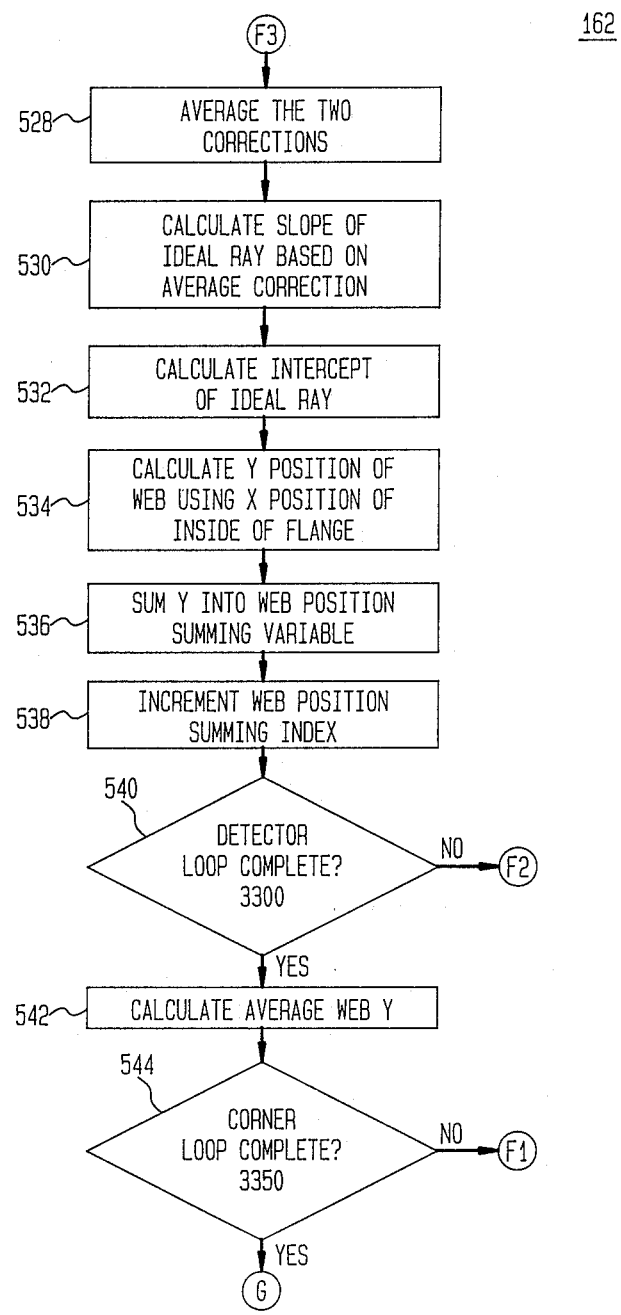

Referring now to FIG. 11M, there is shown routine 162. In block 528 of routine 162, an average is taken of the two corrections calculated in block 520 and block 526. Block 530 calculates the slope of an ideal ray, or line (44 in FIG. 8), through the web flange junction, based on the adjacent ray slopes that are known and on the calculated corrections. In block 532 the intercept for that line is calculated. In block 534 the y position of the web is calculated using the known x position of the inside of the flange and the line equation just determined in block 530 and block 532. In block 536, the y value just calculated is summed into a web position summing variable. A web position summing index which indicates the number of values in the summing variable is incremented in block 538.

Decision block 540 checks whether the loop has sequenced through all the detectors. If not, control goes back to block 510 via connector F2 to repeat this loop. If all detectors 14 have been through the loop, the average web y position is calculated in block 542 by dividing the web position summing variable by the number of values that have been summed into that variable. Finally, decision block 544 checks that each of the four corners has been through the loop. If not, control goes back to block 506 via connector F1 to repeat the entire loop. When all corners have been completed, control goes to the thermal correction and output routine 164 via off-page connector G.

Figure 11N:
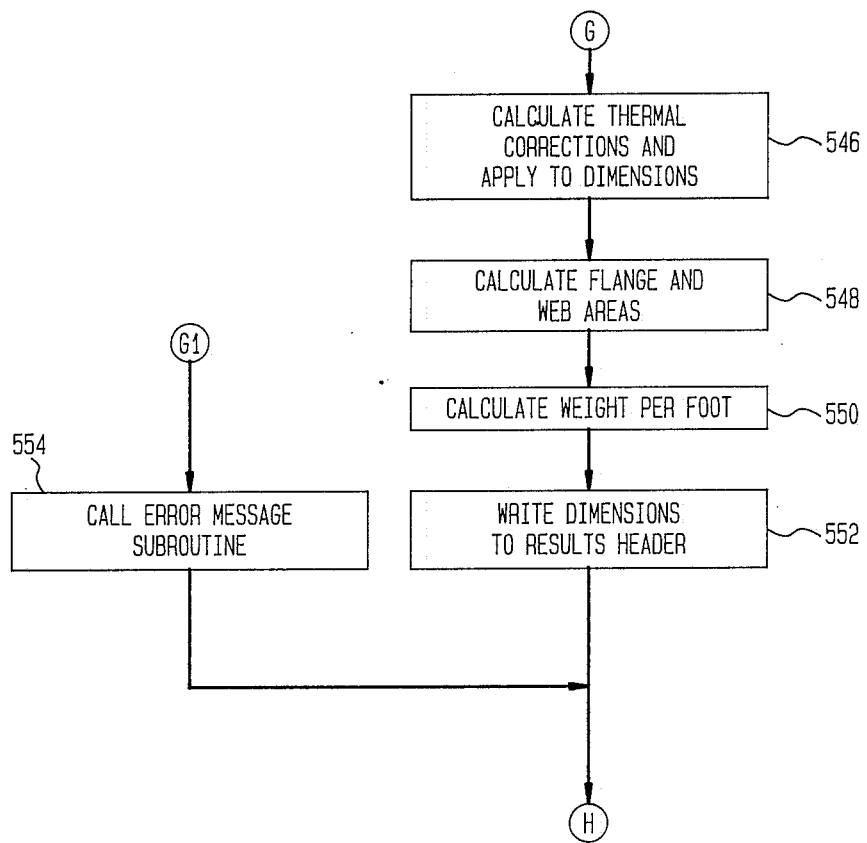

Referring now to FIG. 11N, there is shown the thermal correction and output routine 164. Routine 164 begins with on-page connector G which leads into block 546 where thermal corrections are calculated based on the measured web temperature of object 22. Separate corrections are calculated for thickness and for length, based on the web temperature. An additional offset temperature is added to the web temperature and applied to the flanges and separate thickness and length corrections are calculated for the flanges based on the web-plus-offset temperature.

Those corrections are applied to the x and y values for the corner dimensions as well as to the thickness values for the flange and the web. In block 548, the flange and web areas are calculated, based on the known corner positions and the known thicknesses of the flanges and the web. In block 550, the weight per foot is calculated based on the calculated web and flange areas. In block 552, the dimensions are written to the result header.

The error messages which are generated at various locations throughout the process come in via on-page connector G1 to block 554 which calls an error message subroutine. This error message subroutine outputs a message to the operator and terminates the routine at off-page connector H.

ERROR DETECTION

As was noted throughout the routines, there are numerous loops where summing occurs from one ray to either an upper or lower extreme ray. If control fails to jump out of the loop before the end point, then scanning has gone past the edge of the object and an error message routine is called which exits the dimensioning routine.

Another kind of error detection is also used in the corner ray selection loop of routine 152. This, in several cases, is substituted for the previously described error detection and error message routines. For each section tested by the gauge, a field of view of the gauge is defined for that section such that the section is expected to appear within that field of view (FOV). The FOV is defined by the ray numbers on either side of the fan beam. The FOV of the gauge is somewhat larger than the defined FOV for each section. This means that there are a number of rays on either side of the object that are not normally used for the thickness summing for tomography but are used for making corrections to the weight per foot calculations. Knowing the limits of the defined FOV when looking at the corners of the object in the dimensioning routine 152, it can be determined whether the position of the object being scanned is outside of the defined field of view for the section. If the object is outside the defined FOV, this will produce errors in the weight per foot summation. If the object appears to be out of the defined FOV it could indicate the need for a mill adjustment to reposition the object or it could indicate electronic problems or bad detectors in the gauge.

So, there are two kinds of conditions that might be detected. One, the object is not within the expected location within the gauge and two, there may be mechanical or electrical problems with the gauge itself. There are therefore four pieces of information that are collected within the corner ray selection routine 152. These are that the section is out of the normal field of view for a certain number of detectors at either the (1) left or (2) right side of the gauge or that some portion of the object appears to be outside of the field of view of the gauge (not just the defined field of view, but outside the total field of view of the gauge), on (3) one side or (4) the other, for some number of detectors.

Referring to routine 152, the code for determining whether the section is outside of the expected field of view is inserted between blocks 184 and 186. At that location, a check is made whether the ray number exceeds the defined field of view ray number for that particular object. If it does, a summing variable is incremented. The summing variable totals up the number of detectors for which the section is out of the defined field of view and also records which side of the gauge that occurs on. If block 192 is reached, it indicates that some portion of the object appears to be out of the total field of view of the gauge. Instead of initiating an error message, block 192 increments an index variable, which counts the numbers of detectors for which the object is out of the total field of view and on which siade of the gauge this occurs. Similarly, between blocks 220 and 222 of routine 152, a check is made to see whether the section is out of the normal, expected field of view. That information is summed into an index variable which indicates the number of detectors for which the gauge is out of the normal field of view and also on which side of the gauge this occurred. Likewise, in block 278 a summing occurs of the number of detectors for which portions of the section are out of the total field of view of the gauge.

In the case that the section is out of the total field of view of the detector, the routine continues rather than exiting, as was done previously at either block 192 or block 228. The routine continues, but the detector(s) for which the object appeared out of the FOV are not used for any further processing of the corner location. So, in the case where one or two detectors see the section out of the field of view, the corner postion can still be determined without exiting the routine. This presents valid dimensioning results even though (1) there may be a bad detector or (2) the object may be close to the edge of the gauge.

At the end of the corner ray selection loop the various summing variables (that summed the number of detectors for which the section was (1) either out of the defined the field of view or (2) out of the field of view), are looked at. Depending on the number of detectors that are summed, a flag is set to a specified value. The value of the flag indicates that the data is either valid or is invalid and an appropriate message indicating the number of detectors involved is output to the operator. The criteria used are that if the section was just out of the normal field of view, the dimensioning is considered to be valid and the appropriate message is output to the operator. If a portion of the section is out of the total field of view, for less than five detectors, an appropriate message is output and the dimensions are considered valid. If the section is out of the total field of view for five or more detectors, then the dimensions are considered invalid and an error flag is set and the routine is exited.

Figure 12A:
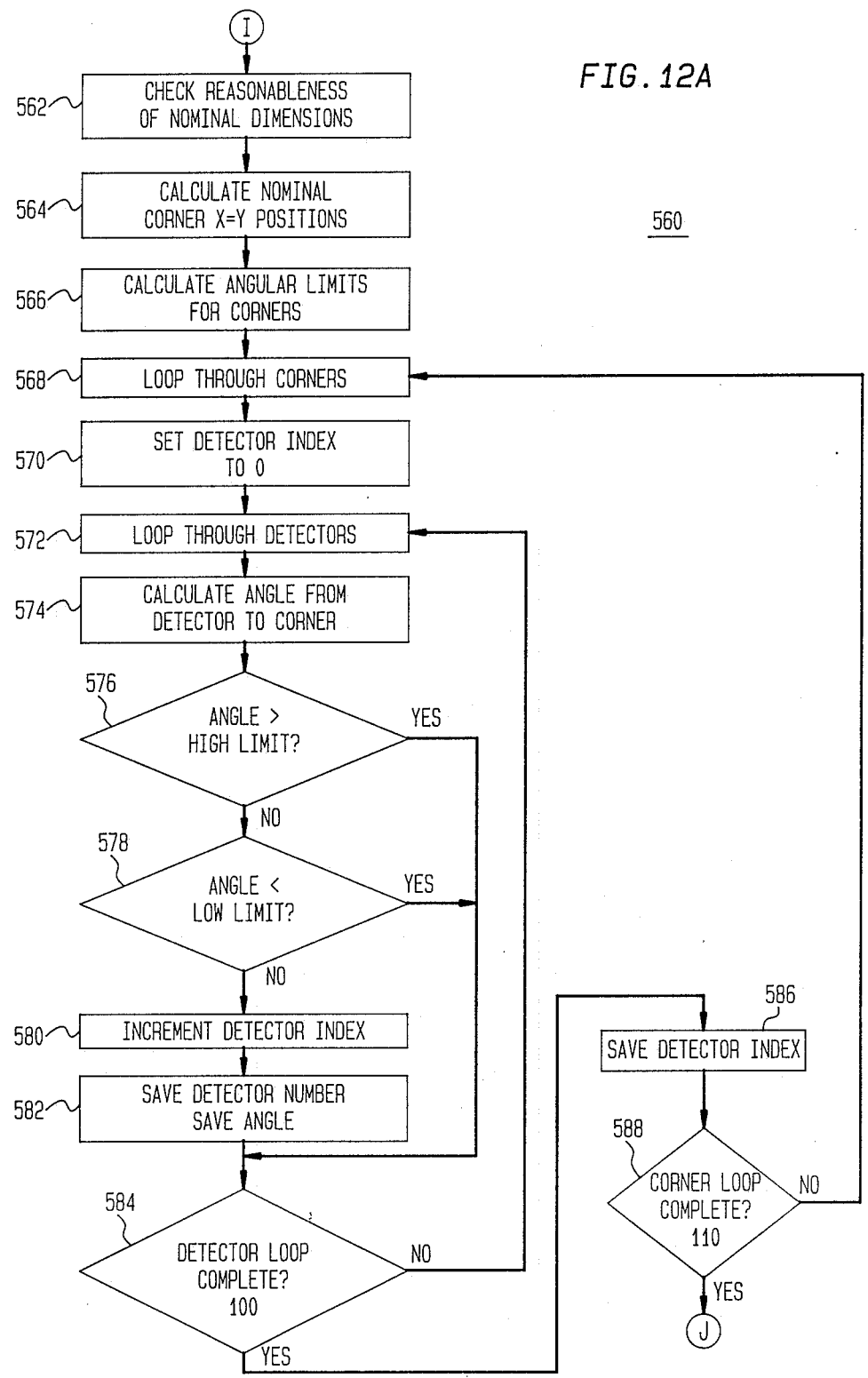
FIGS. 12A-B show a flow diagram of a sub-routine that calculates expected dimensions of an object to establish a starting point for the dimensioning routine of FIGS. 11A-C.

Referring now to FIG. 12A, there is shown subroutine 560 which is run before the dimensioning routine 152. The purpose of routine 560 is to calculate the expected position of the section within the gauge and, from the expected position, determine which detectors 14 should be used for determining the location of each corner of the section. Additionally, subroutine 560 calculates the ray number for each detector 14 that would pass through the nominal corner position. This establishes a starting point in the dimensioning routine for searching for the actual corner position and eliminates the additional processing required to determine which detectors 14 to use and where to start the processing.

The detectors 14 used are those (in the case of using corner 1 for a wide flange beam,) that would be to the left of the section and below corner 1 so that they would essentially be in a quadrant of the guage that is below a line drawn through corner 1 and corner 2 and to the left of the left flange of the section. In addition, to further limit the position of those detectors, an angular limit is placed on those two lines, that is the detectors must be more than 6 degrees below the lines through corners 1 and 2 and must be to the left of the line 6 degrees clockwise from a line through corners 1 and 4. All detectors within that range are used.

Similarly for corner 1, detectors 14 above that same line through corner 1 and 2 and more than 6 degrees counter clockwise from that line are used; detectors 14 to the right of a line through corners 1 and 4 and more than 6 degrees clockwise from that line are also used. The entire group of detectors 14 as defined above which usually number approximately sixty for a wide flange are used for determining the location of each corner.

Referring now to subroutine 560, on-page connector I leads control to block 562, where the reasonableness of the nominal dimensions are checked based on the known range of dimensions expected for the particular section. Next in block 564, the nominal corner x and y coordinates are calculated assuming the section is resting on a roller table which has a known y position and assuming that the section is centered in the x direction within the gauge. In block 566, angular limits for selecting detectors for each corner are calculated.

Next, in block 568 a loop is initiated through the four corners. In block 570, a detector index is set to zero. In block 572, a loop is initiated through all detectors. In 574, the angle from the detector to the nominal corner position is calculated. In block 576 and 578, a check is made of whether the angle calculated in 574 is either above the high limits or below the low limit for the angular limits set for the corner under consideration. If it is within those limits, the detector index is incremented and both the detector number and the angle are saved. If the angle is outside of the established limits, this means that the detector is not considered usable for that corner and control moves to decision block 584 and back up to block 572 to repeat the loop. When the loop has sequenced through all detectors, control goes to block 586 where the detector index number (number of usable detectors) is saved. In 588 a check is made of whether or not sequencing through all the four corners has been completed. If Yes, control moves through off-page connector J to block 590.

Figure 12B:
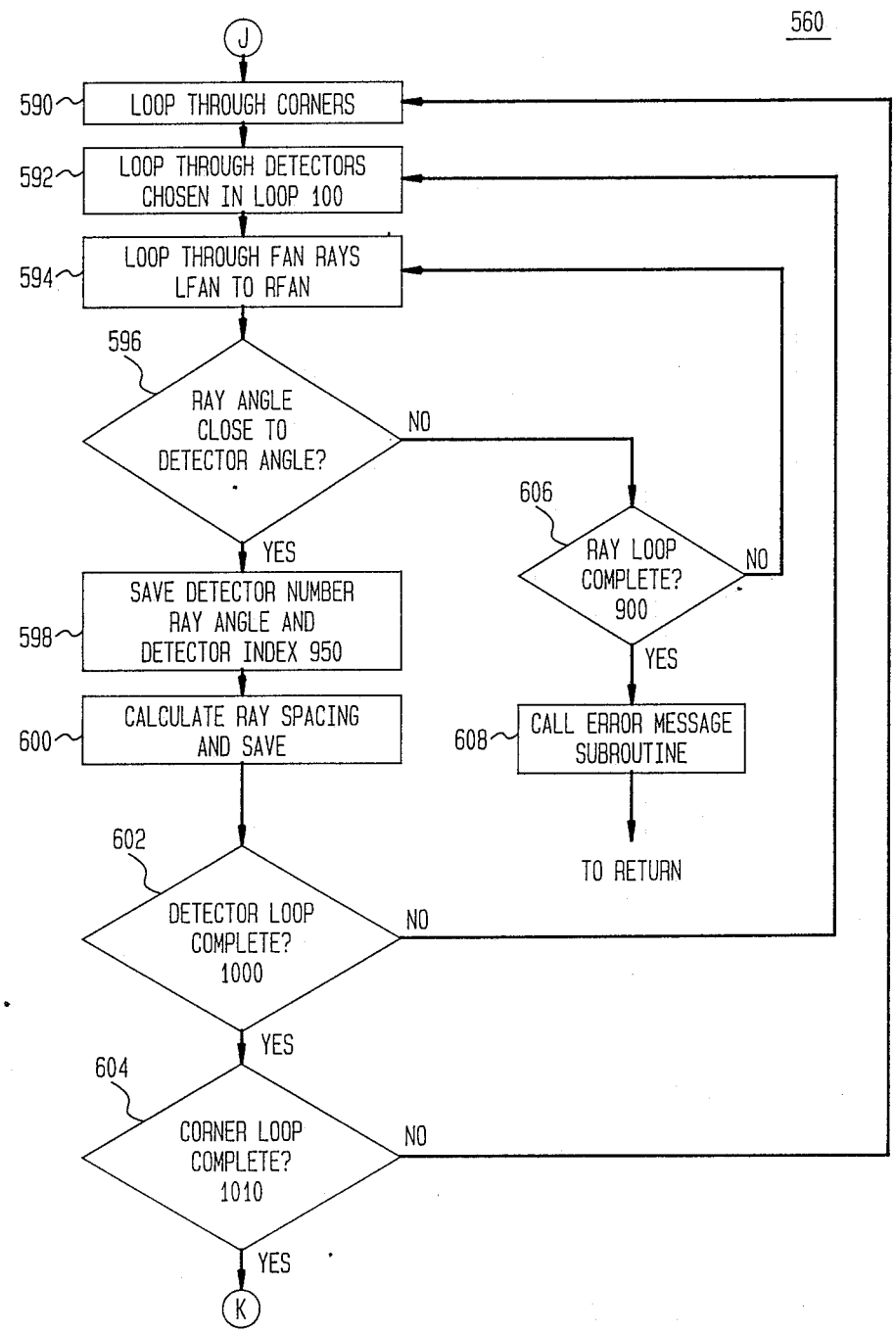

Referring now to FIG. 12B, block 590 initiates a loop through the four corners. In 592, a loop is initiated through just those detectors chosen for the corner in the prior loop. In 594, a loop is initiated to sequence through all fan rays from the minimum to the maximum. In 596, a check is made whether the angle of the current ray being considered is close to the detector angle which had been determined in the prior loop. If it is close, the detector number, ray angle and detector index are saved in a variable that is then passed to the dimensioning routine. If the ray angle is not close to the detector angle, the ray number is incremented until the ray that is closest to the detector angle is determined. If the maximum ray number has been reached (as determined by block 606) and the loop completed, the nominal position of the section has been passed and an error message subroutine is called and control exits the routine.

From block 598, control moves to block 600 where the nominal ray spacing is calculated at the corner location for each detector. This information is used later in calculating the ideal line location that passes through the exact corner in the dimensioning routine. That information is saved and passed to the dimensioning routine 152.

Block 602 verifies that the detector loop is complete. If not, control returns to block 592 to sequence through the remaining detectors. If the detector loop is complete, decision block 604 checks whether the corner loop is complete. If not, control returns to block 590 to increment to the next corner and repeat the loop. If it is complete, the routine is completed and the routine ends.

Referring now to FIG. 13A-F there is shown detector 14 having a metal housing 704 and an end plate 712 for mounting detector 14. At the opposite end of detector 14, annular recess 709, fitted with an O-ring (not shown), is provided for stabilizing the end of detector 14 when the end is fitted into a counterbore (not shown).

Detector 14 is provided with shielding materials and insulating materials to cushion detector 14 when detector 14 is subjected to the physical shocks which are commonplace in the operating environment for which it is intended. Detector 14 is also protected from electrical and magnetic fields which are also present in the environment for which detector 14 is intended because of the high horsepower motors present in this environment. This protection is provided by foil layer 714 which is in electrical contact with housing 704 and is therefore at ground potential. Foil layer 14 is formed of a high reluctance material. A second shielding layer 716 is also provided and is in contact with photomultiplier tube 706. Layers 714, 716 are separated by teflon layer 715 for electrical insulation.

Scintillation crystal 700 is sandwiched between two half-solid cylinders 702 formed of lead. Half-solid cylinders 702 limit the radiation of source 16 from striking crystal 700 except from the one face of crystal 700 which directly faces source 16 and cause the response of detector 14 to roll off as a function of the angle of impinging radiation. Thus, if source 16 is not directly across from detector 14 and the radiation impinging on crystal 700 is at some angle with respect to the detector 14, half-solid cylinders 702 roll off the response of crystal 700 to source 16. Therefore, crystal 700 may respond to beams at somewhat of an angle rather than directly head on but not beyond a certain angle. Half-solid cylinders 702 also shield crystal 700 from scatter from nearby objects including adjacent detectors 14. The heavy materials of cylinders 702 are supported by filling material 710 within housing 704.

Scintillation crystal 700 of detector 14 is oriented to present a cross section or side to a radiation fan beam emitted from source 16 to detect a relatively thin segment of a fan ray 24a-n. The dimensions of crystal 700 are one inch by one inch by two-tenths of an inch. The one inch dimension presented to the fan ray determines the efficiency of scintillation crystal 700 in absorbing the energy from the fan ray. The 0.2 inch dimension provides for detection of a plus and minus thirty degree fan.

The 0.2 inch dimension of crystal 700 also determines the sampling width across the plus and minus thirty degree fan that detector 14 receives. It determines the minimum resolution with which detector 14 may determine the position of a corner or an edge of object 22. Graph 800 shows the relationship between the voltage output of detector 14 and the angle of incidence of radiation. This response is a result of the shape of half-solid cylinders 702 and it permits detector 14 to respond to the moving source when the source is directly in line as well as when the source is at a small angle. The circular shape thus avoids the problems of rectangular elements which present a more uniform thickness for more uniform attenuation. Thus, detector 14 is provided with a larger acceptance angle.

The assembly including half-solid cylinder 702 and crystal 700 is cemented to photomultiplier tube 706. When gamma energy is absorbed from source 16 and converted to photons by scintillation crystal 700, the photons resulting from scintillation within crystal 700 are detected by photomultiplier tube 706. To trap photons within crystal 700 and prevent the photons from exiting crystal 700 by any path other than through the one face of crystal 700 which is cemented to photomultiplier tube 706, all the remaining faces of crystal 700 are coated with a reflective substance. Thus, light resulting from the conversion from gamma energy to photons may reflect from one face to another inside crystal 700 and then exit crystal 700 through the face of crystal 700 cemented to photomultiplier tube 706. The cement at the interface between crystal 700 and photomultiplier tube 706 is a conventional optical cement which presents a minimum interference to the photons passing from crystal 700 to photomultiplier tube 706.

Photomultiplier tube 706 may be a conventional tube such as Hammatsu R268. Crystal 700 may be a BGO and may be formed of a plurality of crystal segments.

Figure 13A:
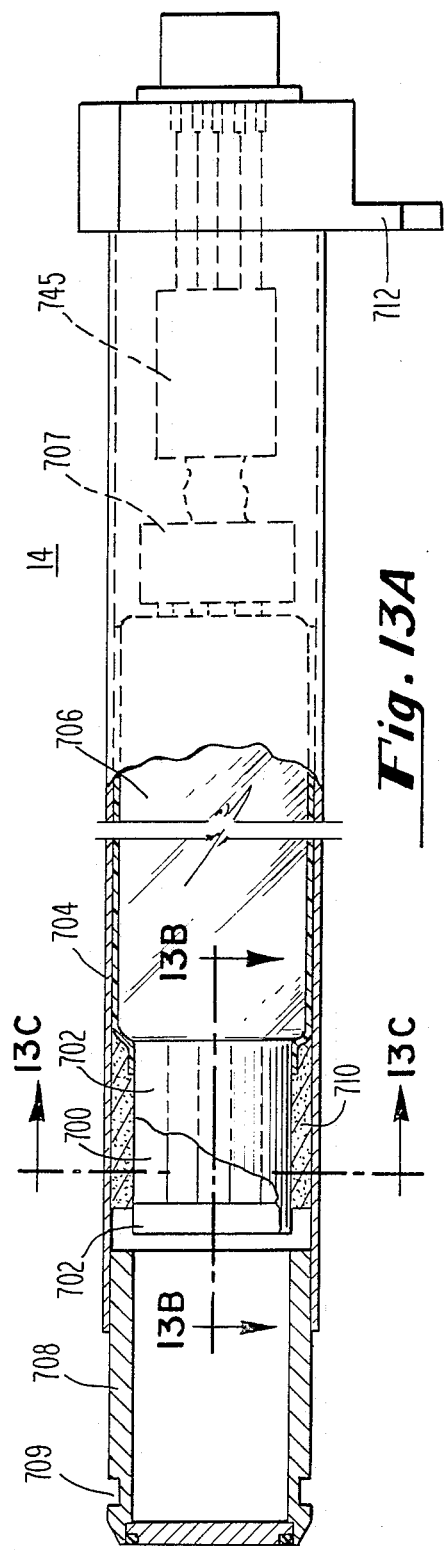
FIGS. 13A-D show the physical composition of gamma radiation detector of the scanning system of FIG. 1.
Figure 13B:
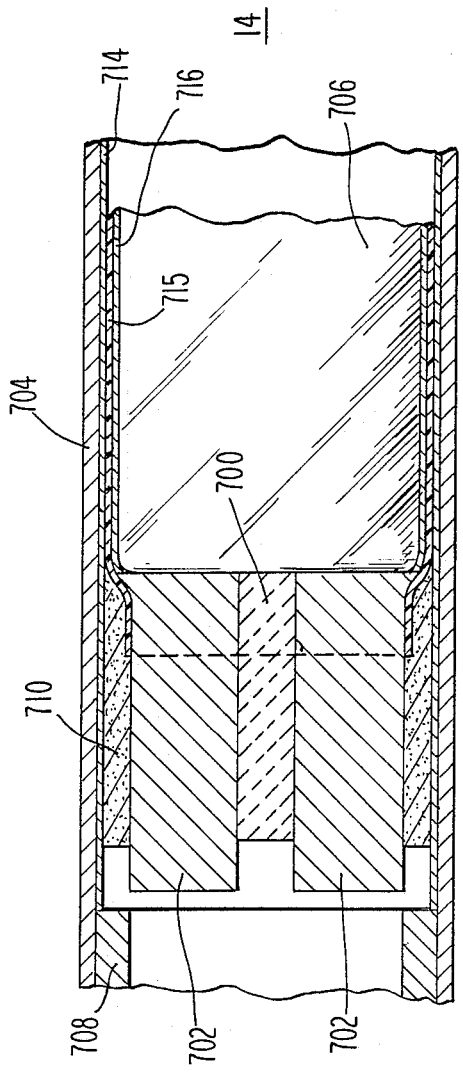
Figure 13C:
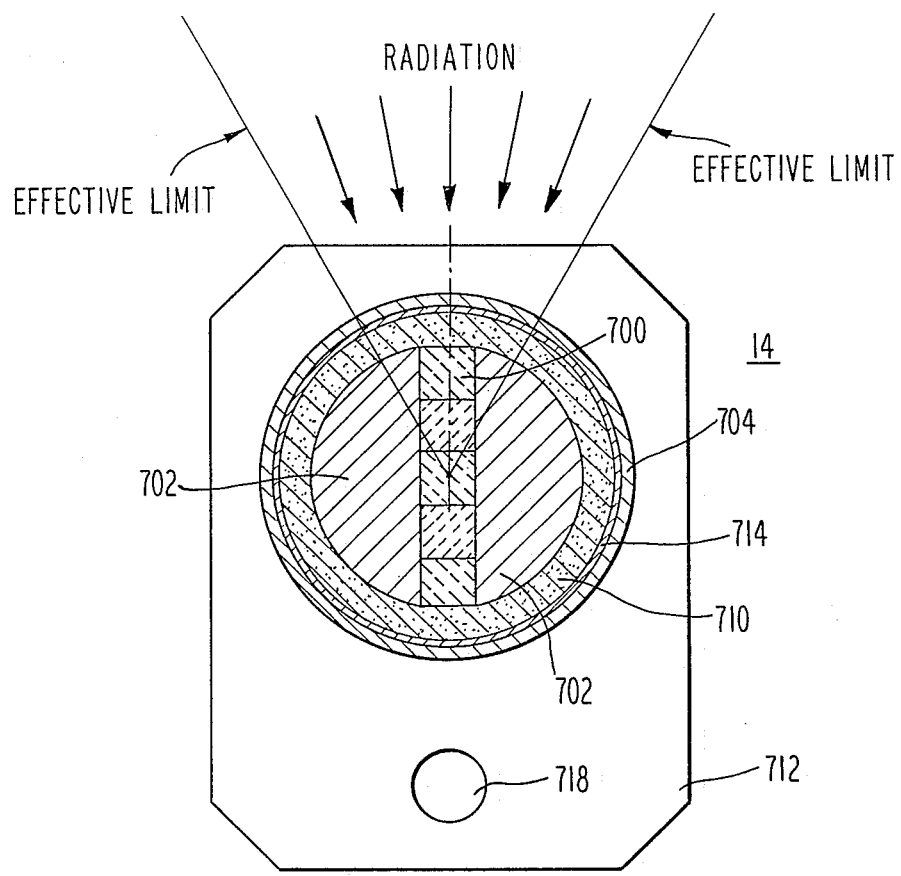
Figure 13D:
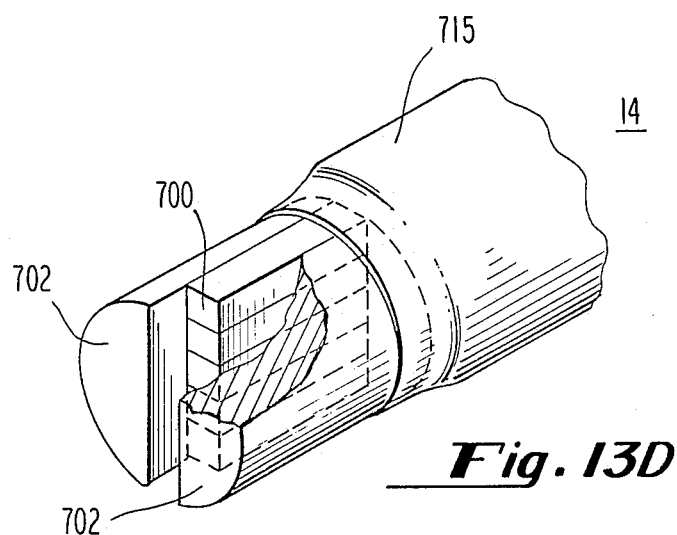
Figure 13E:
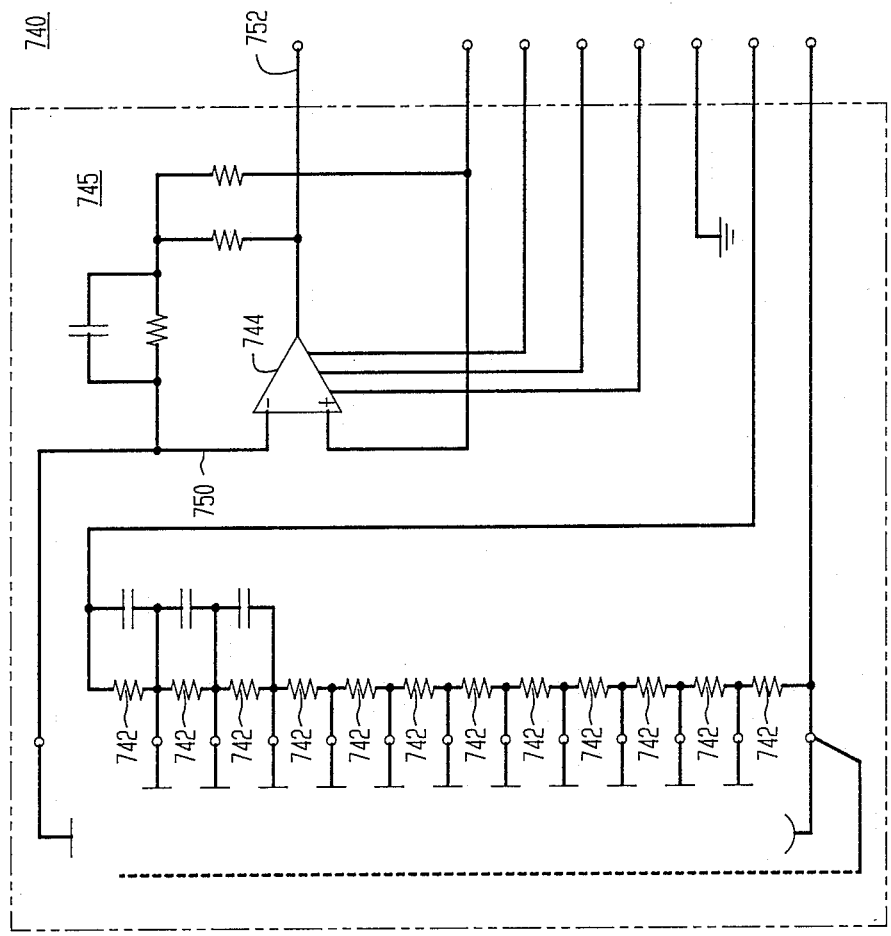
FIG. 13E illustrates the electronic circuitry of the gamma radiation detector of FIGS. 13A-D.
Figure 13F:
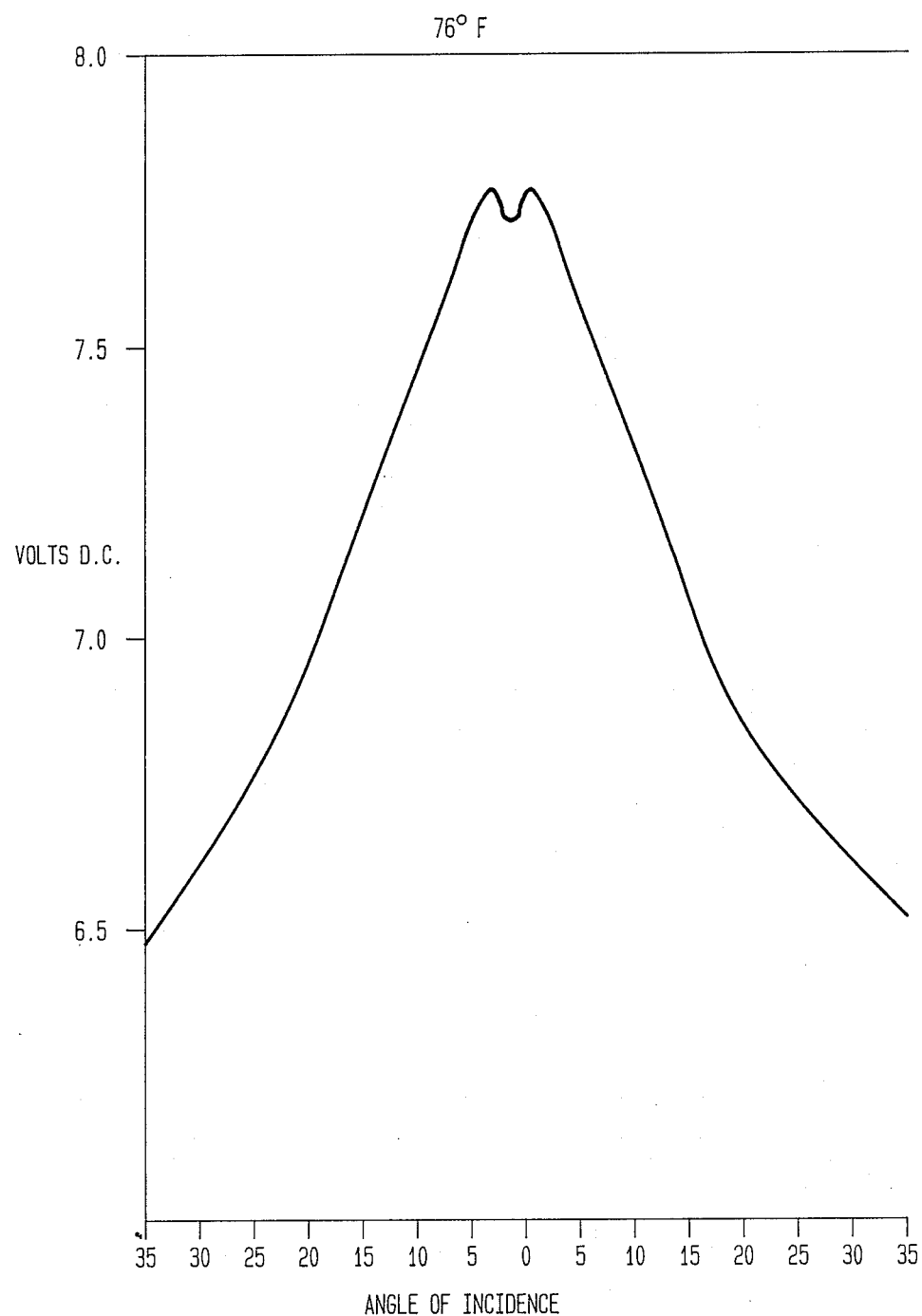
FIG. 13F is a graph showing the relationship between the voltage output of the detector and the angle of incidence of radiation.

Circuit 740 of detector 14 is shown in FIG. 13E, including dynode chain 746 comprising resistors 742 as well as preamplifier 745. Dynode 746 is conventional and is located within socket assembly 707.

The current output of the anode of photomultiplier tube 706 is applied to input 750 of preamplifier 745. Feedback operational amplifier 744 of preamplifier 745 provides a voltage level output in accordance with the level of current from the anode of photomultiplier tube 706 received by amplifier input 750. Amplifier 744 converts current to voltage and then provides a gain of approximately one hundred and provides a voltage level output at terminal 752 which is related to the level of radiation striking crystal 700.

When detector 14 is calibrated, two types of measurements are performed. One is the air measurement in which the level of radiation reaching detector 14 without any object 22 is represented typically by a voltage of eight volts. A second measurement is performed when an object 22 is in the gauge and radiation is at least partially intercepted by object 22 causing a lower voltage measurement to be detected at terminal 752. The difference in the two measurements depends upon the thickness of object 22. The ratio of the measured density to the initial density is then determined.

```
      PROGRAM TOMDIM
      IMPLICIT INTEGER (G,P-Q)
      IMPLICIT INTEGER*2 (K)
      INCLUDE 'CT:[MJF]TOMCOM.CMN/LIST'
      INCLUDE 'CT:[MJF]HEADER.CMN/LIST'
      INCLUDE 'CT:[MJF]TOMBUF.CMN/LIST'
      INCLUDE 'CT:[MJF]TOMQUE.CMN/LIST'
      INCLUDE 'CT:[MJF]TOMGEF.CMN/LIST'
      INTEGER BUFFER, HEADR, SS$_WASSET, BOTH
      PARAMETER (SS$_WASSET = 9)
      PARAMETER (BUFFER = 1)
      PARAMETER (HEADR = 2)
      PARAMETER (BOTH = 3)
      PARAMETER (MASK1 = ISHFT(1,GEF__SHUTDOWN-64) +
     1              ISHFT(1,GEF__ACTTOMDIM-64) )
      PARAMETER (NUM_RWORDS = NUM_WORDS+4)
      PARAMETER (MAN_DIM = 32)
      COMMON /LOCAL/ IBUFER, IDATHD, IRSTHD, LUP, ISCAN,
     1              IERDET, IDETCOM
      INTEGER SYS$READEF, SYS$WFLOR, SYS$PURGWS
      INTEGER SYS$BINTIM, SYS$CANTIM, SYS$SETIMR
      INTEGER QUE_INSERT, QUE_REMOVE, QUE_DBGMSG
      INTEGER INADR(2) /0,'7FFFFFFF'X/, TIMADRA(2)
      INTEGER JENTRY(NUM_RWORDS/2)
      EQUIVALENCE (IENTRY, JENTRY)
      INTEGER*2 IENTRY(NUM_RWORDS)/NUM_RWORDS*0/
      INTEGER*2 IREQST(NUM_WORDS)/NUM_WORDS*0/
      INTEGER*2 ICOMPL
      EXTERNAL AST
      CHARACTER*8 TIMBUFA /'0 :3:00'/

LUP = 75
      CALL SHTIME ('ENTRY TO TOMDIM')
      CALL READP
      ISTAT = SYS$BINTIM (TIMBUFA, TIMADRA)
      IF ( .NOT. ISTAT )
```

```
     1     CALL QUE_DBGMSG ('SYS$BINTIM ERROR', MSG_ERR)
  1000     CONTINUE
           IF (SYS$READEF(%VAL(GEF__SHUTDOWN),ISTATE) .EQ. SS$_WASSET) THEN
             CALL QUE_DBGMSG ('SHUTDOWN REQUEST BEING PROCESSED', MSG_DBG)
             GO TO 8000
           ENDIF
           ISTAT = QUE_REMOVE(QUE__TOMDIM, NUM_WORDS, IREQST)
           IF (.NOT. ISTAT) GO TO 7000
           ISTAT = SYS$CANTIM (%VAL(1), )
           IF ( .NOT. ISTAT) CALL QUE_DBGMSG ('SYS$CANTIM ERROR', MSG_ERR)
           ISCAN = IREQST(1)
           IBUFER = IREQST(2)
           IDATHD = IREQST(3)
           IRSTHD = IREQST(4)
           GO TO (3100, 3200, 3300, 3400, 3500), ISCAN
           CALL QUE_DBGMSG ('ERROR IN PROCESSING REQUEST CODE', MSG_ERR)
           GO TO 1000
  3100     CONTINUE
  3200     CONTINUE
  3300     CONTINUE
  3400     CONTINUE
           CALL QUE_DBGMSG ('START OF COMP SUBROUTINE', MSG_DBG)
           CALL COMP
           CALL QUE_DBGMSG ('END OF COMP SUBROUTINE', MSG_DBG)
           CALL WPFOOT
           ICOMPL ='CS'
           IENTRY(1) = PKT__RESULT
           IENTRY(2) = ISCAN
           IENTRY(3) = 2
           IENTRY(4) = IRSTHD
           JENTRY(3) = RESULT(IRSTHD)
           ISTAT = QUE_INSERT (QUE__TOMINT, NUM_RWORDS, IENTRY)
           ISTAT = QUE_INSERT (QUE__TOMPRT, NUM_RWORDS, IENTRY)
           ISTAT = QUE_INSERT (QUE__TOMDSP, NUM_RWORDS, IENTRY)
           IF (HASTOP(IRSTHD)) CALL COMPLETE (ICOMPL, MAN_DIM)
           CALL DALLOCATE (BUFFER)
           IF (ISCAN .GT. 1) CALL DALLOCATE (HEADR)
           GO TO 6000
  3500     CONTINUE
           IENTRY(1) = PKT__END
           IENTRY(2) = 0
           IENTRY(3) = 2
           IENTRY(4) = IRSTHD
           JENTRY(3) = RESULT(IRSTHD)
           ISTAT = QUE_INSERT (QUE__TOMINT, NUM_RWORDS, IENTRY)
           ISTAT = QUE_INSERT (QUE__TOMPRT, NUM_RWORDS, IENTRY)
           ISTAT = QUE_INSERT (QUE__TOMDSP, NUM_RWORDS, IENTRY)
           IDATHD = IREQST(4)
           CALL DALLOCATE (HEADR)
           GO TO 6000
  6000     CONTINUE
           GO TO 1000
  7000     CONTINUE
           CALL QUE_DBGMSG ('PROCESSING REQUEST QUEUE EMPTY', MSG_DBG)
           IF (ASTOP .OR. .NOT. ADIM) THEN
```

```
            ISTAT = SYS$PURGWS (INADR)
            IF (.NOT. ISTAT) CALL QUE_DBGMSG ('SYS$PURGWS ERROR', MSG_ERR)
         ELSE
            ISTAT = SYS$SETIMR ( , TIMADRA, AST, %VAL(1))
            IF ( .NOT. ISTAT )
    1          CALL QUE_DBGMSG ('SYS$SETIMR ERROR', MSG_ERR)
         ENDIF
         ISTAT = SYS$WFLOR (%VAL(GEF__ACTTOMDIM), %VAL(MASK1))
         IF (.NOT. ISTAT) CALL QUE_DBGMSG
    X          ('SYS$WFLOR ERROR GEF__ACTTOMDIM', MSG_ERR)
         GO TO 1000
 8000    CONTINUE
         CALL SHTIME ('TOMDIM EXIT')
         STOP
         END
         SUBROUTINE SHTIME (COMENT)
         BYTE CTIME(8)
         CHARACTER*(*) COMENT
         CALL QUE_DBGMSG (COMENT, MSG_DBG)
         RETURN
         END
         SUBROUTINE AST(ASTPRM)
         IMPLICIT INTEGER (A-Z)
         PARAMETER (MSG_DBG=0, MSG_ERR=1, MSG_PRT=3)
         INTEGER INADR(2) /0,'7FFFFFFF'X/
         GO TO (301), %LOC(ASTPRM)
         CALL QUE_DBGMSG ('INVALID AST PARAMETER RECEIVED', MSG_ERR)
         GO TO 800
 301     CONTINUE
         ISTAT = SYS$PURGWS (INADR)
         IF (.NOT. ISTAT) CALL QUE_DBGMSG ('SYS$PURGWS ERROR', MSG_ERR)
         GO TO 800
 800     CONTINUE
         RETURN
         END
         SUBROUTINE COMPLETE (ICOMPL, IFUNCT)
         IMPLICIT INTEGER (A-Z)
         INCLUDE 'CT:[MJF]TOMGEF.CMN/NOLIST'
         INCLUDE 'CT:[MJF]TOMQUE.CMN/NOLIST'
         PARAMETER (SS$_WASSET = 9)
         PARAMETER (MASK1 = ISHFT(1,GEF__SHUTDOWN-64) +
    1                      ISHFT(1,GEF__RDYTOMOPR-64) )
         INTEGER*2 ICOMPL
         INTEGER*2 IENTRY(NUM_WORDS)/NUM_WORDS*0/
 100     CONTINUE
         IENTRY(1) = PKT__DONE
         IENTRY(2) = ICOMPL
         IENTRY(3) = IFUNCT
         ISTAT = QUE_INSERT (QUE__TOMOPR, NUM_WORDS, IENTRY)
         IF (.NOT. ISTAT) THEN
            CALL QUE_DBGMSG ('QUE__TOMOPR BLOCKED', MSG_ERR)
            ISTAT = SYS$WFLOR (%VAL(GEF__RDYTOMOPR), %VAL(MASK1))
            IF (.NOT. ISTAT) CALL QUE_DBGMSG
    X          ('GEF__RDYTOMOPR SYS$WFLOR ERROR', MSG_ERR)
            IF (SYS$READEF(%VAL(GEF_SHUTDOWN),STATE) .EQ. SS$_WASSET)THEN
```

```
          CALL QUE_DBGMSG('SHUTDOWN REQUEST BEING PROCESSED', MSG_DBG)
          STOP
        ENDIF
        GO TO 100
      ENDIF
      RETURN
      END
      SUBROUTINE DALLOCATE (ICODE)
      IMPLICIT INTEGER (A-Z)
      INCLUDE 'CT:[MJF]TOMQUE.CMN/NOLIST'
      PARAMETER (BUFFER = 1)
      PARAMETER (HEADER = 2)
      PARAMETER (BOTH = 3)
      COMMON /LOCAL/  IBUFER, IDATHD, IRSTHD, LUP, ISCAN,
     1                IERDET, IDETCOM
      INTEGER*2 IENTRY(NUM_WORDS) /NUM_WORDS*0/
      CHARACTER*60 OUTLIN
      IF (ICODE .EQ. HEADER .OR. ICODE .EQ. BOTH) THEN
        IF (IDATHD .LE. 0) CALL QUE_DBGMSG
     1        ('INVALID HEADER NUMBER DEALLOCATED', MSG_ERR)
        IENTRY(1) = PKT__FREHDR
        IENTRY(2) = 0
        IENTRY(3) = IDATHD
        IF (ISCAN .NE. 5) THEN
          CALL QUE_INSERT ( QUE__FREHDR, NUM_WORDS, IENTRY)
          WRITE (OUTLIN,1000) IDATHD
1000      FORMAT (1X,'HEADER NUMBER ', I2, ' DEALLOCATED')
        ELSE
          CALL QUE_INSERT ( QUE__HEADER, NUM_WORDS, IENTRY)
          WRITE (OUTLIN,1001) IDATHD
1001      FORMAT (1X,'HEADER NUMBER ', I2, ' PLACED ON RESULT QUEUE')
        ENDIF
        CALL QUE_DBGMSG (OUTLIN, MSG_DBG)
        IDATHD = 0
      ENDIF
      IF (ICODE .EQ. BUFFER .OR. ICODE .EQ. BOTH) THEN
        IF (IBUFER .LE. 0) CALL QUE_DBGMSG
     1        ('INVALID BUFFER NUMBER DEALLOCATED', MSG_ERR)
        WRITE (OUTLIN,2000) IBUFER
2000    FORMAT (1X,'BUFFER NUMBER ', I2, ' DEALLOCATED')
        CALL QUE_DBGMSG (OUTLIN, MSG_DBG)
        IENTRY(1) = PKT__FREBUF
        IENTRY(2) = IBUFER
        IENTRY(3) = 0
        CALL QUE_INSERT ( QUE__FREBUF, NUM_WORDS, IENTRY)
        IBUFER = 0
      ENDIF
      RETURN
      END
      SUBROUTINE READP
      IMPLICIT INTEGER*2 (K)
      INCLUDE 'CT:[MJF]TOMGEF.CMN/NOLIST'
      PARAMETER (MSG_DBG=0, MSG_ERR=1, MSG_PRT=3)
      COMMON /LOCAL/  IBUFER, IDATHD, IRSTHD, LUP, ISCAN,
     1                IERDET, IDETCOM
```

```
      COMMON /PARA1/  NVIEW,DW,DL,DRAD,NS,PS,SR,NFAN,FA,NSPOKE,
     1                NRADPT,RECRAD,CC,CS,XMU,TS,SI,SO,NB,ULL
      REAL*4 GAGDAT(20)
      INTEGER SYS$ASCEFC
      CHARACTER*6 GEFTOM /'GEFTOM'/
      EQUIVALENCE (GAGDAT(1), NVIEW)
      ISTAT = SYS$ASCEFC (%VAL(GEF__ACTTOMINP), GEFTOM, , )
      IF (.NOT. ISTAT) CALL QUE_DBGMSG ('SYS$ASCEFC ERROR', MSG_ERR)
      CALL QUE_DBGMSG('READING TABLES OF CONSTANTS FROM DISC', MSG_DBG)
      OPEN (LUP, READONLY, FILE='GAGDAT', DEFAULTFILE='GAGDAT.TMG',
     1       STATUS='OLD')
      READ (LUP,1010) GAGDAT
1010  FORMAT (F16.3)
      CLOSE (LUP)
      NVIEW  = GAGDAT(1)
      NS     = GAGDAT(5)
      NFAN   = GAGDAT(8)
      NSPOKE = GAGDAT(10)
      NRADPT = GAGDAT(11)
      CALL QUE_DBGMSG ('RUNNING CONST SUBROUTINE',MSG_DBG)
      CALL CONST
      CALL QUE_DBGMSG ('INITIALIZATION COMPLETE', MSG_DBG)
      RETURN
      END
      SUBROUTINE COMP
      IMPLICIT INTEGER*2 (K)
      INCLUDE 'CT:[MJF]HEADER.CMN/NOLIST'
      INCLUDE 'CT:[MJF]TOMBUF.CMN/NOLIST'
      PARAMETER (MSG_DBG=0, MSG_ERR=1, MSG_PRT=3)
      COMMON /LOCAL/  IBUFER, IDATHD, IRSTHD, LUP, ISCAN,
     1                IERDET, IDETCOM
      COMMON /PARA1/  NVIEW,DW,DL,DRAD,NS,PS,SR,NFAN,FA,NSPOKE,
     1                NRADPT,RECRAD,CC,CS,XMU,TS,SI,SO,NB,ULL
      DATA LSCTION /0/
      IF ( SHAPE(IDATHD) .LE. 0 .OR. SHAPE(IDATHD) .GT. 17) THEN
        IF (SHAPE(IDATHD) .LE. 24 .AND. SHAPE(IDATHD) .GT. 0) THEN
          CALL QUE_DBGMSG
     1         ('DIMENSIONING NOT IMPLEMENTED FOR THIS SHAPE', MSG_ERR)
        ELSE
          CALL QUE_DBGMSG ('ILLEGAL SHAPE TYPE', MSG_ERR)
        END IF
        IERDET = 1
        IDETCOM = 0
        GO TO 4000
      END IF
      IDETCOM = 1
      GO TO (1000, 2000, 1200, 1300, 1300, 1300, 1600, 1700, 1800,
     1       1900, 2000, 2100, 2100, 1100, 1100, 2200, 2300)
     2          SHAPE(IDATHD)
1000  IF (LSCTION .NE. SCTION(IDATHD)) THEN
        IERDET = 0
        CALL QUE_DBGMSG ('RUNNING DETRAY SUBROUTINE', MSG_DBG)
        CALL DETRAY
      END IF
      IF (IERDET) GO TO 3900
```

```
              CALL QUE_DBGMSG ('RUNNING DIMENS SUBROUTINE', MSG_DBG)
              CALL DIMENS ( DETDAT(LFAN,1,IBUFER) )
              GO TO 3000
      1200    IF (LSCTION .NE. SCTION(IDATHD)) THEN
                  IERDET = 0
                  CALL QUE_DBGMSG ('RUNNING DETRAY SUBROUTINE', MSG_DBG)
                  CALL DETRAY
              END IF
              IF (IERDET) GO TO 3900
              CALL QUE_DBGMSG ('RUNNING DIMCBL SUBROUTINE', MSG_DBG)
              CALL DIMCBL ( DETDAT(LFAN,1,IBUFER) )
              GO TO 3000
      1100    IF (LSCTION .NE. SCTION(IDATHD)) THEN
                  IERDET = 0
                  CALL QUE_DBGMSG ('RUNNING DETANGL SUBROUTINE', MSG_DBG)
                  CALL DETANGL
              END IF
              IF (IERDET) GO TO 3900
              CALL QUE_DBGMSG ('RUNNING DIMANG SUBROUTINE', MSG_DBG)
              CALL DIMANG ( DETDAT(LFAN,1,IBUFER) )
              GO TO 3000
      1300    IF (LSCTION .NE. SCTION(IDATHD)) THEN
                  IERDET = 0
                  CALL QUE_DBGMSG ('RUNNING DETCSC SUBROUTINE', MSG_DBG)
                  CALL DETCSC
              END IF
              IF (IERDET) GO TO 3900
              CALL QUE_DBGMSG ('RUNNING DIMCBL SUBROUTINE', MSG_DBG)
              CALL DIMCBL ( DETDAT(LFAN,1,IBUFER) )
              GO TO 3000
      1600    IF (LSCTION .NE. SCTION(IDATHD)) THEN
                  IERDET = 0
                  CALL QUE_DBGMSG ('RUNNING DETCZ SUBROUTINE', MSG_DBG)
                  CALL DETCZ
              END IF
              IF (IERDET) GO TO 3900
              CALL QUE_DBGMSG ('RUNNING DIMCZ SUBROUTINE', MSG_DBG)
              CALL DIMCZ ( DETDAT(LFAN,1,IBUFER) )
              GO TO 3000
      1700    IF (LSCTION .NE. SCTION(IDATHD)) THEN
                  IERDET = 0
                  CALL QUE_DBGMSG ('RUNNING DETPZ SUBROUTINE', MSG_DBG)
                  CALL DETPZ
              END IF
              IF (IERDET) GO TO 3900
              CALL QUE_DBGMSG ('RUNNING DIMPZ SUBROUTINE', MSG_DBG)
              CALL DIMPZ ( DETDAT(LFAN,1,IBUFER) )
              GO TO 3000
      1800    CONTINUE
      1900    CONTINUE
              IF (LSCTION .NE. SCTION(IDATHD)) THEN
                  IERDET = 0
                  CALL QUE_DBGMSG ('RUNNING DETPS SUBROUTINE', MSG_DBG)
                  CALL DETPS
              END IF
              IF (IERDET) GO TO 3900
```

```
            CALL QUE_DBGMSG ('RUNNING DIMPS SUBROUTINE', MSG_DBG)
            CALL DIMPS ( DETDAT(LFAN,1,IBUFER) )
            GO TO 3000
 2000       CALL QUE_DBGMSG
     X             ('DIMENSIONING NOT IMPLEMENTED FOR SHAPE', MSG_ERR)
            GO TO 3900
 2100       IF (LSCTION .NE. SCTION(IDATHD)) THEN
                IERDET = 0
                CALL QUE_DBGMSG ('RUNNING DETRAY SUBROUTINE', MSG_DBG)
                CALL DETRAY
            END IF
            IF (IERDET) GO TO 3900
            CALL QUE_DBGMSG ('RUNNING DIMPLT SUBROUTINE', MSG_DBG)
            CALL DIMPLT ( DETDAT(LFAN,1,IBUFER) )
            GO TO 3000
 2200       IF (LSCTION .NE. SCTION(IDATHD)) THEN
                IERDET = 0
                CALL QUE_DBGMSG ('RUNNING DETRAY SUBROUTINE', MSG_DBG)
                CALL DETRAY
            END IF
            IF (IERDET) GO TO 3900
            CALL QUE_DBGMSG ('RUNNING DIMBFR SUBROUTINE', MSG_DBG)
            CALL DIMBFR ( DETDAT(LFAN,1,IBUFER) )
            GO TO 3000
 2300       IF (LSCTION .NE. SCTION(IDATHD)) THEN
                IERDET = 0
                CALL QUE_DBGMSG ('RUNNING DETRAY SUBROUTINE', MSG_DBG)
                CALL DETRAY
            END IF
            IF (IERDET) GO TO 3900
            CALL QUE_DBGMSG ('RUNNING DIMSHT SUBROUTINE', MSG_DBG)
            CALL DIMSHT ( DETDAT(LFAN,1,IBUFER) )
            GO TO 3000
 3900       CALL QUE_DBGMSG ('DIMENSION SET-UP INVALID', MSG_ERR)
            IDETCOM = 0
 3000       LSCTION = SCTION(IDATHD)
 4000       RETURN
            END
            SUBROUTINE WPFOOT
            INCLUDE 'CT:[MJF]HEADER.CMN/NOLIST'
            COMMON /LOCAL/  IBUFER, IDATHD, IRSTHD, LUP, ISCAN,
     1                      IERDET, IDETCOM
            CHARACTER*60 OUTLIN
            CHARACTER*58 ODESCRP /'****'/
            INTEGER*2 OSCTION /-1/
            PARAMETER ( NOUTDIM = 24 )
            IF (DESCRP(IDATHD) .NE. ODESCRP .OR.
     1            OSCTION .NE. SCTION(IDATHD)) THEN
                CALL SHTIME
     X    ('*****************************************************')
                ODESCRP = DESCRP(IDATHD)
                OSCTION = SCTION(IDATHD)
                WRITE (OUTLIN,1010) DATIM(IDATHD).ALL
                CALL SHTIME (OUTLIN)
 1010           FORMAT (5X, A24)
                WRITE (OUTLIN,1000) DESCRP(IDATHD)
```

```
              CALL SHTIME (OUTLIN)
1000          FORMAT (A58)
           ENDIF
           WRITE (OUTLIN,1150) (ACTDIM(I,ISCAN,IRSTHD), I=1,6)
1150       FORMAT ( 6(1PE9.3, 1X) )
           CALL SHTIME (OUTLIN)
           IF (SHAPE(IDATHD) .EQ. 1) THEN
              LASTDIM = 16
           ELSE
              LASTDIM = NOUTDIM
           ENDIF
           VALIDIM(ISCAN,IRSTHD) = IDETCOM
           IF (IDETCOM .NE. 0 .AND. IDETCOM .NE. 2 .AND. IDETCOM .NE. 4
     +           .AND. IDETCOM .NE. 6) THEN
              GDIMSCN(IRSTHD) = GDIMSCN(IRSTHD) + 1
              IF (GDIMSCN(IRSTHD) .EQ. 1) THEN
                 DO 4500 I=1,LASTDIM
                    AVGDIM(I,IRSTHD) = ACTDIM(I,ISCAN,IRSTHD)
4500             CONTINUE
              ELSE
                 DO 5000 I=1,LASTDIM
                    AVGDIM(I,IRSTHD) = ( (GDIMSCN(IRSTHD)-1) *
     1               AVGDIM(I,IRSTHD) + ACTDIM(I,ISCAN,IRSTHD) ) /
     2               GDIMSCN(IRSTHD)
5000             CONTINUE
              ENDIF
           ENDIF
           RETURN
           END
           SUBROUTINE DETRAY
           INCLUDE 'CT:[MJF]HEADER.CMN/NOLIST'
           REAL*4 DETXY(2,NVIEWS), RAY(LFAN:RFAN), PI, ANGL(64,4)
           INTEGER GDI(4), GRI(3,64,4), GD(64,4)
           INTEGER C, D, I, S
           REAL*4 RAD1, RAD2, DETANG(NVIEWS), MINANG, MINDEN
           REAL*4 CXY(2,4), AL(2,4), RG(7,64,4)
           REAL*4 DEPTH, HEIGHT, WT, SLP, FTW, BL, FT, LENB, LENW
           REAL*4 RAYANG, HALFPI, DEL1, DEL2, MHALFPI
           REAL*4 DW, DL, DRAD, PS, SR, FA, RECRAD, CC, CS, XMU, TS, SI
           REAL*4 SO, ULL
           COMMON /LOCAL2/ RAY, DETANG, DETXY
           COMMON /CONSTNT/ PI, HALFPI, THRDPI, INCANG, MHALFPI
           COMMON /PARA1/  NVIEW, DW, DL, DRAD, NS, PS, SR, NFAN, FA,
     +                    NSPOKE, NRADPT, RECRAD, CC, CS, XMU, TS, SI, SO,
     +                    NB, ULL
           COMMON /LOCAL/  IBUFER, IDATHD, IRSTHD, LUP, ISCAN,
     1                    IERDET, IERDIM
           COMMON /GDRAY/ CXY, GRI, GDI, RG
           PARAMETER (MSG_ERR = 1)
           PARAMETER (MINANG = 0.001)
           PARAMETER (MINDEN = .092)
           PARAMETER (DDEPTHMN1 = 4.0)
           PARAMETER (DDEPTHMX1 = 24.0)
           PARAMETER (DHEIGHTMN1 = 3.0)
           PARAMETER (DHEIGHTMX1 = 10.0)
           PARAMETER (DFTMN1 = 0.2)
```

```
PARAMETER (DFTMX1 = 1.2)
PARAMETER (DWTMN1 = 0.15)
PARAMETER (DWTMX1 = 1.0)
PARAMETER (DFTWMN1 = 0.2)
PARAMETER (DFTWMX1 = 1.2)
PARAMETER (DRAD1MN1 = 0.0)
PARAMETER (DRAD1MX1 = 0.6)
PARAMETER (DRAD2MN1 = 0.0)
PARAMETER (DRAD2MX1 = 0.3)
PARAMETER (DDEPTHMN3 = 4.0)
PARAMETER (DDEPTHMX3 = 24.0)
PARAMETER (DHEIGHTMN3 = 2.0)
PARAMETER (DHEIGHTMX3 = 6.0)
PARAMETER (DFTMN3 = 0.2)
PARAMETER (DFTMX3 = 0.75)
PARAMETER (DWTMN3 = 0.2)
PARAMETER (DWTMX3 = 0.9)
PARAMETER (DFTWMN3 = 0.2)
PARAMETER (DFTWMX3 = 1.0)
PARAMETER (DRAD1MN3 = 0.2)
PARAMETER (DRAD1MX3 = 0.75)
PARAMETER (DRAD2MN3 = 0.1)
PARAMETER (DRAD2MX3 = 0.5)
PARAMETER (DDEPTHMN12 = 0.1)
PARAMETER (DDEPTHMX12 = 4.0)
PARAMETER (DHEIGHTMN12 = 6.0)
PARAMETER (DHEIGHTMX12 = 28.0)
PARAMETER (DFTMN12 = 0.1)
PARAMETER (DFTMX12 = 4.0)
PARAMETER (DWTMN12 = 0.0)
PARAMETER (DWTMX12 = 0.0)
PARAMETER (DFTWMN12 = 0.1)
PARAMETER (DFTWMX12 = 4.0)
PARAMETER (DRAD1MN12 = 0.0)
PARAMETER (DRAD1MX12 = 0.0)
PARAMETER (DRAD2MN12 = 0.0)
PARAMETER (DRAD2MX12 = 0.0)
PARAMETER (DDEPTHMN13 = 6.0)
PARAMETER (DDEPTHMX13 = 28.0)
PARAMETER (DHEIGHTMN13 = 0.1)
PARAMETER (DHEIGHTMX13 = 4.0)
PARAMETER (DFTMN13 = 0.0)
PARAMETER (DFTMX13 = 0.0)
PARAMETER (DWTMN13 = 0.1)
PARAMETER (DWTMX13 = 4.0)
PARAMETER (DFTWMN13 = 0.0)
PARAMETER (DFTWMX13 = 0.0)
PARAMETER (DRAD1MN13 = 0.0)
PARAMETER (DRAD1MX13 = 0.0)
PARAMETER (DRAD2MN13 = 0.0)
PARAMETER (DRAD2MX13 = 0.0)
PARAMETER (DDEPTHMN16 = 24.0)
PARAMETER (DDEPTHMX16 = 26.0)
PARAMETER (DHEIGHTMN16 = 1.0)
PARAMETER (DHEIGHTMX16 = 2.0)
PARAMETER (DLENBMN16 = 2.0)
```

```
      PARAMETER (DLENBMX16 = 4.0)
      PARAMETER (DLENWMN16 = 16.0)
      PARAMETER (DLENWMX16 = 18.0)
      PARAMETER (DRAD1MN16 = 0.2)
      PARAMETER (DRAD1MX16 = 0.3)
      PARAMETER (DWTMN16 = 0.4)
      PARAMETER (DWTMX16 = 0.6)
      BL = -4.0
      IF (SHAPE(IDATHD) .EQ. 13) BL = -5.5
      DEPTH = DIM(1,IDATHD)
      HEIGHT = DIM(2,IDATHD)
      FT = DIM(3,IDATHD)
      FTW = DIM(5,IDATHD)
      WT = DIM(6,IDATHD)
      RAD1 = DIM(7,IDATHD)
      RAD2 = DIM(8,IDATHD)
      IF (SHAPE(IDATHD) .EQ. 16) THEN
        LENB = DIM(3,IDATHD)
        LENW = DIM(4,IDATHD)
        RAD1 = DIM(5,IDATHD)
      ENDIF
      IF (SHAPE(IDATHD) .EQ. 1) THEN
        IF (DEPTH  .LT. DDEPTHMN1  .OR. DEPTH  .GT. DDEPTHMX1  .OR.
    2       HEIGHT .LT. DHEIGHTMN1 .OR. HEIGHT .GT. DHEIGHTMX1 .OR.
    3       FT     .LT. DFTMN1     .OR. FT     .GT. DFTMX1     .OR.
    4       WT     .LT. DWTMN1     .OR. WT     .GT. DWTMX1     .OR.
    5       FTW    .LT. DFTWMN1    .OR. FTW    .GT. DFTWMX1    .OR.
    6       RAD1   .LT. DRAD1MN1   .OR. RAD1   .GT. DRAD1MX1   .OR.
    7       RAD2   .LT. DRAD2MN1   .OR. RAD2   .GT. DRAD2MX1)  THEN
          CALL QUE_DBGMSG
    1        ('NOMINAL DIMENSIONS UNREASONABLE', MSG_ERR)
          IERDET = 1
          GO TO 9000
        ENDIF
      ENDIF
      IF (SHAPE(IDATHD) .EQ. 3) THEN
        IF (DEPTH  .LT. DDEPTHMN3  .OR. DEPTH  .GT. DDEPTHMX3  .OR.
    2       HEIGHT .LT. DHEIGHTMN3 .OR. HEIGHT .GT. DHEIGHTMX3 .OR.
    3       FT     .LT. DFTMN3     .OR. FT     .GT. DFTMX3     .OR.
    4       WT     .LT. DWTMN3     .OR. WT     .GT. DWTMX3     .OR.
    5       FTW    .LT. DFTWMN3    .OR. FTW    .GT. DFTWMX3    .OR.
    6       RAD1   .LT. DRAD1MN3   .OR. RAD1   .GT. DRAD1MX3   .OR.
    7       RAD2   .LT. DRAD2MN3   .OR. RAD2   .GT. DRAD2MX3)  THEN
          CALL QUE_DBGMSG
    1        ('NOMINAL DIMENSIONS UNREASONABLE', MSG_ERR)
          IERDET = 1
          GO TO 9000
        ENDIF
      ENDIF
      IF (SHAPE(IDATHD) .EQ. 12) THEN
        IF (DEPTH  .LT. DDEPTHMN12  .OR. DEPTH  .GT. DDEPTHMX12  .OR.
    2       HEIGHT .LT. DHEIGHTMN12 .OR. HEIGHT .GT. DHEIGHTMX12 .OR.
    3       FT     .LT. DFTMN12     .OR. FT     .GT. DFTMX12     .OR.
    4       WT     .LT. DWTMN12     .OR. WT     .GT. DWTMX12     .OR.
    5       FTW    .LT. DFTWMN12    .OR. FTW    .GT. DFTWMX12    .OR.
    6       RAD1   .LT. DRAD1MN12   .OR. RAD1   .GT. DRAD1MX12   .OR.
```

```
7         RAD2    .LT. DRAD2MN12   .OR. RAD2    .GT. DRAD2MX12) THEN
          CALL QUE_DBGMSG
1              ('NOMINAL DIMENSIONS UNREASONABLE', MSG_ERR)
          IERDET = 1
          GO TO 9000
      ENDIF
    ENDIF
    IF (SHAPE(IDATHD) .EQ. 13) THEN
      IF (DEPTH   .LT. DDEPTHMN13  .OR. DEPTH   .GT. DDEPTHMX13  .OR.
2          HEIGHT  .LT. DHEIGHTMN13 .OR. HEIGHT  .GT. DHEIGHTMX13 .OR.
3          FT      .LT. DFTMN13     .OR. FT      .GT. DFTMX13     .OR.
4          WT      .LT. DWTMN13     .OR. WT      .GT. DWTMX13     .OR.
5          FTW     .LT. DFTWMN13    .OR. FTW     .GT. DFTWMX13    .OR.
6          RAD1    .LT. DRAD1MN13   .OR. RAD1    .GT. DRAD1MX13   .OR.
7          RAD2    .LT. DRAD2MN13   .OR. RAD2    .GT. DRAD2MX13)  THEN
         CALL QUE_DBGMSG
1              ('NOMINAL DIMENSIONS UNREASONABLE', MSG_ERR)
          IERDET = 1
          GO TO 9000
      ENDIF
    ENDIF
    IF (SHAPE(IDATHD) .EQ. 16) THEN
      IF (DEPTH   .LT. DDEPTHMN16  .OR. DEPTH   .GT. DDEPTHMX16  .OR.
2          HEIGHT  .LT. DHEIGHTMN16 .OR. HEIGHT  .GT. DHEIGHTMX16 .OR.
3          LENB    .LT. DLENBMN16   .OR. LENB    .GT. DLENBMX16   .OR.
4          LENW    .LT. DLENWMN16   .OR. LENW    .GT. DLENWMX16   .OR.
5          RAD1    .LT. DRAD1MN16   .OR. RAD1    .GT. DRAD1MX16   .OR.
6          WT      .LT. DWTMN16     .OR. WT      .GT. DWTMX16)    THEN
         CALL QUE_DBGMSG
1              ('NOMINAL DIMENSIONS UNREASONABLE', MSG_ERR)
          IERDET = 1
          GO TO 9000
      ENDIF
    ENDIF
    CXY(1,1) = DRAD-DEPTH/2
    CXY(2,1) = HEIGHT+BL
    CXY(1,2) = DRAD+DEPTH/2
    CXY(2,2) = HEIGHT+BL
    CXY(1,3) = DRAD+DEPTH/2
    CXY(2,3) = BL
    CXY(1,4) = DRAD-DEPTH/2
    CXY(2,4) = BL
    AL(1,1) = 7*PI/15
    AL(1,3) = AL(1,1)
    AL(2,1) = PI/30
    AL(2,3) = AL(2,1)
    AL(2,2) = -7*PI/15
    AL(2,4) = AL(2,2)
    AL(1,2) = -PI/30
    AL(1,4) = AL(1,2)
    DO 110 C=1,4
      I = 0
      DO 100 D=1,NVIEWS
        IF (ABS(CXY(1,C)-DETXY(1,D)) .LT. MINDEN) GO TO 100
        SLP = ATAN((CXY(2,C)-DETXY(2,D))/(CXY(1,C)-DETXY(1,D)))
        IF (SLP .GT. AL(1,C)) GO TO 100
```

```
              IF (SLP .LT. AL(2,C)) GO TO 100
              I = I+1
              ANGL(I,C) = SLP
              GD(I,C) = D
100        CONTINUE
           GDI(C) = I
110      CONTINUE
         DO 1010 C=1,4
           DO 1000 D=1,GDI(C)
             GRI(1,D,C) = GD(D,C)
             DO 900 S=LFAN,RFAN
               RAYANG = RAY(S)-DETANG(GD(D,C))
               IF (RAYANG .LT. MHALFPI) THEN
                 RAYANG = RAYANG+PI
                 IF (RAYANG .LT. MHALFPI) RAYANG = RAYANG+PI
               ENDIF
               IF (ABS(RAYANG-ANGL(D,C)) .LT. MINANG) GO TO 950
900          CONTINUE
             CALL QUE_DBGMSG
     +          ('ERROR DETERMINING CLOSEST CORNER RAYS', MSG_ERR)
             IERDET = 1
             GO TO 9000
950          GRI(1,D,C) = GD(D,C)
             GRI(2,D,C) = S
             RG(1,D,C) = RAYANG
             DEL1 = CXY(1,C)-DETXY(1,GD(D,C))
             DEL2 = CXY(2,C)-DETXY(2,GD(D,C))
             RG(3,D,C) = SQRT(DEL1*DEL1+DEL2*DEL2)*
     +           ABS(SIN(RAY(S)-RAY(S-1)))
1000     CONTINUE
1010   CONTINUE
9000   RETURN
       END

SUBROUTINE DIMENS (UL)
INCLUDE 'CT:[MJF]HEADER.CMN/NOLIST'
INCLUDE 'CT:[MJF]THERML.CMN/NOLIST'
REAL*4 DETXY(2,NVIEWS), RAY(LFAN:RFAN), FLA(4), INCANG, RAYANG
REAL*4 WPA(4), DIST1, RG(7,64,4), RAD1, RAD2
REAL*4 CXY(2,4), UL(LFAN:RFAN,NVIEWS), DIST, FLANG(4)
REAL*4 WTPF, WA, LFA, WTT(3), WTA(3), Y, WOCL, WOCR
REAL*4 SLOPE, YTOT, XTOT, RW, WTR(4), TDR(5)
REAL*4 CORAVG(2,4), FTA(3,4), FTTC(3), DENS, INTER, FTW
REAL*4 DEPTH, HEIGHT, HALFPI, THRESH, FLNGHT(4,2), FLNGHT32(4)
REAL*4 THRDPI, DETANG(NVIEWS), MINDEN, MAXSLP
REAL*4 DW, DL, DRAD, PS, SR, FA, RECRAD, CC, CS, XMU, TS, SI
REAL*4 SO, ULL
REAL*4 MHALFPI, PI, OFFSET, CX, CY, WX, WY, FCX, FCY
REAL*4 CORX, CORY, CORF, CORW
INTEGER GRI(3,64,4), TI(7,16,4), GDI(4)
INTEGER TDI(7)
INTEGER ENDRAY, INC
INTEGER WTI(4)
INTEGER WI(3), Z, WPIC
INTEGER S, OFST, DI
```

```
      INTEGER FTIC(3), FD(4)
      INTEGER C, D, X, A, R
      INTEGER TEMPDIF, TEMPDIF1, TEMPDIF3
      CHARACTER*60 OUTLIN
      COMMON /LOCAL2/ RAY, DETANG, DETXY
      COMMON /CONSTNT/ PI, HALFPI, THRDPI, INCANG, MHALFPI
      COMMON /PARA1/  NVIEW, DW, DL, DRAD, NS, PS, SR, NFAN, FA,
     +         NSPOKE, NRADPT, RECRAD, CC, CS, XMU, TS, SI, SO, NB, ULL
      COMMON /LOCAL/  IBUFER, IDATHD, IRSTHD, LUP, ISCAN,
    1                 IERDET, IDETCOM
      COMMON /GDRAY/  CXY, GRI, GDI, RG
      PARAMETER ( MSG_ERR=1 )
      PARAMETER ( RW=.225 )
      PARAMETER ( DENS=3.4028 )
      PARAMETER ( OFST=3 )
      PARAMETER ( THRESH=0.1 )
      PARAMETER ( MINDEN = .092)
      PARAMETER ( MAXSLP = 500.0)
      PARAMETER ( TEMPDIF1 = 275 )
      PARAMETER ( TEMPDIF3 = 100 )
      PARAMETER ( OFFSET = 0.25 )
      PARAMETER ( DC1=0.061 )
      PARAMETER ( DC2=0.300 )
      PARAMETER ( DC3=1.070 )
      PARAMETER ( DC5=0.000653 )

DEPTH = DIM(1,IDATHD)
      HEIGHT = DIM(2,IDATHD)
      FT = DIM(3,IDATHD)
      FTW = DIM(5,IDATHD)
      WT = DIM(6,IDATHD)
      RAD1 = DIM(7,IDATHD)
      RAD2 = DIM(8,IDATHD)
      IDETNO = 0
      IDETND = 0
      IDETOO = 0
      IDETOD = 0
      IERRFLG = 0
      DO 6600 C=1,4
        DO 6500 DI=1,GDI(C)
          D = GRI(1,DI,C)
          S = GRI(2,DI,C)
          IF (((C .EQ. 1 .OR. C .EQ. 2) .AND.
     +        DETXY(1,D) .GT. CXY(1,C)) .OR.
     +        ((C .EQ. 3 .OR. C .EQ. 4) .AND.
     +        DETXY(1,D) .LT. CXY(1,C))) THEN
            IF (UL(S,D) .GT. THRESH) THEN
              DO 6700 X=GRI(2,DI,C),RFAN
                S = X
                IF (S .GT. REFBI(IDATHD)) THEN
                  IF (C .EQ. 1 .OR. C .EQ. 4) THEN
                    IDETNO = IDETNO + 1
                  ELSE
                    IDETND = IDETND + 1
                  ENDIF
                ENDIF
```

```
                    IF (UL(X,D) .LT. THRESH) THEN
                      S = X-1
                      GO TO 6350
                    ENDIF
6700              CONTINUE
                  IBADDET = D
                  IF (C .EQ. 1 .OR. C .EQ. 4) THEN
                    IDETOO = IDETOO + 1
                  ELSE
                    IDETOD = IDETOD + 1
                  ENDIF
                  GRI(3,DI,C) = 0
                  GOTO 6500
                ELSE
                  DO 6750 S=GRI(2,DI,C),LFAN,-1
                    IF (UL(S,D) .GT. THRESH) GO TO 6350
6750              CONTINUE
                  CALL QUE_DBGMSG ('ERROR IN LOOPDO 6750', MSG_ERR)
                  GO TO 9000
                END IF
              ELSE
                IF (UL(S,D) .GT. THRESH) THEN
                  DO 6800 X=GRI(2,DI,C),LFAN,-1
                    S = X
                    IF (S .LT. LEFBI(IDATHD)) THEN
                      IF (C .EQ. 1 .OR. C .EQ. 4) THEN
                        IDETNO = IDETNO + 1
                      ELSE
                        IDETND = IDETND + 1
                      ENDIF
                    ENDIF
                    IF (UL(X,D) .LT. THRESH) THEN
                      S = X+1
                      GO TO 6350
                    END IF
6800              CONTINUE
                  IBADDET = D
                  IF (C .EQ. 1 .OR. C .EQ. 4) THEN
                    IDETOO = IDETOO + 1
                  ELSE
                    IDETOD = IDETOD + 1
                  ENDIF
                  GRI(3,DI,C) = 0
                  GOTO 6500
                ELSE
                  DO 6850 S=GRI(2,DI,C),RFAN
                    IF (UL(S,D) .GT. THRESH) GO TO 6350
6850              CONTINUE
                  CALL QUE_DBGMSG ('ERROR IN LOOP 6850', MSG_ERR)
                  GO TO 9000
                END IF
              END IF
6350          GRI(3,DI,C) = S
              RAYANG = RAY(S)-DETANG(D)
              IF (RAYANG .LT. MHALFPI) THEN
                RAYANG = RAYANG+PI
```

```
            IF (RAYANG .LT. MHALFPI) RAYANG = RAYANG+PI
          ENDIF
          RG(2,DI,C) = RAYANG
          DIST = -DC1 + DC2*SQRT(ABS(SIN(2.0*RAYANG))*UL(S,D))
          IF (FT .LT. 0.5) DIST=DIST+DC5/(ABS(SIN(RAYANG))*FT**DC3)
          RG(6,DI,C) = DIST
          IF (((C.EQ.1 .OR. C.EQ.2) .AND. DETXY(1,D).LT.CXY(1,C)) .OR.
     +        ((C.EQ.3 .OR. C.EQ.4) .AND. DETXY(1,D).GT.CXY(1,C))) THEN
             RG(4,DI,C) = TAN(RAYANG)+DIST*ABS(TAN(RAYANG)-
     +          TAN(RAYANG-RAY(S)+RAY(S-1)))/RG(3,DI,C)
          ELSE
             RG(4,DI,C) = TAN(RAYANG)-DIST*ABS(TAN(RAYANG)-
     +          TAN(RAYANG-RAY(S)+RAY(S+1)))/RG(3,DI,C)
          END IF
          RG(5,DI,C) = DETXY(2,D) - DETXY(1,D)*RG(4,DI,C)
6500    CONTINUE
6600    CONTINUE
        IF (IDETNO .GT. 0) THEN
           WRITE (OUTLIN, 7605 ) IDETNO
           CALL QUE_DBGMSG ( OUTLIN, MSG_ERR )
           IDETCOM = 3
        ENDIF
        IF (IDETND .GT. 0) THEN
           WRITE (OUTLIN, 7610 ) IDETND
           CALL QUE_DBGMSG ( OUTLIN, MSG_ERR )
           IDETCOM = 5
        ENDIF
        IF (IDETNO .GT. 0 .AND. IDETND .GT. 0) THEN
           IDETCOM = 7
     ENDIF
     IF (IDETOO .GT. 0) THEN
        WRITE (OUTLIN, 7615 ) IDETOO
        CALL QUE_DBGMSG ( OUTLIN, MSG_ERR )
        IDETCOM = 9
     ENDIF
     IF (IDETOD .GT. 0) THEN
        WRITE (OUTLIN, 7620 ) IDETOD
        CALL QUE_DBGMSG ( OUTLIN, MSG_ERR )
        IDETCOM = 11
     ENDIF
     IF (IDETOO .GT. 0 .AND. IDETOD .GT. 0) THEN
        IDETCOM = 13
     ENDIF
     IF (IDETOO .GT. 5) THEN
        IDETCOM = 2
        IERRFLG = 1
     ENDIF
     IF (IDETOD .GT. 5) THEN
        IDETCOM = 4
        IERRFLG = 1
     ENDIF
     IF (IDETOO .GT. 5 .AND. IDETOD .GT. 0 .OR.
     +    IDETOO .GT. 0 .AND. IDETOD .GT. 5) THEN
        IDETCOM = 6
     ENDIF
```

```
              IF (IERRFLG .EQ. 1) GOTO 9900
7605    FORMAT ('SECTION NEAR OPERATOR SIDE - ',I3,' DETECTORS')
7610    FORMAT ('SECTION NEAR DRIVE SIDE - ',I3,' DETECTORS')
7615    FORMAT ('SECTION OUT OF FOV ON OPERATOR SIDE - ',I3,' DETECTORS')
7620    FORMAT ('SECTION OUT OF FOV ON DRIVE SIDE - ',I3,' DETECTORS')
              IF (IDETOO+IDETOD .NE. 1.0) IBADDET = 0
              DO 9110 C=1,4
                XTOT = 0
                YTOT = 0
                I = 0
                DO 9100 D=1,GDI(C)-1
                  IF (GRI(3,D,C) .EQ. 0) GOTO 9100
                  DO 9050 S=D+1,GDI(C)
                    IF (GRI(3,S,C) .EQ. 0) GOTO 9050
                    IF (ABS(RG(2,S,C)-RG(2,D,C)) .LT. THRDPI) GO TO 9050
                    I = I+1
                    SOL1 = (RG(5,D,C)-RG(5,S,C))/(RG(4,S,C)-RG(4,D,C))
                    SOL2 = (RG(5,D,C)*RG(4,S,C) - RG(5,S,C)*RG(4,D,C))/
       +               (RG(4,S,C)-RG(4,D,C))
                    XTOT = XTOT+SOL1
                    YTOT = YTOT+SOL2
9050            CONTINUE
9100        CONTINUE
              IF (I .LE. 0) THEN
                CALL QUE_DBGMSG ('ERROR FINDING CORNERS', MSG_ERR)
                GO TO 9000
              ENDIF
              CORAVG(1,C) = XTOT/I
              CORAVG(2,C) = YTOT/I
9110    CONTINUE
              FLA(1)=ATAN((CORAVG(1,1)-CORAVG(1,4))/(CORAVG(2,1)-CORAVG(2,4)))
              FLA(4) = FLA(1)
              FLA(2)=ATAN((CORAVG(1,2)-CORAVG(1,3))/(CORAVG(2,2)-CORAVG(2,3)))
              FLA(3) = FLA(2)
              WEBY = (CORAVG(2,1)+CORAVG(2,4))/2.0
              DO 190 D=62,70
                IF (DETXY(2,D) .LT. WEBY) GO TO 200
190     CONTINUE
              CALL QUE_DBGMSG ('ERROR IN LOOP 190', MSG_ERR)
              GO TO 9000
200     FD(2) = D+2
              FD(3) = D-3
              FD(1) = NVIEWS/2-D
              FD(4) = FD(1) + 5
              IF (FD(1) .LT. 1) FD(1) = FD(1)+NVIEWS
              IF (FD(4) .LT. 1) FD(4) = FD(4)+NVIEWS
              DO 1000 C=1,4
                FTIC(1) = 0
                FTIC(2) = 0
                FTIC(3) = 0
                FTTC(1) = 0
                FTTC(2) = 0
                FTTC(3) = 0
                IF (C .EQ. 1) THEN
                  CX = CORAVG(1,C) + FT
                  CY = CORAVG(2,C) - RAD2 - OFFSET
```

```
            WX = CORAVG(1,C) + FTW
            WY = WEBY + WT/2.0 + RAD1 + OFFSET
            FCX = CORAVG(1,2) - FT
            FCY = CORAVG(2,2) + OFFSET
         ELSE IF (C. EQ. 2) THEN
            CX = CORAVG(1,C) - FT
            CY = CORAVG(2,C) - RAD2 - OFFSET
            WX = CORAVG(1,C) - FTW
            WY = WEBY + WT/2.0 + RAD1 + OFFSET
            FCX = CORAVG(1,1) + FT
            FCY = CORAVG(2,1) + OFFSET
         ELSE IF (C. EQ. 3) THEN
            CX = CORAVG(1,C) - FT
            CY = CORAVG(2,C) + RAD2 + OFFSET
            WX = CORAVG(1,C) - FTW
            WY = WEBY - WT/2.0 - RAD1 - OFFSET
            FCX = CORAVG(1,4) + FT
            FCY = CORAVG(2,4) - OFFSET
         ELSE
            CX = CORAVG(1,C) + FT
            CY = CORAVG(2,C) + RAD2 + OFFSET
            WX = CORAVG(1,C) + FTW
            WY = WEBY - WT/2.0 - RAD1 - OFFSET
            FCX = CORAVG(1,3) - FT
            FCY = CORAVG(2,3) - OFFSET
         ENDIF
         IF (C .EQ. 1 .OR. C .EQ. 3) THEN
            ENDRAY = RFAN
            INC = 1
         ELSE
            ENDRAY = LFAN
            INC = -1
         ENDIF
         DO 900 I=1,14
            IF (C .EQ. 1 .OR. C .EQ. 3) THEN
               D = FD(C)+1-I
            ELSE
               D = FD(C)-1+I
            ENDIF
            IF (D .LT. 1) D = D+NVIEWS
            DO 210 A=1,GDI(C)
               IF (D .EQ. GRI(1,A,C)) TDI(7) = GRI(3,A,C)
210         CONTINUE
            TI(6,I,C) = D
            TI(7,I,C) = TDI(7)
            TDR(1) = (CY - DETXY(2,D))/(CX - DETXY(1,D))
            TDR(2) = (2*CY/3 + WY/3 - DETXY(2,D)) /
     +               (2*CX/3 + WX/3 - DETXY(1,D))
            TDR(3) = (CY/3 + 2*WY/3 - DETXY(2,D)) /
     +               (CX/3 + 2*WX/3 - DETXY(1,D))
            TDR(4) = (WY - DETXY(2,D))/(WX - DETXY(1,D))
            TDR(5) = (FCY - DETXY(2,D))/(FCX - DETXY(1,D))
            DETANGD = DETANG(D)
            DO 260 J=1,5
               TDRATAN = ATAN(TDR(J))*INC
               DO 253 A=TDI(7),ENDRAY,INC
```

```
                  RAYANG = RAY(A) - DETANGD
                  IF (RAYANG .LT. MHALFPI) THEN
                     RAYANG = RAYANG + PI
                     IF (RAYANG .LT. MHALFPI) RAYANG = RAYANG + PI
                  ENDIF
                  IF (TDRATAN .GT. RAYANG*INC) GO TO 255
253            CONTINUE
               CALL QUE_DBGMSG ('ERROR IN LOOP 253', MSG_ERR)
               GO TO 9000
255            TDI(J) = A
               TI(J,I,C) = TDI(J)
260         CONTINUE
            FLMDTANG = FLA(C) - DETANGD
            IF (TDI(5)*INC .GE. TDI(4)*INC) GO TO 500
            IF (TDI(3)*INC .LT. TDI(5)*INC) GO TO 450
            IF (TDI(2)*INC .LT. TDI(5)*INC) GO TO 400
            FTIC(1) = FTIC(1)+INC+TDI(5)-TDI(1)
            DO 350 R=TDI(1),TDI(5),INC
               FTTC(1) = FTTC(1) + UL(R,D)*ABS(COS(RAY(R)+FLMDTANG))
350         CONTINUE
            GO TO 900
400         FTIC(1) = FTIC(1)+INC+TDI(2)-TDI(1)
            DO 410 R=TDI(1),TDI(2),INC
               FTTC(1) = FTTC(1) + ABS(COS(RAY(R)+FLMDTANG))*UL(R,D)
410         CONTINUE
            FTIC(2) = FTIC(2)+TDI(5)-TDI(2)
            DO 420 R=TDI(2)+INC,TDI(5),INC
               FTTC(2) = FTTC(2) + ABS(COS(RAY(R)+FLMDTANG))*UL(R,D)
420         CONTINUE
            GO TO 900
450         FTIC(1) = FTIC(1)+TDI(2)-TDI(1)+INC
            DO 460 R=TDI(1),TDI(2),INC
               FTTC(1) = FTTC(1) + ABS(COS(RAY(R)+FLMDTANG))*UL(R,D)
460         CONTINUE
            FTIC(2) = FTIC(2)+TDI(3)-TDI(2)-INC
            DO 470 R=TDI(2)+INC,TDI(3)-INC,INC
               FTTC(2) = FTTC(2) + ABS(COS(RAY(R)+FLMDTANG))*UL(R,D)
470         CONTINUE
            FTIC(3) = FTIC(3)+TDI(5)-TDI(3)+INC
            DO 480 R=TDI(3),TDI(5),INC
               FTTC(3) = FTTC(3) + ABS(COS(RAY(R)+FLMDTANG))*UL(R,D)
480         CONTINUE
            GO TO 900
500         FTIC(1) = FTIC(1)+TDI(2)-TDI(1)+INC
            DO 510 R=TDI(1),TDI(2),INC
               FTTC(1) = FTTC(1) + ABS(COS(RAY(R)+FLMDTANG))*UL(R,D)
510         CONTINUE
            FTIC(2) = FTIC(2)+TDI(3)-TDI(2)-INC
            DO 520 R=TDI(2)+INC,TDI(3)-INC,INC
               FTTC(2) = FTTC(2) + ABS(COS(RAY(R)+FLMDTANG))*UL(R,D)
520         CONTINUE
            FTIC(3) = FTIC(3)+TDI(4)-TDI(3)+INC
            DO 530 R=TDI(3),TDI(4),INC
               FTTC(3) = FTTC(3) + ABS(COS(RAY(R)+FLMDTANG))*UL(R,D)
530         CONTINUE
900      CONTINUE
```

```
          IF (ABS(FTIC(1)) .LE. 0 .OR. ABS(FTIC(2)) .LE. 0 .OR.
    X         ABS(FTIC(3)) .LE. 0) THEN
            CALL QUE_DBGMSG ('FLANGE THICKNESS ERROR', MSG_ERR)
            GO TO 9000
          ENDIF
          FTA(1,C) = FTTC(1) / ABS(FTIC(1)*XMU)
          FTA(2,C) = FTTC(2) / ABS(FTIC(2)*XMU)
          FTA(3,C) = FTTC(3) / ABS(FTIC(3)*XMU)
          DIST = ABS(CORAVG(2,C)-WEBY)/3.0 - OFST*.035 - WT/6.0
          FLANG(C) = 60*(ATAN((FTA(2,C)-FTA(1,C))/DIST) +
    +          ATAN((FTA(3,C)-FTA(2,C))/DIST) +
    +          ATAN((FTA(3,C)-FTA(1,C))/(2.0*DIST))) / PI
1000    CONTINUE
        WI(1) =
        WI(2) =
        WI(3) =
        WTT(1) = 0
        WTT(2) = 0
        WTT(3) = 0
        CX1 = CORAVG(1,1)+FTW+RAD1
        CX2 = CORAVG(1,2)-FTW-RAD1
        CX3 = CORAVG(1,3)-FTW-RAD1
        CX4 = CORAVG(1,4)+FTW+RAD1
        CY12 = (CORAVG(2,1)+CORAVG(2,2))/2
        CY34 = (CORAVG(2,3)+CORAVG(2,4))/2
        WXL = (CX1+CX4)/2
        WXR = (CX2+CX3)/2
        DO 3000 D=31,35
          IF (ABS(DETXY(1,D)-CX1) .LT. MINDEN) THEN
            SLOPE1 = MAXSLP
          ELSE
            SLOPE1 = (DETXY(2,D)-CY12) / (DETXY(1,D)-CX1)
          ENDIF
          IF (ABS(DETXY(1,D)-CX4) .LT. MINDEN) THEN
            SLOPE2 = MAXSLP
          ELSE
            SLOPE2 = (DETXY(2,D)-CY34) / (DETXY(1,D)-CX4)
          ENDIF
          IF (SLOPE1 .LT. 0 .AND. SLOPE2 .LT. 0 .OR.
    +         SLOPE1 .GE. 0 .AND. SLOPE2 .GE. 0) THEN
            IF (SLOPE1 .GE. SLOPE2) THEN
              WTR(4) = SLOPE1
            ELSE
              WTR(4) = SLOPE2
            ENDIF
          ELSE
            IF (SLOPE1 .GE. SLOPE2) THEN
              WTR(4) = SLOPE2
            ELSE
              WTR(4) = SLOPE1
            ENDIF
          ENDIF
          IF (ABS(DETXY(1,D)-CX2) .LT. MINDEN) THEN
            SLOPE1 = MAXSLP
          ELSE
```

```
          SLOPE1 = (DETXY(2,D)-CY12) / (DETXY(1,D)-CX2)
        ENDIF
        IF (ABS(DETXY(1,D)-CX3) .LT. MINDEN) THEN
          SLOPE2 = MAXSLP
        ELSE
          SLOPE2 = (DETXY(2,D)-CY34) / (DETXY(1,D)-CX3)
        ENDIF
        IF (SLOPE1 .LT. 0 .AND. SLOPE2 .LT. 0 .OR.
     +      SLOPE1 .GE. 0 .AND. SLOPE2 .GE. 0) THEN
          IF (SLOPE1 .LE. SLOPE2) THEN
            WTR(1) = SLOPE1
          ELSE
            WTR(1) = SLOPE2
          ENDIF
        ELSE
          IF (SLOPE1 .LE. SLOPE2) THEN
            WTR(1) = SLOPE2
          ELSE
            WTR(1) = SLOPE1
          ENDIF
        ENDIF
        IF (ABS(DETXY(1,D) - 2*WXR/3 - WXL/3) .LT. MINDEN) THEN
          WTR(2) = MAXSLP
        ELSE
          WTR(2) = (DETXY(2,D) - WEBY) / (DETXY(1,D) - 2*WXR/3 - WXL/3)
        ENDIF
            IF (ABS(DETXY(1,D) - WXR/3 - 2*WXL/3) .LT. MINDEN) THEN
              WTR(3) = MAXSLP
            ELSE
              WTR(3) = (DETXY(2,D) - WEBY) / (DETXY(1,D) - WXR/3 - 2*WXL/3)
            ENDIF
            DETANGD = DETANG(D)
            DO 2700 J= 1,4
              WTRATAN = ATAN(WTR(J))
              IF (WTR(J) .GT. 0) THEN
                DO 2600 I=RFAN,LFAN,-1
                  RAYANG = RAY(I) - DETANGD
                  IF (RAYANG .LT. MHALFPI) THEN
                    RAYANG = RAYANG + PI
                    IF (RAYANG .LT. MHALFPI) RAYANG = RAYANG + PI
                  ENDIF
                  IF (WTRATAN .LT. RAYANG) GO TO 2610
 2600           CONTINUE
              ELSE
                DO 2605 I=LFAN,RFAN
                  RAYANG = RAY(I) - DETANGD
                  IF (RAYANG .LT. MHALFPI) THEN
                    RAYANG = RAYANG + PI
                    IF (RAYANG .LT. MHALFPI) RAYANG = RAYANG + PI
                  ENDIF
                  IF (WTRATAN .GT. RAYANG) GO TO 2610
 2605           CONTINUE
              ENDIF
              CALL QUE_DBGMSG ('ERROR IN LOOP 2600', MSG_ERR)
              GO TO 9000
 2610         WTI(J) = I
```

```
2700    CONTINUE
        WI(1) = WI(1)+WTI(2)-WTI(1)
        DO 2900 R=WTI(1),WTI(2)-1
          WTT(1) = WTT(1) + ABS(SIN(RAY(R)-DETANGD))*UL(R,D)
2900    CONTINUE
        WI(2) = WI(2)+WTI(3)-WTI(2)+1
        DO 2920 R=WTI(2),WTI(3)
          WTT(2) = WTT(2) + ABS(SIN(RAY(R)-DETANGD))*UL(R,D)
2920    CONTINUE
        WI(3) = WI(3)+WTI(4)-WTI(3)
        DO 2940 R=WTI(3)+1,WTI(4)
          WTT(3) = WTT(3) + ABS(SIN(RAY(R)-DETANGD))*UL(R,D)
2940    CONTINUE
3000    CONTINUE
        IF (WI(1) .GT. 0) THEN
          WTA(1) = WTT(1) / (WI(1)*XMU)
        ELSE
          WTA(1) = 0
          CALL QUE_DBGMSG ('WEB THICKNESS ERROR', MSG_ERR)
        ENDIF
        IF (WI(2) .GT. 0) THEN
          WTA(2) = WTT(2) / (WI(2)*XMU)
        ELSE
          WTA(2) = 0
          CALL QUE_DBGMSG ('WEB THICKNESS ERROR', MSG_ERR)
        ENDIF
        IF (WI(3) .GT. 0) THEN
          WTA(3) = WTT(3) / (WI(3)*XMU)
        ELSE
          WTA(3) = 0
          CALL QUE_DBGMSG ('WEB THICKNESS ERROR', MSG_ERR)
        ENDIF
        DO 3350 C=1,4
          Z = 0
          IF (C .EQ. 1 .OR. C .EQ. 3) THEN
            ENDRAY = RFAN
            INC = 1
          ELSE
            ENDRAY = LFAN
            INC = -1
          ENDIF
          WPIC = 0
          WPTC = 0.0
          DO 3300 I=1,14
            D = TI(6,I,C)
            IF (TI(4,I,C)*INC .GT. TI(5,I,C)*INC) GO TO 3300
            Z = Z+1
            IF (Z .EQ. 1) GO TO 3300
            DETANGD = DETANG(D)
            DO 3200 A=TI(4,I,C),ENDRAY,INC
              IF (ABS(COS(RAY(A)-DETANGD))*UL(A,D) .GT.
     +          XMU*(FTA(3,C)+THRESH)) GO TO 3205
3200        CONTINUE
            CALL QUE_DBGMSG ('ERROR IN LOOP 3200', MSG_ERR)
            GO TO 9000
```

```
3205         DIST = -RW/2.0 + SQRT(ABS(RW*SIN(2.0*(RAY(A)-DETANGD))*
      +          (UL(A,D)/XMU-FTA(3,C)/ABS(COS(RAY(A)-DETANGD)))))
             IF (C .EQ. 1 .OR. C .EQ. 4) THEN
                XVAL = CORAVG(1,C) + FTA(3,C) - DETXY(1,D)
                YVAL = (CORAVG(2,1)+CORAVG(2,4))/2.0 - DETXY(2,D)
                DIF = SQRT(XVAL*XVAL+YVAL*YVAL) * ABS(RAY(A)-RAY(A-1))
             ELSE
                XVAL = CORAVG(1,C) - FTA(3,C) - DETXY(1,D)
                YVAL = (CORAVG(2,2)+CORAVG(2,3))/2.0 - DETXY(2,D)
                DIF = SQRT(XVAL*XVAL+YVAL*YVAL) * ABS(RAY(A)-RAY(A+1))
             END IF
             DIST1 = -RW/2.0-DIF+SQRT(ABS(RW*SIN(2.0*(RAY(A+1)-DETANGD))*
      +          (UL(A+1,D)/XMU-FTA(3,C)/ABS(COS(RAY(A+1)-DETANGD)))))
             DIST = (DIST+DIST1)/2.0
             RAYA = RAY(A)-DETANGD
             SLOPE = TAN(RAYANG) + INC*DIST*ABS(TAN(RAYANG)-
      +          TAN(RAY(A-INC)-DETANGD))/DIF
             INTER = DETXY(2,D) - DETXY(1,D)*SLOPE
             IF (C .EQ. 1 .OR. C .EQ. 4) THEN
                Y = SLOPE*(CORAVG(1,1)+CORAVG(1,4)+3.0*(FTA(3,1)+FTA(3,4))
      +          /2.0-(FTA(2,1)+FTA(2,4))/2.0)/2.0 + INTER
             ELSE
                Y = SLOPE*(CORAVG(1,2)+CORAVG(1,3)-3.0*(FTA(3,2)+FTA(3,3))
      +          /2.0+(FTA(2,2)+FTA(2,3))/2.0)/2.0 + INTER
             END IF
             WPIC = WPIC+1
             WPTC = WPTC+Y
3300      CONTINUE
          IF (WPIC .GT. 0) THEN
             WPA(C) = WPTC/WPIC
          ELSE
             WPA(C) = 0
             CALL QUE_DBGMSG ('ERROR IN WEB OFFSET LOOP',MSG_ERR)
          ENDIF
3350      CONTINUE
          WOCL = (CORAVG(2,1)+CORAVG(2,4)-WPA(1)-WPA(4)) / 2.0
          WOCR = (CORAVG(2,2)+CORAVG(2,3)-WPA(2)-WPA(3)) / 2.0
3475      CONTINUE
          IF (MEAST(IDATHD) .EQ. 'S') THEN
             IF (SHAPE(IDATHD) .EQ. 3) THEN
                TEMPDIF = TEMPDIF3
             ELSE
                TEMPDIF = TEMPDIF1
             ENDIF
             DEG = MCOUNT*AVGBART(IDATHD) + BCOUNT
             IENTRY = (DEG-DEGBAS)/INTRVL
             IENTRYF = (DEG+TEMPDIF-DEGBAS)/INTRVL
             IF (IENTRY .LT. 0) IENTRY = -1
             IF (IENTRYF .LT. 0) IENTRYF = -1
             IF (IENTRY .GT. MPOINT) IENTRY = MPOINT
             IF (IENTRYF .GT. MPOINT) IENTRYF = MPOINT
             CORX = 2.0 - (MCOR(IENTRY)*DEG+BCOR(IENTRY))   LENGTH (WEB)
             CORY = 2.0 - (MCOR(IENTRYF)*(DEG+TEMPDIF)+BCOR(IENTRYF))
             CORW = MDTCOR(IENTRY)*DEG + BDTCOR(IENTRY)
```

```
              CORF = MDTCOR(IENTRYF)*(DEG+TEMPDIF) + BDTCOR(IENTRYF)
              DO 3600 C=1,4
                 CORAVG(1,C) = CORAVG(1,C) * CORX
                 CORAVG(2,C) = CORAVG(2,C) * CORY
                 FTA(1,C) = FTA(1,C)*CORF
                 FTA(2,C) = FTA(2,C)*CORF
                 FTA(3,C) = FTA(3,C)*CORF
 3600         CONTINUE
              WTA(1) = WTA(1)*CORW
              WTA(2) = WTA(2)*CORW
              WTA(3) = WTA(3)*CORW
           END IF
           LFA = ((FTA(1,1)+FTA(2,1)+FTA(3,1)+FTA(1,4)+FTA(2,4)+FTA(3,4))
      +          /6.0) * (CORAVG(2,1)-CORAVG(2,4)-WTA(3))
           RFA = ((FTA(1,2)+FTA(2,2)+FTA(3,2)+FTA(1,3)+FTA(2,3)+FTA(3,3))
      +          /6.0) * (CORAVG(2,2)-CORAVG(2,3)-WTA(1))
           WA = ((WTA(1)+WTA(2)+WTA(3))/3.0) *
      +          ((CORAVG(1,2)-CORAVG(1,1)+CORAVG(1,3)-CORAVG(1,4))/2.0)
           WTPF = (RFA+LFA+WA) * DENS
           FLNGHT(1,ISCAN) = (CORAVG(2,1)-CORAVG(2,4)-WTA(3))/2 + WOCL
           FLNGHT(2,ISCAN) = (CORAVG(2,2)-CORAVG(2,3)-WTA(1))/2 + WOCR
           FLNGHT(3,ISCAN) = (CORAVG(2,2)-CORAVG(2,3)-WTA(1))/2 - WOCR
           FLNGHT(4,ISCAN) = (CORAVG(2,1)-CORAVG(2,4)-WTA(3))/2 - WOCL
           FLNGHT32(1) = ANINT((FLNGHT(1,ISCAN) -
      +         AINT(FLNGHT(1,ISCAN)))*32)
           FLNGHT32(2) = ANINT((FLNGHT(2,ISCAN) -
      +         AINT(FLNGHT(2,ISCAN)))*32)
           FLNGHT32(3) = ANINT((FLNGHT(3,ISCAN) -
      +         AINT(FLNGHT(3,ISCAN)))*32)
           FLNGHT32(4) = ANINT((FLNGHT(4,ISCAN) -
      +         AINT(FLNGHT(4,ISCAN)))*32)
           DO J=1,4
             IF ((AINT(FLNGHT(J,ISCAN)) .GT. AINT(FLNGHT(1,ISCAN))) .OR.
      +          (AINT(FLNGHT(J,ISCAN)) .GT. AINT(FLNGHT(2,ISCAN))) .OR.
      +          (AINT(FLNGHT(J,ISCAN)) .GT. AINT(FLNGHT(3,ISCAN))) .OR.
      +          (AINT(FLNGHT(J,ISCAN)) .GT. AINT(FLNGHT(4,ISCAN)))) THEN
               FLNGHT32(J) = FLNGHT32(J) + 32
             ENDIF
           ENDDO
           IF ((ISCAN .EQ. 1) .OR. (ISCAN .EQ.2 .AND.
      +         GDIMSCN(IRSTHD) .EQ. 0)) THEN
             DO J = 1,4
               AVGDIM(J+16,IRSTHD) = FLNGHT32(J)
             ENDDO
           ELSE
             DO J = 1,4
               AVGDIM(J+16,IRSTHD) = ANINT(((FLNGHT(J,1)+FLNGHT(J,2))/2 -
      +            AINT((FLNGHT(J,1)+FLNGHT(J,2))/2))*32)
             ENDDO
             DO J = 1,4
               IF ((AINT((FLNGHT(J,1)+FLNGHT(J,2))/2) .GT.
      +              AINT((FLNGHT(1,1)+FLNGHT(1,2))/2)) .OR.
      +             (AINT((FLNGHT(J,1)+FLNGHT(J,2))/2) .GT.
      +              AINT((FLNGHT(2,1)+FLNGHT(2,2))/2)) .OR.
      +             (AINT((FLNGHT(J,1)+FLNGHT(J,2))/2) .GT.
      +              AINT((FLNGHT(3,1)+FLNGHT(3,2))/2)) .OR.
```

```
     +              (AINT((FLNGHT(J,1)+FLNGHT(J,2))/2) .GT.
     +              AINT((FLNGHT(4,1)+FLNGHT(4,2))/2))) THEN
                  AVGDIM(J+16,IRSTHD) = AVGDIM(J+16,IRSTHD) + 32
              ENDIF
          ENDDO
        ENDIF
        ACTDIM(1,ISCAN,IRSTHD) = CORAVG(1,2)-CORAVG(1,1)
        ACTDIM(2,ISCAN,IRSTHD) = CORAVG(1,3)-CORAVG(1,4)
        ACTDIM(3,ISCAN,IRSTHD) = CORAVG(2,1)-CORAVG(2,4)
        ACTDIM(4,ISCAN,IRSTHD) = CORAVG(2,2)-CORAVG(2,3)
        ACTDIM(5,ISCAN,IRSTHD) = (FTA(1,1)+FTA(2,1)+FTA(3,1)) / 3.0
        ACTDIM(6,ISCAN,IRSTHD) = (FTA(1,2)+FTA(2,2)+FTA(3,2)) / 3.0
        ACTDIM(7,ISCAN,IRSTHD) = (FTA(1,3)+FTA(2,3)+FTA(3,3)) / 3.0
        ACTDIM(8,ISCAN,IRSTHD) = (FTA(1,4)+FTA(2,4)+FTA(3,4)) / 3.0
        ACTDIM(9,ISCAN,IRSTHD) = WTA(2)
        ACTDIM(10,ISCAN,IRSTHD) = -FLA(1)*180.0/PI
        ACTDIM(11,ISCAN,IRSTHD) = -FLA(2)*180.0/PI
        ACTDIM(12,ISCAN,IRSTHD) = WOCL * 32.0
        ACTDIM(13,ISCAN,IRSTHD) = WOCR * 32.0
        ACTDIM(14,ISCAN,IRSTHD) = WTPF
        ACTDIM(15,ISCAN,IRSTHD) = WTA(1)
        ACTDIM(16,ISCAN,IRSTHD) = WTA(3)
        ACTDIM(17,ISCAN,IRSTHD) = FLNGHT32(1)
        ACTDIM(18,ISCAN,IRSTHD) = FLNGHT32(2)
        ACTDIM(19,ISCAN,IRSTHD) = FLNGHT32(3)

ACTDIM(20,ISCAN,IRSTHD) = FLNGHT32(4)
        ACTDIM(24,ISCAN,IRSTHD) = IBADDET
        GO TO 9900
9000    CONTINUE
        IDETCOM = 0
9900    RETURN
        END
```

We claim:

1. A method for tomographic imaging of an inanimate object by fan rays detected by a set of detectors for determining a cross-sectional image of the object in a system having a display device, comprising the steps of:
   (a) generating a fan-shaped beam of radiation divided into a plurality of fan ray elements each element having radiation of magnitude sufficient to penetrate the object;
   (b) directing the fan ray elements through a planar section of the object;
   (c) detecting the fan ray elements by the set of detectors and producing signals from the detectors representative of respective intensities of radiation of detected ones of said fan ray elements;
   (d) determining from the intensity signals of the detectors selected coordinates defining a cross-sectional image of the object;
   (e) storing the determined coordinates of the cross-sectional image; and
   (f) displaying the coordinates on the display device.

2. The method of claim 1 wherein the detectors surround the object, further comprising the step of rotating the fan-shaped beam along a circumference surrounding the object.

3. The method of claim 2 wherein step (d) includes determining selected coordinates defining an outer boundary of the object.

4. The method of claim 1 wherein step (d) is followed by the step of determining an area of the cross-sectional image.

5. The method of claim 4 including the further step of determining the weight per unit length of the object in accordance with the determined cross-sectional area and the density of the object.

6. The method of claim 1 wherein the object is a sheet and step (d) is followed by the step of determining the thickness of the sheet.

7. A method for tomographic imaging of an inanimate object by fan rays detected by a set of detectors for determining at least one outer boundary of the object in a system having a display device, comprising the steps of:
   (a) generating a fan-shaped beam of radiation divided into a plurality of fan ray elements each element having radiation of magnitude sufficient to penetrate the object;
   (b) detecting the fan ray elements by the set of detectors and producing signals from the detectors representative of respective intensities of the radiation of detected ones of said fan ray elements;
   (c) determining from the intensity signals of the detectors selected coordinates defining an outer boundary of the object;
   (d) storing the determined coordinates defining the boundary; and
   (e) displaying the coordinates on the display device.

8. The method of claim 7 wherein the detectors surround the object, comprising the further step of rotating the fan-shaped beam along a circumference surrounding the object.

9. The method of claim 7 wherein step (a) includes directing the fan-shaped beam toward the object.

10. The method of claim 7 in which step (c) includes determining from the intensity signals selected coordinates defining corners of an outer boundary of the object.

11. The method of claim 10 comprising the further step of determining from the intensity signals selected coordinates defining two points of an outer boundary of the object for determining a dimension of the object.

12. The method of claim 11 comprising the further steps of:
   (a) storing predetermined coordinates defining corners of an object;
   (b) comparing the determined coordinates and the predetermined coordinates; and
   (c) displaying the differences.

* * * * *